US006086851A

United States Patent [19]
Boni et al.

[11] Patent Number: 6,086,851
[45] Date of Patent: *Jul. 11, 2000

[54] PHARMACEUTICAL COMPOSITIONS CONTAINING INTERDIGITATION-FUSION LIPOSOMES AND GELS

[75] Inventors: Lawrence T. Boni, Monmouth Junction, N.J.; Andrew S. Janoff, Yardley, Pa.; Sharma R. Minchey; Walter R. Perkins, both of Monmouth Junction, N.J.; Christine E. Swenson, Princeton Junction, N.J.; Patrick L. Ahl, Princeton, N.J.; Thomas S. Davis, Valhalla, N.Y.

[73] Assignee: The Liposome Company, Inc., Princeton, N.J.

[*] Notice: This patent is subject to a terminal disclaimer.

[21] Appl. No.: 08/881,651

[22] Filed: Jun. 24, 1997

Related U.S. Application Data

[63] Continuation of application No. 08/315,988, Sep. 30, 1994, Pat. No. 5,820,848, which is a continuation-in-part of application No. 08/136,470, Oct. 13, 1993, abandoned, and a continuation-in-part of application No. 08/066,539, May 24, 1993, abandoned, and a continuation-in-part of application No. 07/961,277, Oct. 14, 1992, abandoned, which is a continuation-in-part of application No. 07/664,576, Mar. 5, 1991, abandoned, which is a continuation-in-part of application No. 07/464,528, Jan. 12, 1990, abandoned.

[51] Int. Cl.$^7$ .......................... A61K 49/04; A61K 9/127; B01J 13/02; B32B 5/16
[52] U.S. Cl. ............................ 424/9.4; 424/450; 264/4.1; 264/4.3; 264/4.32; 428/402.2; 428/402.24
[58] Field of Search .................................. 424/9.4, 9.45, 424/450, 812; 428/402.2, 402.24; 264/4, 4.1, 4.3, 4.6, 4.32; 427/2.14, 213.3, 213.31, 213.32, 213.33; 436/829

[56] References Cited

U.S. PATENT DOCUMENTS

| | | | |
|---|---|---|---|
| 3,993,754 | 11/1976 | Rahman et al. | 424/177 |
| 4,125,410 | 11/1978 | Sears et al. | 424/19 |
| 4,235,871 | 11/1980 | Papahadjopoulos et al. | 424/19 |
| 4,515,736 | 5/1985 | Deamer | 264/4.3 |
| 4,522,803 | 6/1985 | Lenk et al. | 424/1.1 |
| 4,544,545 | 10/1985 | Ryan et al. | 424/1.1 |
| 4,560,665 | 12/1985 | Nakae et al. | 436/829 |
| 4,588,578 | 5/1986 | Fourntain | 424/1.1 |
| 4,789,633 | 12/1988 | Huang et al. | 424/450 |
| 4,877,561 | 10/1989 | Iga et al. | 264/4.3 |
| 4,921,706 | 5/1990 | Roberts et al. | 424/450 |
| 4,944,948 | 7/1990 | Uster et al. | 424/450 |
| 4,962,022 | 10/1990 | Fleming et al. | 435/7 |
| 5,078,986 | 1/1992 | Bosworth et al. | 424/9 |
| 5,312,615 | 5/1994 | Schneider et al. | 424/9.4 |

FOREIGN PATENT DOCUMENTS

| | | |
|---|---|---|
| 0 190 050 | 8/1986 | European Pat. Off. . |
| 86/00238 | 1/1986 | WIPO . |
| 87/00043 | 1/1987 | WIPO . |
| 91/10422 | 7/1991 | WIPO . |

OTHER PUBLICATIONS

Ames, et al., "The Role of Polyamines in the Neutralization of Bacteriophage Deoxyribonucleic Acid", 1960, J. Biol. Chem., 235, 3, 769–775.

Bally, et al., "Dopamine accumulation in large unilamellar vesicles systems induced by transmembrane ion gradients", 1988, Chem. Phys., Lipids, 47, 97–107.

Boni, et al., "Aggregation and Fusion of Unilamellar Vesicles by Poly(Ethylene Glycol)", BBA 775, 1984, 409–418.

Chapman, et al., "Physical Studies of Phospholipids., X. The Effect of Sonication on Aqueous Dispersions of Egg Yolk Lecithin", BBA, 163, 255, 1968.

Chen, et al., "Micro–determination of Phosphorous", 1956, Analytical Chem., 28, 11, 1756.

Chong, P., et al. "A Differential Polarized Phase Fluorometric Study of the Effects of High Hydrostatic Pressure upon the Fluidity of Cellular Membranes", Biochemistry 1983, 22, 409–415.

Eum, et al., "Temperature–Induced Fusion of Small Unilamellar Vesicles Formed from Saturated Long–Chain Lecithins and Diheptanolyphosphatidylcholine", Biochem., 1989, 28:8206–8213.

Liposomes, Marc J. Ostrol, es. Marcel Dekker, Inc., New York, 1983, Chapter 1, "Liposome Preparation: Methods and Mechanisms".

Lopez–Bernstein, et al., "Liposomal Amphotericin B for the Treatment of Systemie Fungal Infections in Patients with Cancer: A Preliminary Study", 1985, J. Infect. Dis., 151, 704–710.

Mayer, etal., Influence of Ion Gradients on the Transbilayer Distribution of Dibucaine in Large Unilamellar Vesicles:, Biochemistry, 27, 2053–2060, 1988.

Mayer et al., "Techniques for Ecapsulating Bioactive Agents into Liposomes", 1986, Chem. Phys. Lipids, 40, 333–345.

Mayer, et al. "Uptake of Adriamycin into Large Unilamellar Vesicles in Response to a pH Gradient.", BBA, 857 (1986), 123–126.

McConnell, et al., "Phospholipid vesicles fusion and drug loading: tempature, solute and cholestorol effects, and, a rapid preparation for solute–loaded vesicles", BBA, 1985, 818:13–22.

Ostro, et al., Amer. J. Hesp. Pharm., "Use of liposomes as injectable–drug delivery systems", Aug. 1989.

Perkins, et al., "The captured volume of multimlamellar Vesicles", BBA, 1988, 943, 103–107.

Rahman, et al., "Liposomal Protection of Adriamycin–induced Cardiotoxity in Mice", 1980, Cancer Res., 40, 1532–1537.

Slater, et al., "Interdigitated Bilayer Membranes", Progress Lipid Res., 27, 325–359, 1988.

Primary Examiner—Jose' G. Dees
Assistant Examiner—Michael G. Hartley
Attorney, Agent, or Firm—Rosanne Goodman

[57] ABSTRACT

This invention provides a composition containing a sized liposome comprising a lipid and an inducer; the sized liposome has a diameter of at most about 1 micron and the inducer is present in an amount effective to induce interdigitation-fusion of the sized liposome. Also provided herein are interdigitation-fusion liposomes and gels, and methods of making the same.

14 Claims, 33 Drawing Sheets

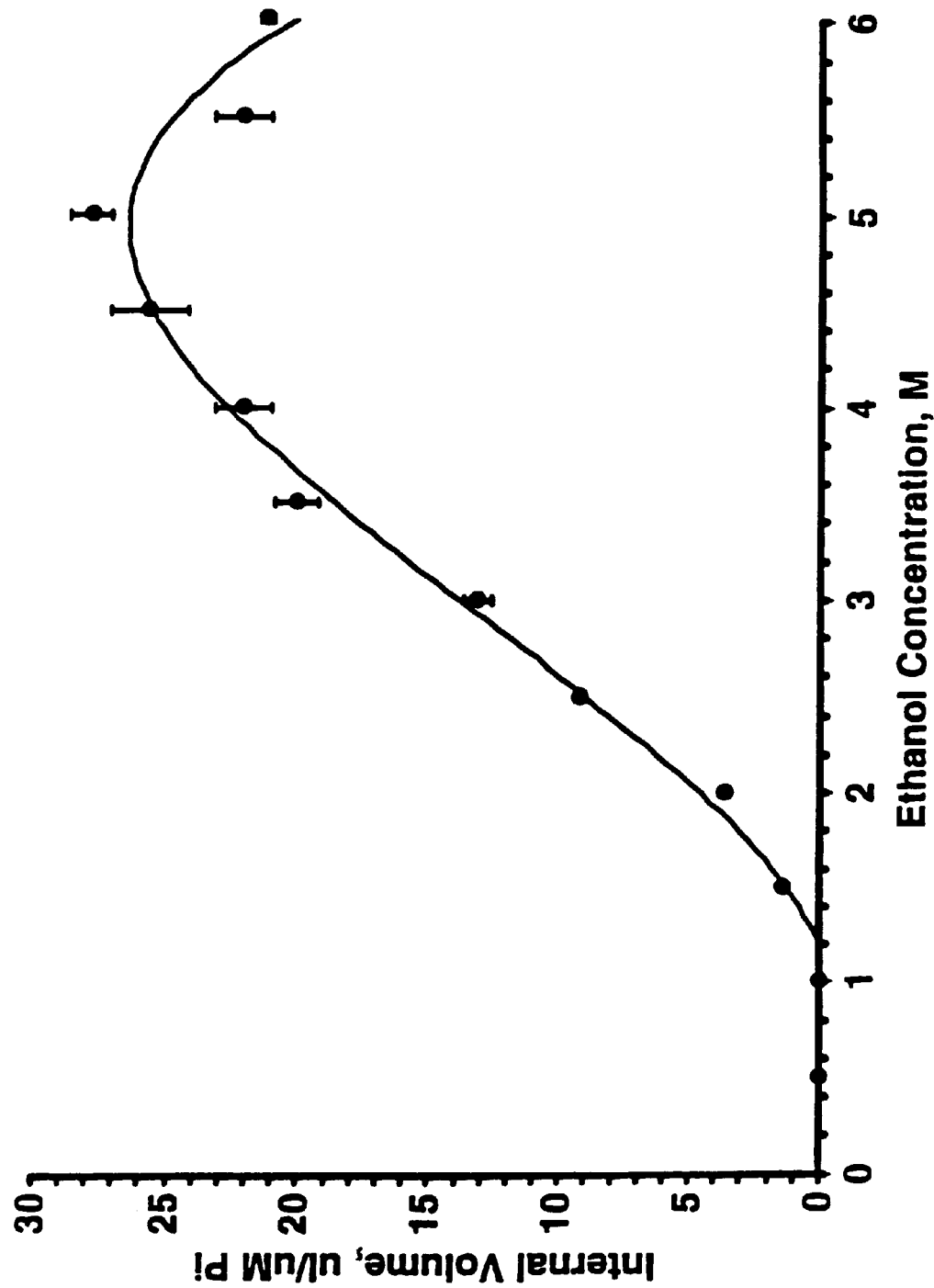

PHARMACEUTICAL COMPOSITIONS CONTAINING INTERDIGITATION-FUSION LIPOSOMES AND GELS

This application is a continuation of application Ser. No. 08/315,988, filed Sep. 30, 1994, now U.S. Pat. No. 5,820,848, which is a continuation-in-part of application Ser. No. 08/136,470, filed Oct. 13, 1993, now abandoned, and a continuation-in-part of application Ser. No. 08/066,539, filed May 24, 1993, now abandoned, and a continuation-in-part of application Ser. No. 07/961,277, filed Oct. 14, 1992, now abandoned, which is a continuation-in-part of application Ser. No. 07/664,576, filed Mar. 5, 1991, now abandoned, which is a continuation-in-part of application No. 07/464,528, filed Jan. 12, 1990, now abandoned.

The therapeutic properties of many drugs may be dramatically improved by the administration in a liposomally encapsulated form (See, for example, Shek and Barber (1986)). Toxicity can be reduced, in comparison to the free form of the drug, meaning that a higher dose of the liposomally encapsulated drug can safely be administered (see, for example, Lopez-Berestein, et al. (1985); and Rahman, et al. (1980)). Benefits obtained from liposomal encapsulation likely result from the altered pharmacokinetics and biodistribution of the entrapped drug. (Ostro, et al. (1989))

Liposomes comprise one or more lipid bilayers, each surrounding entrapped aqueous volume. Liposomes may be unilamellar (single bilayer membrane) or multilamellar (onion-like structures characterized by multiple bilayer membranes, each separated from the next by an aqueous layer). The bilayer is composed of two lipid monolayers having a hydrophobic "tail" region and a hydrophilic "head" region. In the membrane bilayer, the hydrophobic (nonpolar) "tails" of the lipid monolayers orient toward the center of the bilayer, whereas the hydrophilic (polar) "heads" orient toward the aqueous phase.

Liposomes may be produced by a variety of methods (for a review, see, e.g., Cullis et al. (1987)). Bangham's procedure (J. Mol. Biol. (1965)) produces ordinary multilamellar vesicles (MLVs). Lenk et al. (U.S. Pat. Nos. 4,522,803, 5,030,453 and 5,169,637), Fountain et al. (U.S. Pat. No. 4,588,578) and Cullis et al. (U.S. Pat. No. 4,975,282) disclose methods for producing multilamellar liposomes having substantially equal interlamellar solute distribution in each of their aqueous compartments. Paphadjopoulos et al., U.S. Pat. No. 4,235,871, discloses preparation of oligolamellar liposomes by reverse phase evaporation.

Unilamellar vesicles can be produced from MLVs by a number of techniques, for example, the extrusion of Cullis et al. (U.S. Pat. No. 5,008,050) and Loughrey et al. (U.S. Pat. No. 5,059,421)). Sonication and homogenization cab be used to produce smaller unilamellar liposomes from larger liposomes (see, for example, Paphadjopoulos et al. (1968); Deamer and Uster (1983); and Chapman et al. (1968)).

A number of methods are presently available for "charging" liposomes with bioactive agents (see, for example, Rahman et al., U.S. Pat. No. 3,993,754; Sears, U.S. Pat. No. 4,145,410; Papahadjopoulos, et al., U.S. Pat. No. 4,235,871; Lenk et al., U.S. Pat. No. 4,522,803; and Fountain et al., U.S. Pat. No. 4,588,578). Ionizable bioactive agents have been shown to accumulate in liposomes in response to an imposed proton or ionic gradient (see, Bally et al., U.S. Pat. No. 5,077,056; Mayer, et al. (1986); Mayer, et al. (1988); and Bally, et al. (1988)). Liposomal encapsulation could potentially provide numerous beneficial effects for a wide variety of pharmaceutical agents and a high drug to lipid ratio should prove important in realizing the potential of liposomally encapsulated agents. Full references for these citations are provided on the attached form; the contents of their disclosures are incorporated herein by reference.

This invention relates to interdigitation-fusion (IF) liposomes and gels. These liposomes and gels capture high solute to lipid ratios. This invention also relates ,to the discovery of interdigitation of lipids to produce IF gels and liposomes, and the further discovery that such interdigitation to form liposomes according to the present invention is size dependent. Interdigitation of lipids is a phenomenon which has been recently explored in considerable detail by Slater and Huang, 1988. In general, the art describes the interdigitation of various lipid species resulting from either the presence of various inducers and/or acyl chain length asymmetry (See FIGS. 1A and 1B). There has been no report in the literature, however, of the size dependency for fusing liposomes during interdigitation to produce the IF gels and liposomes of the present invention.

SUMMARY OF THE INVENTION

This invention provides a composition which comprises a sized liposome comprising a lipid; and an inducer, wherein the inducer is present in an amount effective to induce interdigitation-fusion of the liposome. The sized liposome typically has a diameter of less than about 0.4 microns, preferably, less than about 0.05 microns and most preferably, less than about 0.025 microns.

Preferably, the weight ratio of inducer to lipid is from about 1:10 to about 15:1. Preferably, the lipid is a saturated lipid; preferably, the saturated lipid is a symmetrical saturated phospholipid, e.g., dimyristoyl phosphatidylcholine, distearoyl phosphatidylcholine, dipalmitoyl phosphatidylcholine, dimyristoyl phosphatidylserine, dipalmitoyl phosphatidylserine, distearoyl phosphatidylserine, dimyristoyl phosphatidylethanolamine, dipalmitoyl phosphatidylethanolamine, distearoyl phosphatidylethanolamine, dimyristoyl phosphatidic acid, distearoyl phosphatidic acid, dipalmitoyl phosphatidic acid, hydrogenated soy phosphatidylcholine, distearoyl phosphatidylinositol, dipalmitoyl phosphatidylinositol, dipalmitoyl phosphatidylglycerol, di-O-hexadecyl phosphatidylcholine, distearoyl phosphatidylglycerol and dimyristoyl phosphatidylglycerol. The lipid can comprise an additional lipid, e.g., a lipid selected from the group consisting of saturated phospholipids, unsaturated phospholipids, glycolipids, glycosphingolipids, sterols and alpha-tocopherols.

The inducer can be a bioactive agent, e.g., a radiocontrast agent, NMR contrast agent, antimicrobial agent or peptide. Preferably, the bioactive agent is a radiocontrast agent, such as those selected from the group consisting of iohexol, iopamidol, ioxaglate, iotrolan, ioversol, iothalamate, iodipamide, iopromide, metrizamide, iopentol, iodixanol and diatrizoate. Preferably, the radiocontrast agent is iotrolan.

Also provided herein is an interdigitation-fusion gel comprising an interdigitated lipid and a bioactive agent. Preferably, the lipid is a symmetrical saturated phospholipid. In a preferred embodiment of the invention, the bioactive agent is an aminoglycoside antibiotic, such as those selected from the group consisting of neomycin B, paromomycin, ribostamycin, lividomycin, kanamycin A, kanamycin B, amikacin, tobramycin, gentamicin $C_1$, gentamicin $C_{1a}$, gentamicin $C_2$ netilmicin, or sisomicin. Typically, the weight ratio of bioactive agent to lipid is from about 1:10 to about 15:1.

Further provided herein is an interdigitation-fusion liposome which comprises a bioactive agent and an interdigitated lipid. Preferably, the interdigitated lipid is a symmetrical saturated phospholipid. Preferably, the bioactive agent is a radiocontrast agent, such as those selected from the group consisting of iohexol, iopamidol, ioxaglate, iotrolan, ioversol, iothalamate, iodamide, iodipamide, iopromide, metrizamide, iopentol, iodixanol and diatrizoate. More preferably, the radiocontrast agent is iotrolan. Typically, the weight ratio of bioactive agent to lipid is at least about 2:1.

This invention provides a method of producing an interdigitation-fusion gel which comprises incubating a sized liposome comprising a first lipid in the presence of an inducer, wherein the inducer is present in an amount effective to induce lipid interdigitation, and wherein the incubation is for a period of time sufficient for interdigitation. Preferably, the sized liposomes have a diameter of less than about 0.05 microns. Preferably, the first lipid is a symmetrical saturated phospholipid. Also provided is the interdigitation-fusion gel provided by this method.

This method can further comprise incubating the interdigitation-fusion gel at a temperature effective to induce a change in the materials properties of the gel, for a period of time sufficient to form an interdigitation-fusion liposome from the gel.

Preferably, the incubation temperature is greater than the transition temperature of the first lipid in the gel. Further provided is the interdigitation-fusion liposome produced by this method. Typically, the inducer is a bioactive agent, short-chain alcohol, polyol, aqueous buffer or chaotropic salt. Preferably, the inducer is a short chain alcohol, e.g., a short-chain alcohol selected from the group consisting of methanol, ethanol, propanol and n-butanol. More preferably, the inducer is ethanol. Typically, the effective amount of ethanol is an amount equal to from about 5% of the weight of the sized liposomes in the composition to about 20% of the weight of the sized liposomes; preferably, the effective amount of ethanol is an amount equal to about 7% of the weight of the liposomes in the composition.

In one embodiment of the invention, the method comprises adding a second lipid, for example, a non-interdigitating lipid, to the interdigitation-fusion gel prior to incubation. Preferably, the second lipid has a transition temperature in the gel less than the transition temperature of the first lipid in the gel. In one embodiment of this invention, the method further comprises adding a material, e.g., a bioactive agent, which interferes with lipid interdigitation to the interdigitation-fusion gel prior to incubation of the gel, so as to form an interdigitation-fusion liposome comprising the first lipid and the material.

This invention provides a method of preparing an interdigitation-fusion gel which comprises subjecting sized liposomes to an amount of hydrostatic pressure effective to interdigitate-fuse the sized liposomes for a period of time sufficient for interdigitation-fusion. Preferably, the sized liposomes have an average diameter of less than about 0.05 microns, and comprise a symmetrical saturated phospholipid. Typically, the amount of hydrostatic pressure is at least about 10,000 psi, preferably, at least about 20,000 psi, and more preferably, at least about 40,000 psi. The amount of hydrostatic pressure applied can be effective to sterilize the gel. Typically, the hydrostatic pressure is applied for a period of time of from about 1 minute to about 1 hour. Also provided is the interdigitation-fusion gel produced.

The method can further comprise incubating the interdigitation-fusion gel at a temperature effective to induce a change in the materials properties of the gel so as to form an interdigitation-fusion liposome from the gel. Preferably, the incubation temperature is greater than the transition temperature of the lipid in the gel. Also provided is the interdigitation-fusion liposome produced.

Also provided herein is a method of producing an interdigitation-fusion gel which comprises incubating sized liposomes comprising a self-inducing lipid. e.g., di-O-hexadecyl phosphatidylcholine, for a period of time sufficient for interdigitation-fusion. Preferably, the sized liposomes have an average diameter of less than about 0.5 microns. Typically, the sized liposomes are incubated for from about 1 minute to about 1 hour. Further provided is the interdigitation-fusion gel produced. The method can further comprise incubating the interdigitation-fusion gel at a temperature effective to change the materials properties of the gel, for a period of time sufficient for producing interdigitation-fusion liposomes from the gel. Preferably, the incubation temperature is greater than the transition temperature of the lipid in the gel. This invention provides the interdigitation-fusion liposome produced.

BRIEF DESCRIPTION OF THE DRAWINGS

FIG. 8. Graphically representation of the internal volume and encapsulation as a function of initial DPPC concentration, wherein

FIG. 10. Graphic representation of the effect of cholesterol on formation of DPPC. IF liposomes.

FIG. 11. Graphic representation of the effect of dioleoyl phosphatidylcholine (DOPC), an unsaturated lipid, on formation of IF liposomes.

DETAILED DESCRIPTION OF THE INVENTION

Figure 1A:
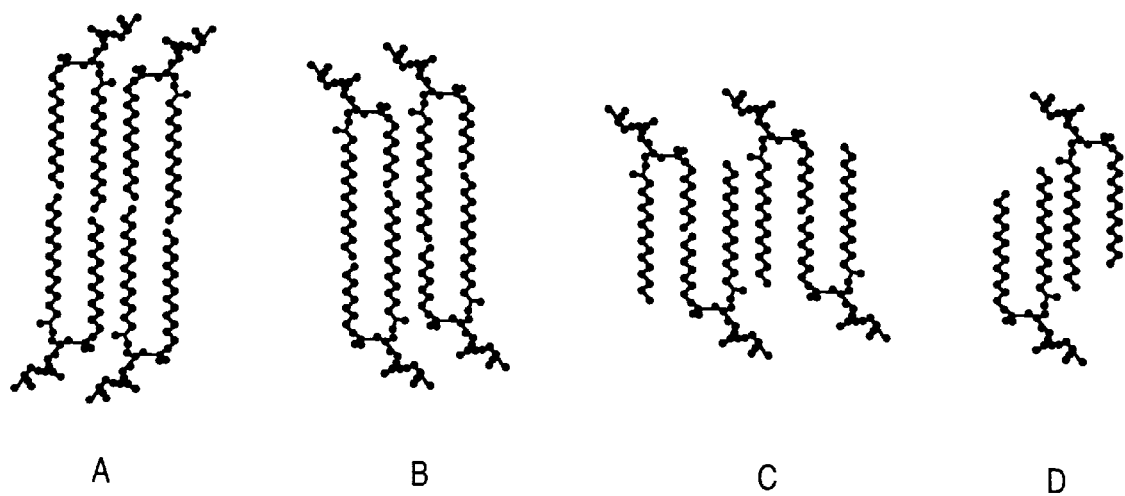
FIG. 1A. Schematic representation of the different acyl chain arrangements possible in bilayers. A represents a noninterdigitated bilayer comprising a phospholipid containing a symmetrical, saturated phospholipid C(16):C(16) phosphatidylcholine. B represents a partially interdigitated bilayer comprising an asymmetrical saturated phospholipid C(16):C(10)phosphatidylcholine. C represents a mixed interdigitated bilayer comprising C(16):C(10) phosphatidylcholine. D represents a fully interdigitated bilayer comprising C(16):C(1 6)phosphatidylcholine.
Figure 1B:
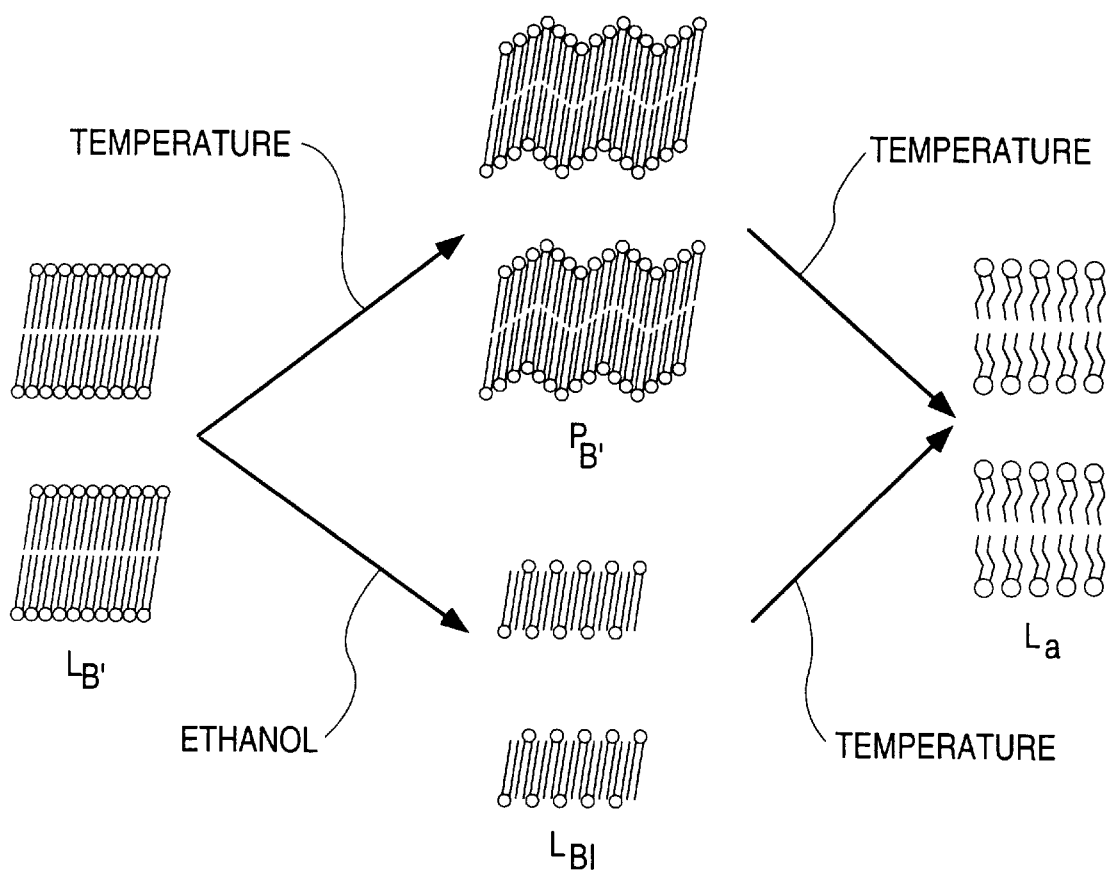
FIG. 1B. Schematic representation showing the effect of temperature and an inducer (ethanol) on the interdigitation of a saturated species of phospholipid.

For purposes of clarity, throughout the discussion of the present invention, the following definitions will be used: "Interdigitation" and "interdigitated" are used throughout the specification to describe the interactions of lipids in lipid bilayers in which the acyl chain region of a lipid in one monolayer of a lipid bilayer interpenetrates into the other monolayer of the lipid bilayer. The term interdigitation shall include full interdigitation, mixed interdigitation and partial interdigitation. Fully interdigitated lipids are those in which the acyl chains of a lipid in one monolayer of a bilayer interpenetrates fully across the width of the lipid bilayer as in FIG. 1A(D). Mixed interdigitated lipids are those asymmetric lipids in which the longer acyl chains extend completely across a lipid bilayer, while the shorter acyl chains meet end-to-end at about the bilayer midplane, as in FIG. 1A(C). Partially interdigitated lipids are those asymmetric lipids in which the longer and shorter acyl chains pair such that the longer acyl chain of a lipid in one monolayer of a bilayer pairs with the shorter acyl chain of a lipid in the bilayer's other monolayer, as in FIG. 1A(B). Individual lipid bilayers can have regions of fully, mixed and partially interdigitated lipids.

"Inducer" is used throughout the specification to describe molecules, such as amphipathic molecules of limited size, which localize at the lipid bilayer/aqueous phase interface and which shield the hydrophobic regions of interdigitated lipids from exposure to the aqueous phase. Inducers are generally chemical compounds, such as short-chain alcohols; furthermore, certain lipids can themselves induce liposome fusion and lipid interdigitation.

Hydrostatic pressure can also induce interdigitation-fusion. "Pressure induced fusion" ("PIF") is interdigitation induced by application of an amount of hydrostatic pressure to sized liposomes that is effective to form an interdigitation fusion gel from the sized liposomes. Liposomes formed from this gel are referred to herein as PIF liposomes, or simply PIFs.

"Interdigitation-fusion gel (IF gel)" is used throughout the specification to describe the product that results when an inducer is combined in sufficient quantity with sized liposomes to fuse the liposomes such that lipids contained therein are interdigitated. Interdigitated lipid bilayers in IF gels are generally thinner than bilayers comprised of the same lipid, but not subject to interdigitation-fusion. Bilayer thickness can be measured by a number of methods well known to, and readily practiced by, ordinarily skilled artisans, such as x-ray diffraction. The resulting sheets of lipid are fused gels for purposes of the present invention, and may include products of varying viscosity including liquids, gels and in certain cases, even very viscous products approaching the solid state.

"Interdigitation-fusion liposome (IF liposome)" is used throughout the specification to describe the liposomes produced from IF gels, when the gels are incubated at a temperature effective to change the fluidity of the IF gel such that a liposome is produced from the gel.

"Interdigitated-fused lipid-containing composition" is used herein to describe compositions containing interdigitated lipids.

"Bioactive agent" is used throughout the specification to describe agents, such as therapeutic, diagnostic and imaging agents, which exhibit biological activity, and which can be administered to living organisms, especially humans. Bioactive agents include, but are not limited to: vitamins, hormones, antimetabolites and antimicrobial agents, such as antifungal agents, including polyene antifungals, antibacterial agents, including aminoglycosides, antiviral agents and antiparasitic agents. Bioactive agents also include proteins, peptides, ribo- and deoxyribonucleic acids, nucleotides, nucleosides, oligonucleotides, antihistaminic agents and neuropharmacologic agents, including sedatives. Bioactive agents further include steroidal and nonsteroidal antiinflammatory agents, diuretic agents, antihypertensive agents. antiarrhythmic agents, immunogens, immunomodulators, contraceptive agents, antiviral agents, vascular dilating agents, salicylic acid, resorcinol, phenol, retinoic acid, benzodiazepines, antipyretic agents, antispasmodics, antipruritic agents, sympathomimetics, decongestants, tranquilizers, antispasmodics, anti-emetics, sedatives and hypnotics, steroidal agents, progestational agents, local anesthetics and desensitizing agents, for example antigens and vaccines. Bioactive agents include vitamins, nutrients, such as amino acids, essential fats and minerals, retinoids and anti-neoplastic agents, including the anthracyclines and certain alkylating agents. Bioactive agents also include radiocontrast agents, such as the iodinated radiocontrast agents, for example, iotrolan, NMR contrast agents, radioisotopes, radiolabels and dyes. The above-listed group of bioactive agents, among other agents, including their pharmaceutically acceptable salts, are contemplated for use in the present invention. Determination of compatibilities of the above listed agents with, and the amounts to be utilized in, compositions of the present invention are within the purview of the ordinarily skilled artisan to determine given the teachings of this invention.

"Saturated lipid" is used throughout the specification to describe a lipid that may be used to produce the interdigitation-fusion gels and liposomes of the present invention, and includes lipids, such as phospholipids, having symmetrical and/or asymmetrical acyl side chains which contain no double bonds between carbon atoms. Saturated lipids include, but are not limited to: dimyristoyl phosphatidylcholine, distearoyl phosphatidylcholine, dipalmitoyl phosphatidylcholine, dimyristoyl phosphatidylserine, dipalmitoyl phosphatidylserine, distearoyl phosphatidylserine, dimyristoyl phosphatidylethanolamine, dipalmitoyl phosphatidylethanolamine, distearoyl phosphatidylethanolamine, dimyristoyl phosphatidic acid, distearoyl phosphotidic acid, dipalmitoyl phosphatidic acid, dimyristoyl phosphatidylinositol, distearoyl phosphatidylinositol, dipalmitoyl phosphatidylinositol, dipalmitoyl phosphatidylglycerol, di-O-hexadecyl phosphatidylcholine, distearoyl phosphatidylglycerol and dimyristoyl phosphatidylglycerol. Suitable saturated lipids also include asymmetrical saturated lipids, that is, lipids which have fatty acid chains of unequal length, or number of carbon atoms.

This invention provides a composition which comprises a sized liposome comprising a lipid; and an inducer, wherein the inducer is present in an amount effective to induce interdigitation-fusion of the liposome. The sized liposome typically has a diameter of less than about 0.4 microns, preferably, less than about 0.05 microns and most preferably, less than about 0.025 microns. Preferably, the weight ratio of inducer to lipid is from about 1:10 to about 15:1. The sized liposomes used herein are preferably formed from saturated phospholipids. Most preferably, the saturated phospholipids are symmetrical that is, they have two acyl chains of equal length, or number of carbon atoms. The liposomes subjected to sizing can be unilamellar or multilamellar liposomes, and can be produced by techniques well known to, and presently available in, the art. Typically, liposomes can initially be is prepared by vacuum drying a solution of lipid in organic solvent, for example, chloroform, to a thin film in a round bottom or other suitable flask or vessel, followed by hydration of the lipid film with an aqueous solvent such as for example, aqueous buffer or saline solution. Alternatively, liposomes can be formed from admixture of dry lipid powder and aqueous solvent, preferably for example saline solution or aqueous buffer.

A liposome's "size" is typically referred to in terms of its diameter, and can be measured by a number of techniques well known to ordinarily skilled artisans, such as quasi-electric light scattering. Typically, the sized liposome has a diameter of at most about 1.0 micron, preferably at most about 0.4 microns, more preferably, at most about 0.1 microns and still more preferably, at most about 0.05 microns. Most preferably, the sized liposome has a diameter of about 0.025 microns.

Liposomes sizing can be accomplished by a number of methods, such as extrusion, sonication and homogenization techniques which are well known, and readily practiced, by ordinarily skilled artisans. Extrusion involves passing liposomes, under pressure, one or more times through filters having defined pore sizes. Generally, the filters have pore sizes generally ranging from about 30 nm to about 1 micron to produce liposomes ranging in size from about 30 nm to about 1 micron in diameter. Preferably, the pore size of the filters through which the liposomes may be extruded ranges from about 100 nm to about 1 micron, more preferably, from about 50 nm to about 100 nm. The filters are generally made of polycarbonate, but the filters may be made of any durable material which does not interact with the liposomes and which is sufficiently strong to allow extrusion under sufficient pressure. Preferred filters include "straight through" filters because they generally can withstand the higher pressure of the preferred extrusion processes of the present invention. "Tortuous path" filters may also be used. In the preferred embodiments of the present invention, sized liposomes are extruded through 50 to 100 nm polycarbonate filters to produce liposomes having a diameter of about 50 to 100 nm. Extrusion can also use asymmetric filters, such as Anotec® filters (see Loughrey et al., U.S. Pat. No. 5,059,421), which involves extruding liposomes through a branched-pore type aluminum oxide porous filter.

Liposomes can also be size reduced by sonication, which employs sonic energy to disrupt or shear liposomes, which will spontaneously reform into smaller liposomes. Sonication is conducted by immersing a glass tube containing the liposome suspension into the sonic epicenter produced in a bath-type sonicator. Alternatively, a probe type sonicator may be used in which the sonic energy is generated by vibration of a titanium probe in direct contact with the liposome suspension. Homogenization and milling apparatii, such as the Gifford Wood homogenizer, Polytron™ or Microfluidizer™, can also be used to break down larger liposomes into smaller liposomes. A number of other techniques may be used for producing sized liposomes which are to undergo interdigitation-fusion, and for producing sized IF liposomes after the process is complete.

The resulting liposomes can be separated into homogeneous populations using methods well known in the art; such as tangential flow filtration (see WO 89/00846). In this procedure, a heterogeneously sized population of liposomes is passed through tangential flow filters, thereby resulting in a liposome population with an upper and/or lower size limit. When two filters of differing sizes, that is, having different pore diameters, are employed, liposomes smaller than the first pore diameter pass through the filter. This filtrate can the be subject to tangential flow filtration through a second filter, having a smaller pore size than the first filter. The retentate of this filter is a liposome population having upper and lower size limits defined by the pore sizes of the first and second filters, respectively.

After the formation of sized liposomes, substances to be entrapped in the liposomes, preferably one or more bioactive agents, can be added. In the case where the bioactive agent does not interact with the liposomes, it can be mixed in with the aqueous or aqueous/buffer solvent after formation of the sized liposomes which are to undergo interdigitation. In the case of a bioactive agent that interacts with the liposomes, the agent is generally mixed in with the aqueous solvent after the formation of interdigitation-fusion gels. Of course, one of ordinary skill in the art will recognize that the order in which the individual components of the IF gels and liposomes of the present invention are added may vary, and is dependent on the type of agent to be entrapped and the type of saturated lipid utilized.

Exemplary interdigitation inducers for use in the present invention include, for example, short chain alcohols including methanol, ethanol, propanol, isopropanol and n-butanol, polyols such as glycerol and ethylene glycol, buffers such as Tris, chaotropic salts such as thiocyanate and bioactive agents, including the anaesthetics chlorpromazine, tetracaine, phenylethanol, benzyl alcohol and phenylbutanol, and bioactive agents, such as radiocontrast agents.

In general, the amount of inducer used comprises about 1.0% to about 50% of the total weight of solution, which includes a combination of the sized liposomes and the inducer. However, within this range, the concentration of inducer can be varied according to a number of factors, for example, the type and composition of the liposome to be sized, that are well within the purview of the ordinarily skilled artisan to determine given the teachings of this invention. In general, the weight ratio of bioactive agent to lipid in the aqueous solvent will range from about 50:1 to about 1:100, with the final concentration of lipid falling within the range of about 5 to 100 mM. The final weight ratio of bioactive agent to lipid in the interdigitation-fusion gels and liposomes of the present invention ranges from about 1:10 to about 15:1. Where ethanol is used as the inducer, the amount of ethanol included is generally about 5% by weight (1.0 M) to about 20% by weight (4.0 M), that is, a weight ratio typically of from about 1:20 to about 1:4 (inducer: lipid), preferably, about 1:7; in the case of glycerol the amount of inducer utilized may be as much as about 90–100% by weight. The amount of other inducers to be included will vary.

Figure 3:
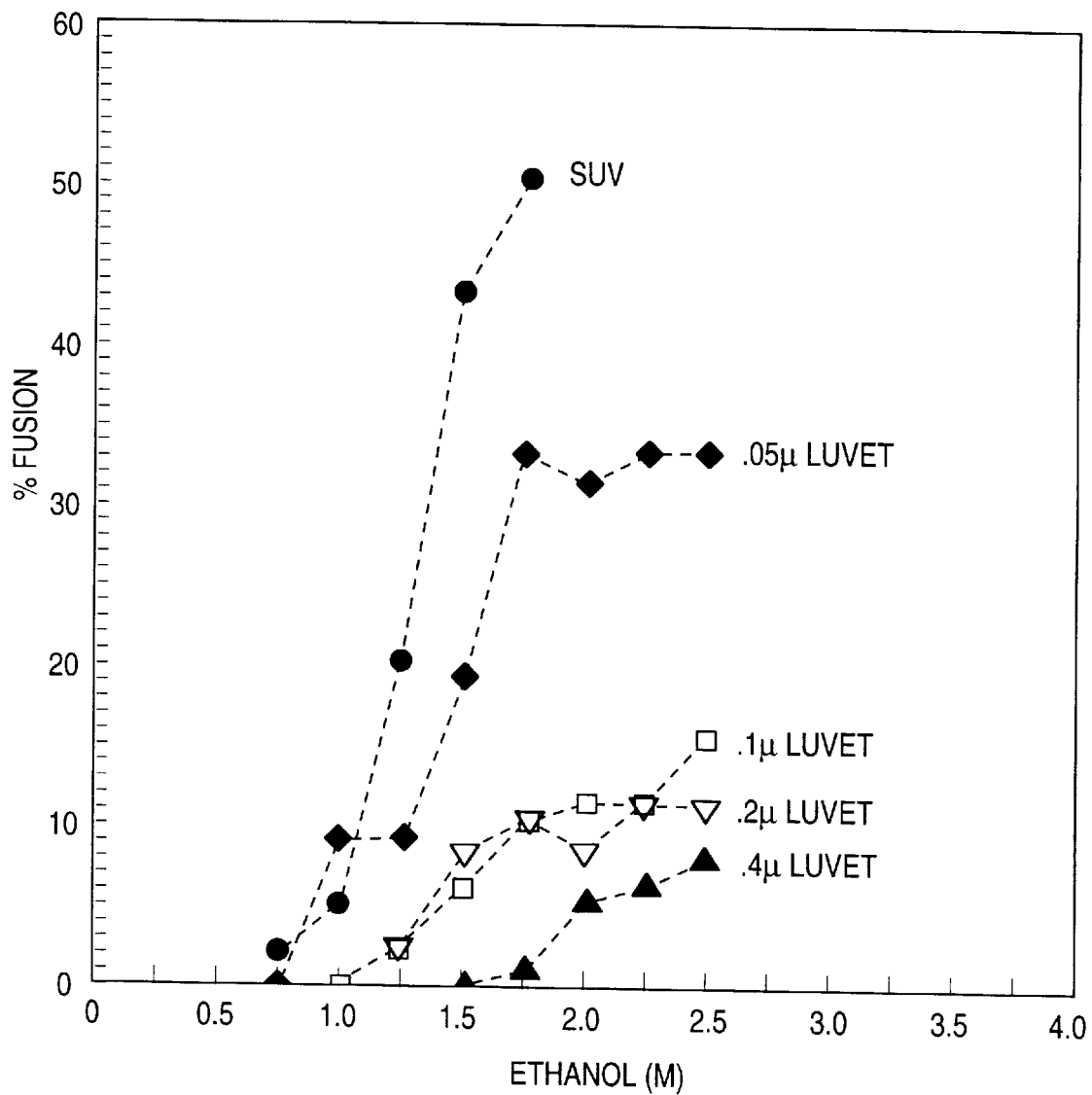
FIG. 3. Lipid mixing of DPPC liposomes as a function of size and ethanol concentration as judged by resonance energy transfer (RET) between NBD-PE and rhodamine-PE incorporated together in a marker population of liposomes.

Also provided herein is an interdigitation-fusion gel comprising an interdigitated lipid and a bioactive agent. Preferably, the lipid is a symmetrical saturated phospholipid. The presence of an inducer in an effective amount will cause sized liposomes comprising such lipids to fuse, resulting in the formation of sheets of interdigitated lipid. While not being limited by way of theory, it is believed that sized liposomes fuse into lipid sheets (gels) at certain concentrations of inducer in order to relieve bilayer strain imposed by the liposomes' small radius of curvature (see, for example, FIG. 3). The resulting interdigitation-fusion gel that is produced may capture a high concentration of bioactive agent. The IF gel of this invention can be used topically or for oral administration, for example, as formulations encapsulated in soft gelatin or other oral dosage forms. In a preferred embodiment of the invention, the topically or orally applied IF gel contains an aminoglycoside antibiotic, such as those selected from the group consisting of neomycin B, paromomycin, ribostamycin, lividomycin, kanamycin A, kanamycin B, amikacin, tobramycin, gentamicin $C_1$, gentamicin $C_{1a}$, gentamicin $C_2$ netilmicin, or sisomicin. Typically, the weight ratio of bioactive agent to lipid in the IF gel is from about 1:10 to about 15:1.

The IF gel may be further modified to produce the interdigitation-fusion liposome of this invention comprising a bioactive agent, wherein the weight ratio of bioactive agent to lipid in the liposome is from about 1:10 to about 15:1. Preferably, the weight ratio is at least about 2:1. According to this invention, IF liposomes are formed from IF gels when the fluidity of the gels is changed such that a fluid phase lipid bilayer is formed from the gel phase interdigitated bilayer. The interdigitated bilayer generally passes, from the gel phase to the fluid phase when the IF gel is incubated at a temperature above the transition temperatures ("Tm") of the component lipids of the gel. Subsequent to liposome formation from IF gels, the inducer is then preferably (but not necessarily) removed. Interdigitation is believed to render the lipid bilayer less susceptible to perturbation during liposome formation, and can be utilized in connection with liposome formation to capture substances which normally interact with membranes and are difficult to entrap. IF liposomes also have higher captured volume efficiencies, that is, the ratio of volume of the aqueous phase entrapped in the liposome to the weight of lipid in the liposomes, than other known liposomes, Accordingly, interdigitation-fusion liposomes can be used to entrap high concentrations of bioactive agents, including iodinated radiocontrast agents and aminoglycosides, aminoglycosides being difficult to entrap in liposomes at high concentrations because of their tendency to interact with membranes. IF liposomes have been shown to entrap gentamicin at a drug/lipid ratio of about 1:2 (w:w), whereas liposomes such as stable plurilamellar liposomes (SPLVs) entrap gentamicin at a drug/lipid ratio of about 1:10 (w:w). IF liposomes can entrap iodinated radiocontrast agents such as iotrolan at weight ratios of iodine to lipid in the liposomes of at least 2:1.

The IF liposomes may vary in size as a function of the lipid, liposome and inducer utilized, but generally, will range in size from about 100 μm, and more preferably about 20 microns, to about 0.025 microns; the IF liposomes can then be size reduced according to methods known in the art.

The interdigitation-fusion liposomes of this invention can be dehydrated, and then stored and reconstituted on an as-needed basis. Liposomes can be dehydrated, with freezing, using standard freeze-drying equipment, or its equivalents. Lyophilization is preferably carried out after incorporating one or more protective hydrophilic compounds, such as, but not limited to, sugars, into liposome preparations in accordance with the procedures described in Schneider et al. (U.S. Pat. No. 4,229,360) and Janoff et al., (U.S. Pat. No. 4,880,635). The protective sugar can be omitted if the dehydration is conducted without freezing and sufficient water is left remaining in the liposomal preparation to maintain the integrity of a substantial portion of the liposomal bilayers through the dehydration-rehydration process.

This invention provides a method of producing an interdigitation-fusion gel which comprises incubating a sized liposome comprising a first lipid in the presence of an inducer, wherein the inducer is present in an amount effective to induce lipid interdigitation, and wherein the incubation is for a period of time sufficient for interdigitation. Most preferably, the sized liposomes have a diameter of less than about 0.05 microns. Preferably, the first lipid is a symmetrical saturated phospholipid. Also provided is the interdigitation-fusion gel provided by this method.

This method can further comprise incubating the interdigitation-fusion gel at a temperature effective to induce a change in the fluidity of the gel such that an interdigitation-fusion liposome is formed from the gel. The incubation is for a period of time effective for the fluidity change, and is at a temperature generally, but not necessarily, above the gel-liquid transition temperature of the gel. While maintaining this incubation temperature, the inducer may be removed by evaporation (especially in the case of alcohol inducers), positive pressure nitrogen (e.g., $N_2$ sparge consisting generally of bubbling $N_2$ through the mixture) or by dilution. This produces IF liposomes varying in size generally between about 0.025 and about 100 μm. Unencapsulated bioactive agent can be removed from the solvent, if desired, Typically, the inducer is a bioactive agent, short-chain alcohol, polyol, aqueous buffer or chaotropic salt. Preferably, the inducer is a short chain alcohol, e.g., a short-chain alcohol selected from the group consisting of methanol, ethanol, propanol and n-butanol. However, other inducers that produce an IF gel from sized liposomes can be used in accordance with this invention.

More preferably, the inducer is ethanol. Typically, the effective amount of ethanol is an amount equal to about 5% of the weight of the sized liposomes in the composition to about 20% of the weight of the sized liposomes; preferably, the effective amount of ethanol is an amount equal to about 7% of the weight of the liposomes in the composition.

In one embodiment of the invention, the method comprises adding additional material to the IF gel after its formation and prior to incubation to form IF liposomes. Aqueous-soluble compounds, such as bioactive agents, and lipid-soluble compounds, such as lipids and bioactive agents, can be added to the IF gel. Adding materials to IF gels after their formation is preferentially carried out for compounds which tend to interfere with interdigitation-fusion and which are not desirably part of the sized liposomes subject to interdigitation-fusion. Such compounds include non-interdigitating lipids, that is, lipids such as unsaturated lipids, mixed chain (saturated/unsaturated) lipids, such as SOPC and POPC, sterols and alpha-tocopherols which generally do not undergo interdigitation. Compounds added to IF gels after their formation can also include lipids which do undergo interdigitation-fusion. The compound can be an additional lipid such as transdielaidoyl phosphatidylcholine, dipalmitelaidoyl phosphatidylcholine, a lysolipid, for example, n-octadecyl-2-methylphosphatidylcholine, 1-laurylpropanediol-3-phosphocholine and erythro-N-lignoceroyl sphingophosphatidylcholine, a sphingolipid or a glycosphingolipid. It is generally preferred that when DOPC is employed, it be used with the saturated lipid DPPC, in no more than a proportion of 50 mole percent unsaturated lipid. One of ordinary skill in the art will recognize that the amount and type of additional lipid which may be included in compositions of the present invention may be varied within the teachings of the present application. Preferably, when the compound added to the IF gel is an additional lipid, this additional lipid has a transition temperature in the gel less than the transition temperature of the first lipid in the gel.

This invention provides a method of preparing an interdigitation-fusion gel which comprises subjecting sized liposomes to an amount of hydrostatic pressure effective to interdigitate-fuse the sized liposomes for a period of time sufficient for interdigitation-fusion. Most preferably, the sized liposomes have an average diameter of less than about 0.05 microns, and comprise a symmetrical saturated phospholipid. Typically, the amount of hydrostatic pressure is at least about 10,000 psi, preferably, at least about 20,000 psi, and more preferably, at least about 40,000 psi. Typically, the hydrostatic pressure is applied for a period of time of from about 1 minute to about 1 hour. Also provided is the interdigitation-fusion gel produced.

For example, unilamellar liposomes having diameters of less than about 50 nm, and comprising DPPC or DSPC, were fused to form larger liposomes by the application of pressure of at least 20,000 psi, and preferably at least 40,000 psi, for a period of about 15 minutes. Although DPPC and DSPC were successfully interdigitated by pressure induced fusion (PIF), the PIF process was found not to induce interdigitation on small liposomes of palmitoyloleoyl phosphatidylcholine (POPC), which has an unsaturated acyl chain.

Figure 15:
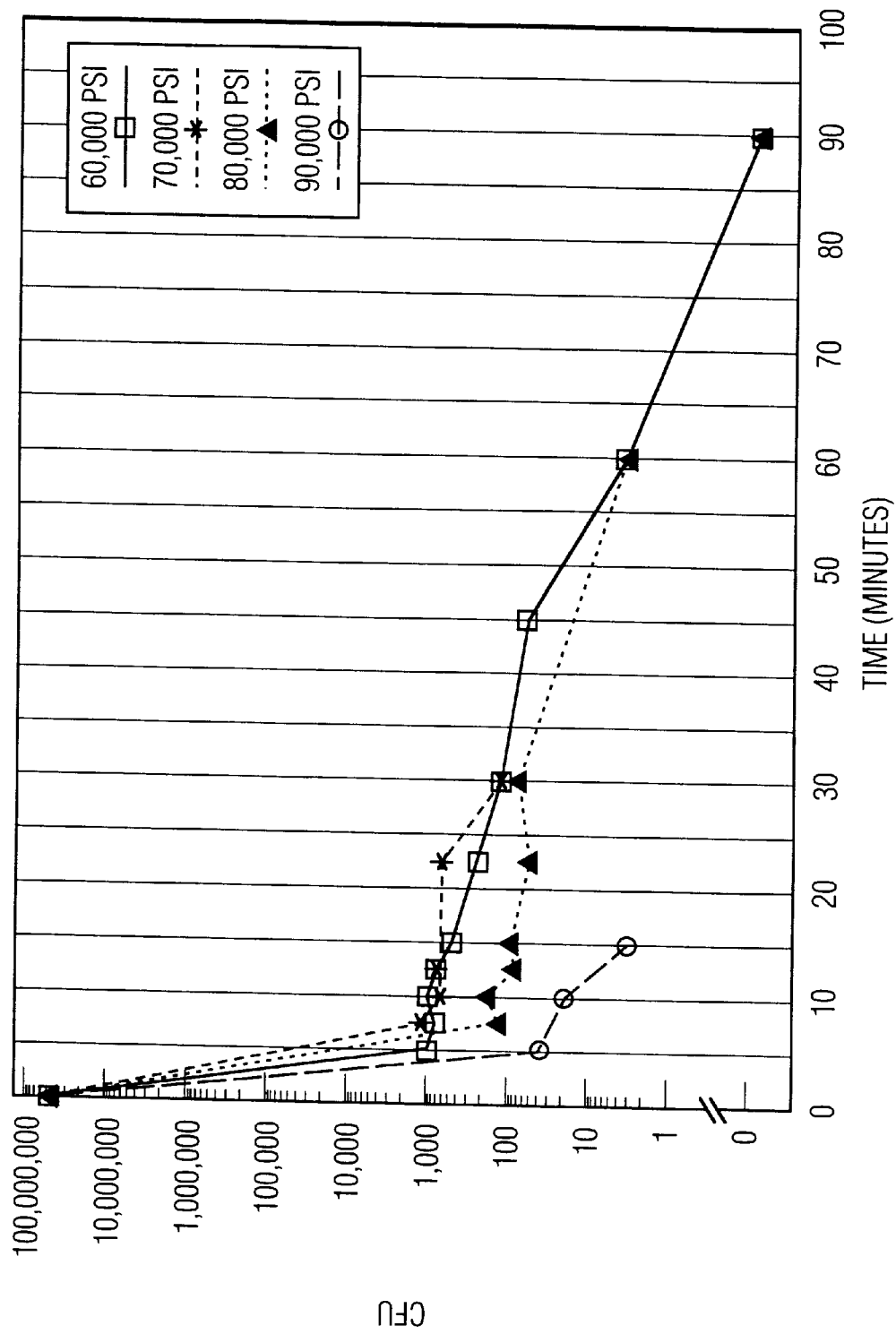
FIG. 15. Graph showing the effect of pressure sterilization on bacteria at 40° C.
Figure 16:
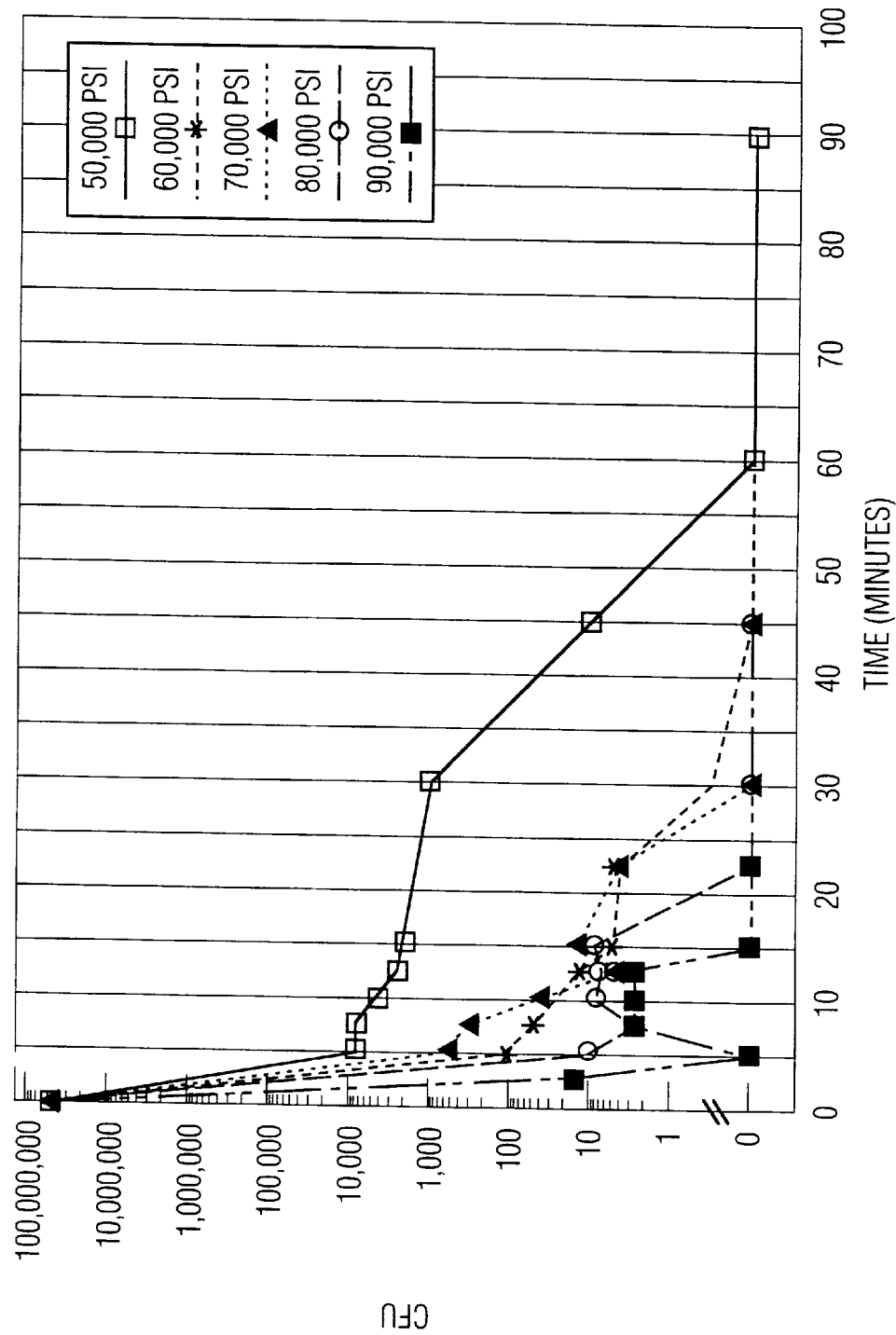
FIG. 16. Graph showing the effect of pressure sterilization on bacteria at 50° C.
Figure 17:
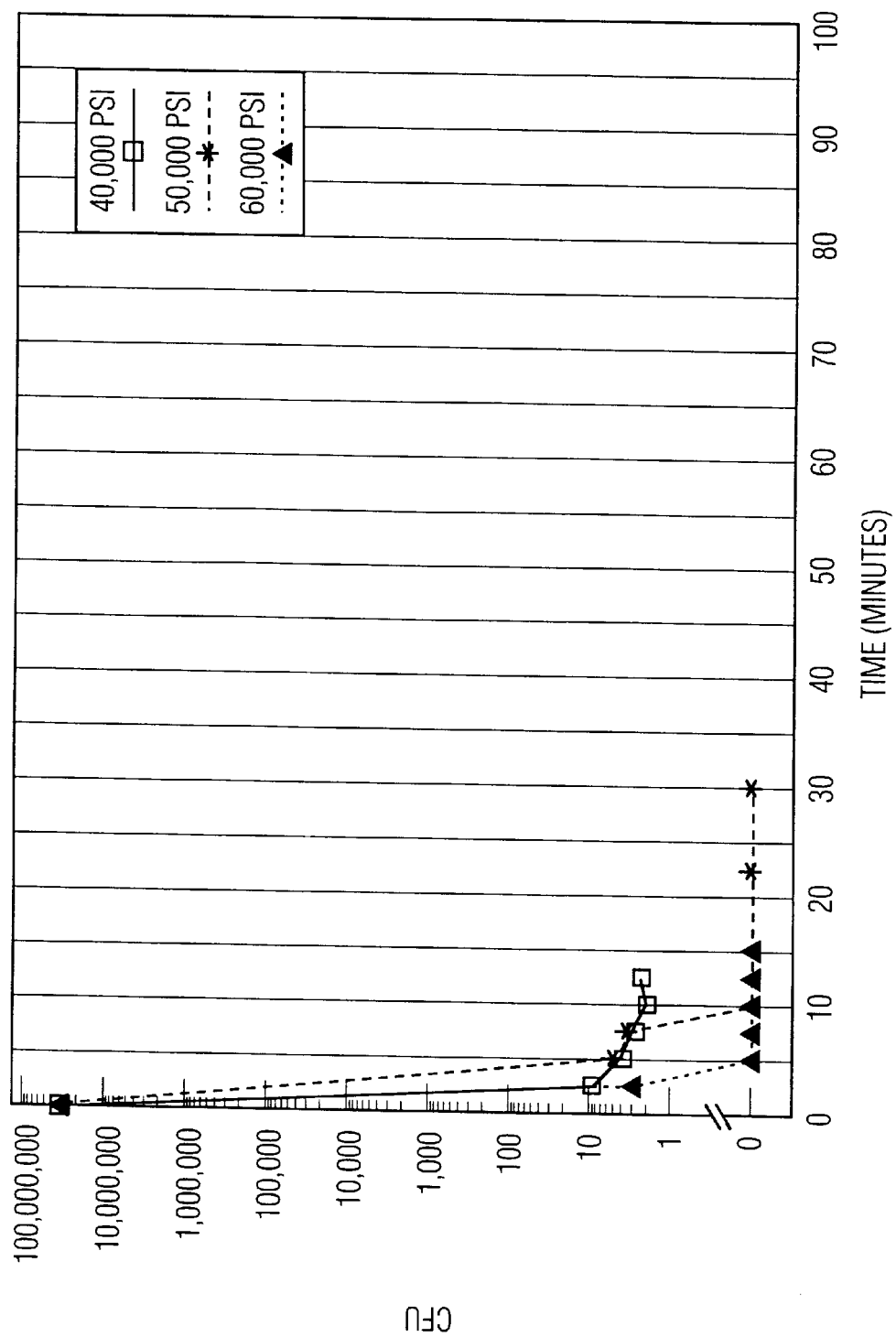
FIG. 17. Graph showing the effect of pressure sterilization on bacteria at 60° C.

The amount of hydrostatic pressure applied can be effective to sterilize the gel. Hydrostatic pressures are known to have effects on cellular processes. Currently, high pressure and moderate temperature is used for the pasteurization and sterilization of certain food products. Such methods generally employ the application of pressures as high as 75,000 psi and moderate temperatures. Bacteria, yeast and viruses may all be inactivated by the application of high pressure. The inactivation process, given a fixed pressure, is known to vary as a function of temperature, chemical composition of the medium, and time. In accordance with the present invention, high hydrostatic pressures and moderate temperatures are used to kill microbes, including bacteria such as *Bacillus subtilis* in Example 28 below, and thereby to sterilize liposomal preparations. *Bacillus subtilis* was chosen for use in this example because it is considered one of the most difficult microbes to kill in sterilization processes. In Example 28, the rate of inactivation for several temperatures at a number of pressures is described. As can be seen from the results presented in FIGS. 15, 16 and 17, the rate of sterilization is a function of the temperature and pressure at which the sterilization is performed. In general, in performing the sterilization process of the present invention on a selected liposomal composition in the shortest time, one would determine a suitable temperature and pressure effective for composition. For the most rapid sterilization, one would use a combination of the highest temperature and pressure which can be tolerated by the liposomal composition. The data presented in FIGS. 15, 16 and 17 provide an example of the relationship between temperature and pressure for such sterilizing processes.

A pressure of about 10,000 psi is considered to be a minimum level for effecting sterilization in accordance with the present invention. Preferably, a minimum of about 40,000 psi pressure is used to carry out the sterilization more rapidly, the actual time required being dependent on the temperature under which the process is performed. The pressure should be kept below a level which can have a deleterious effect on the particular liposome composition being sterilized. In like manner the maximum temperature should also be below that which causes deleterious effects to the liposome composition, such as structural or chemical changes to the liposomes or to any of the components of the composition.

The method can further comprise incubating the interdigitation-fusion gel at a temperature effective to induce a change in the fluidity of the gel so as to form an interdigitation-fusion liposome from the gel. Preferably, the incubation temperature is greater than the transition temperature of the lipid in the gel. Also provided is the interdigitation-fusion liposome produced.

Also provided herein is a method of producing an interdigitation-fusion gel which comprises incubating sized liposomes comprising a self-inducing lipid, e.g., di-O-hexadecyl phosphatidylcholine, for a period of time sufficient for interdigitation-fusion. A "self-inducing" lipid is a lipid which can induce lipids to interdigitate, and sized liposomes to fuse, in the absence of other inducers. Self-inducing lipids can be identified by forming sized liposomes comprising the lipid and incubating the sized liposomes, preferably at a temperature greater than the gel-to-liquid transition temperature of the lipid, for a period of time generally sufficient for interdigitation-fusion, and in the absence of an exogenous interdigitation-fusion inducer. Liposomes comprising lipids capable of self-induction will generally undergo interdigitation-fusion in such conditions. Interdigitation-fusion can be determined by measuring bilayer thickness and comparing this thickness to bilayers comprised of the same lipid which were not subject to interdigitation-fusion conditions. Interdigitated bilayers are generally thinner than noninterdigitated bilayers. Bilayer thickness can be measured by a number of means well known to, and readily practiced by ordinarily skilled artisans, such as x-ray diffraction measurements. Preferably, the sized liposomes have an average diameter of less than about 0.5 microns. Typically, the sized liposomes are incubated for from about 1 minute to about 1 hour.

Further provided is the interdigitation-fusion gel produced. The method can further comprise incubating the interdigitation-fusion gel at a temperature effective to change the materials properties of the gel, for a period of time sufficient for producing interdigitation-fusion liposomes from the gel. Preferably, the incubation temperature is greater than the transition temperature of the lipid in the gel. This invention provides the interdigitation-fusion liposome produced.

The IF liposomes and gels of the present invention may be administered to animals, including mammals such as humans. Accordingly, as the IF gels and liposomes provided herein can contain a bioactive agent, this invention provides a method of administering a bioactive agent to an animal which comprises administering to the animal, e.g., a human, an interdigitation-fusion liposome or gel comprising the bioactive agent. Preferably, an interdigitation-fusion liposome comprising the iodinated radiocontrast agent iotrolan, is administered.

For administration to humans in the treatment of afflictions, the prescribing physician will ultimately determine the appropriate dose for a given subject, and this can be expected to vary according to the age, weight, and response of the individual as well as the nature and severity of the patient's symptoms. It will be appreciated that the actual preferred amounts of bioactive agent utilized in a specific case may vary according to the severity of a pharmacological or disease condition and the expected pharmacokinetics of bioactive agent in the individual patient. Dosages for a given host can be determined using conventional considerations, e.g., by customary comparison of the differential activities of the subject bioactive agent by means of an appropriate, conventional pharmacological protocol.

The mode of administration of compositions of the present invention may determine the sites in the organism to which the compositions will be delivered. For instance, delivery to a specific site of infection may be most easily accomplished by topical application (if the infection is external, e.g., on areas such as the eyes, skin, in the ears or on afflictions such as wound or burns) or by absorption through epithelial or mucocutaneous linings (e.g., nasal, oral, vaginal, rectal, gastrointestinal, mucosa, etc.). Such topical application may be in the form of creams or ointments. The interdigitation-fusion gels of the present invention are preferably used topically. However, the IF gels of the present invention may be used orally in formulations in which the lipid, upon contacting the fluids of the mouth or gastrointestinal tract forms a liposome in situ.

The IF gels and liposomes containing a bioactive agent may be administered alone, but will generally be administered in admixture with a pharmaceutical carrier selected with regard to the intended route of administration and standard pharmaceutical practice. The IF liposomes of the present invention may be injected parenterally, for example, intravenously, intramuscularly, or subcutaneously. For parenteral administration, these liposomes are best used in the form of a sterile aqueous solution which may contain other solutes, for example, sufficient salts, glucose or dextrose to make the solution isotonic. Such solutions include physiological saline and D5W, a 5% weight-by-volume solution of dextrose in water. For the oral mode of administration, the liposomes of the present invention can be used in the form of tablets, capsules, lozenges, troches, powders, syrups, elixirs, aqueous solutions and suspension, and the like. In the case of tablets, carriers which can be used include lactose, sodium citrate, and salts of phosphoric acid. Various disintegrants such as starch, and lubricating agents may be used. For oral administration in capsule form, useful diluents are lactose and high molecular weight polyethylene glycols. When aqueous suspensions are required for oral use, certain sweetening and/or flavoring agents can be added.

The following examples are provided to illustrate the present invention and should not be construed to limit the scope of the invention of the present application, as defined in the claims which follow thereafter, in any way.

EXAMPLES

Example 1

Liposomes comprising dipalmitoyl phosphatidylcholine (DPPC, obtained from Avanti Polar Lipids, Birmingham, Ala., USA) were formed in 1 ml of an aqueous buffer solution to a concentration of 20 mM DPPC and additionally containing 0.04 mM diphenyl hexatriene (DPH, purchased from Molecular Probes, Eugene, Oreg., USA). After formation of the liposomes, ethanol was added to a final concentration of 0.3 M to 2.5 M of the aqueous solution.

Figure 2:
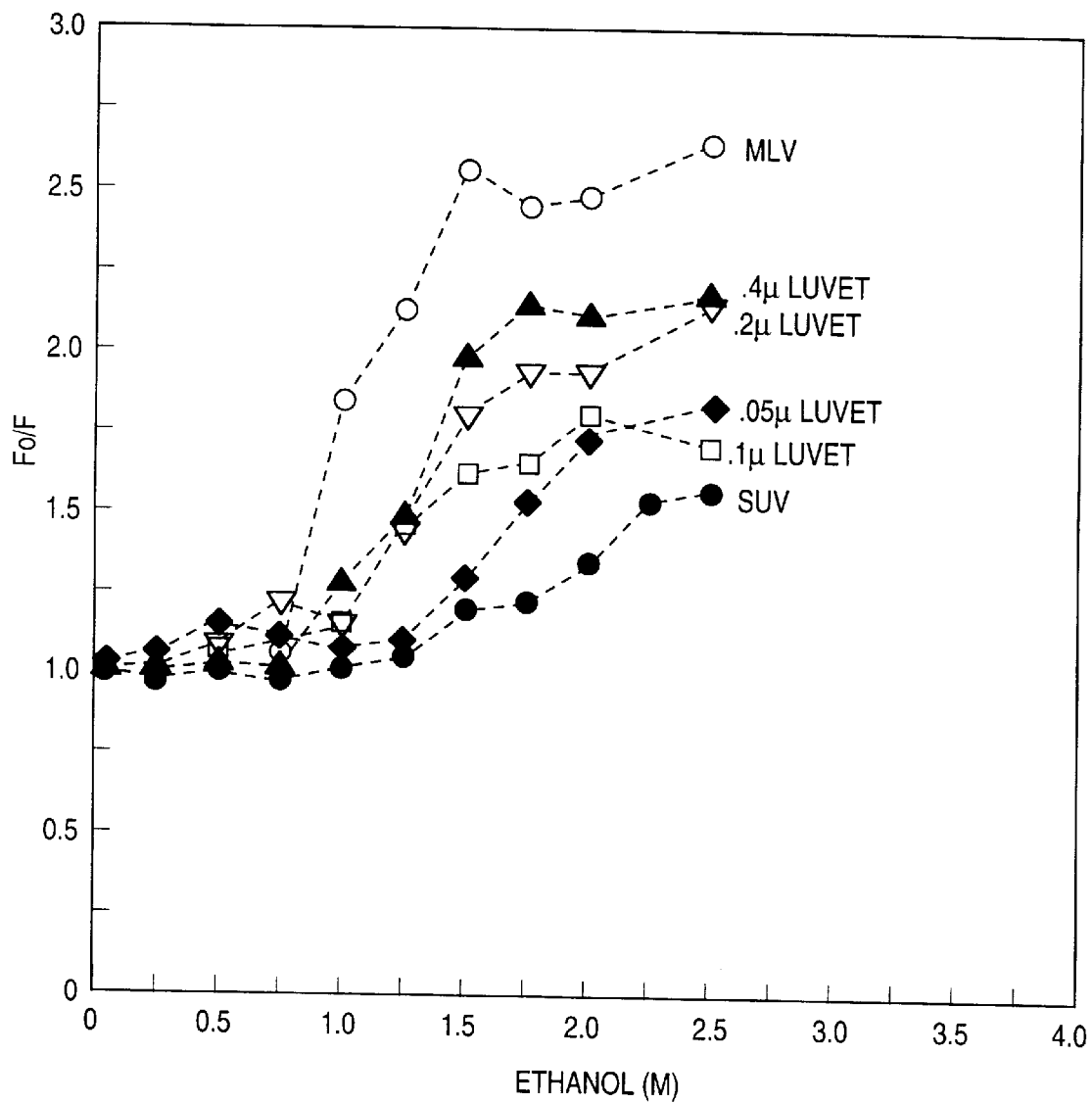
FIG. 2. Interdigitation of dipalmitoyl phosphatidylcholine (DPPC) liposomes as a function of the initial size of the liposomes and the concentration of ethanol. Fo=DPH fluorescence in the absence of ethanol. F=DPH fluorescence in the presence of ethanol. Excitation=351 nm. Emission was detected between 380 and 580 nm and quantitated by weighing.

DPH fluoresces maximally when incorporated into the liposome bilayer. Interdigitation results in the reorientation of DPH from the bilayer membrane with a concomitant decrease of fluorescence. As shown in FIG. 2, interdigitation is greater where higher concentrations of ethanol are present, for all liposomes. The effect of interdigitation by the same amount of ethanol is greater in those liposomes having a larger diameter. In FIG. 2, Fo=DPH fluorescence in the absence of ethanol; F=DPH fluorescence in the presence of ethanol. Excitation=351 nm. Emission was detected between 380 and 580 nm and quantitated by weighing.

Example 2

Lipid Mixing of Liposomes

Lipid mixing of sized DPPC Liposomes was determined as a function of the size of the Liposomes and concentration of inducer. Liposomes comprising DPPC were formed in an aqueous buffer solution containing 20 mM DPPC. A marker population of liposomes containing 99% by weight DPPC, 0.35% by weight N-benzyldiphosphatidyl ethanolamine (NBD-PE) and 0.65% by weight rhodamine-phosphatidylethanolamine were formed in 1 ml. of an aqueous buffer solution. These probes form a donor-acceptor pair. The NBD moiety is excited at 465 nm and via resonance energy transfer (RET) becomes quenched by the rhodamine acceptor which itself becomes excited in a distance dependent phenomenon. These liposomes were mixed with blank liposomes at a 1:10 ratio. Emission spectra were recorded between 480 and 680 nm. Lipid mixing in DPPC liposomes of varying size as a function of ethanol concentration can be determined by the loss of RET from the NBD moiety to the Rhodamine moiety. A standard curve was generated by preparing liposomes of 0.35 mole percent NBD-PE and 0.65 mole percent Rhodamine-PE with sequentially decreasing these mole percents to 0.035 and 0.065 respectively. A direct comparison from the 1/10 mixing experiments with this standard curve indicates the degree of lipid mixing, an indication of membrane fusion.

Example 3

Comparison of Trapped Solute in Various Vesicle Types

A number of liposomal formulations were prepared. The amount of trapped aqueous phase was determined and compared for each "type" of liposome prepared. The results appear in table 1, below.

For the preparation of IF liposomes, MLVs were prepared as described below to a final concentration of 20 $\mu$moles DPPC per ml of aqueous buffer. The MLVs were then sonicated in a bath type sonicator at 50° C. until translucent (SUVs). After the SUVs cooled to room temperature, ethanol was added to a final concentration of 2.0 M in the final aqueous suspension. For examples A1 and A2 (see table 1, below), ethanol was removed by dilution followed by washing. For B1 and B2, ethanol was removed via positive pressure displacement using N2, after which the samples were diluted and washed. Sample C had one half the initial lipid concentration of A and B and ethanol removal was achieved as for sample A.

For the preparation of MLVs, 100 mg DPPC in 5 ml chloroform was rotary evaporated to a thin dry film in a round bottom flask to which a 1 ml aqueous buffer solution containing 0.04 mM diphenyl hexatriene was added. Thereafter, the lipid mixture was vigorously vortexed until all lipid was removed from the wall.

FATMLVs were formed by subjecting unwashed MLVs as described above to 5 freeze and thaw cycles as described by Bally et al., U.S. Pat. No. 4,975,282, issued Dec. 4, 1990.

SPLVs were prepared by forming the thin dry film of DPPC as described above for MLVs and then dissolving the lipid film in 5 ml ethyl ether to which 0.5 ml of aqueous buffer was also added. This mixture was then emulsified in a bath type sonicator, a stream of N2 was used to stir the emulsion while removing the ether as described by Lenk, et al., U.S. Pat. No. 4,522,803. Ether removal was continued until no residual odor was detected (approximately five minutes). The resulting lipid mixture was resuspended in 1 ml aqueous buffer.

MPVs were formed as described in U.S. Pat. No. 4,588,578, by preparing a monophase of 100 mg DPPC and 5 ml chloroform, 5 ml ethanol and 0.5 ml aqueous buffer, rotary evaporating to dryness, and resuspending the suspended film in 1 ml aqueous buffer by vigorous vortexing.

To determine the captured aqueous volume, 20 μl of a 10 mM 4-trimethylammonium TEMPO (4-TMAT) solution was added to 0.98 ml of the liposomal suspensions. The samples were then vortexed and the outer aqueous phase was separated from the liposomes by centrifugation. Because 4-TMAT neither binds to nor permeates the liposomes used in this study, it is concentrated in the outer aqueous phase. Measurement of 4-TMAT's concentration allows for calculation of the internal aqueous phase or captured volume as detailed in Perkins, et al., BBA, 943, 103 (1988). The results of this analysis appear in Table 1, below. As seen, the IF liposomes sequester significantly greater volumes, in some cases as much as 10 times that attained with the other liposome types.

TABLE 1

Comparison of Trapped Solute

| Liposome Type | *Captured Volume (μl/μmole) |
|---|---|
| IF | |
| A1 | 6.7 |
| A2 | 7.8 |
| B1 | 8.3 |
| B2 | 7.2 |
| C | 8.9 |
| MLV | |
| 1 | 0.56 |
| 2 | 0.78 |
| MPV | |
| 1 | 0.71 |
| 2 | 1.9 |
| SPLV | |
| 1 | 2.0 |
| 2 | 2.8 |
| FATMLV | |
| 1 | 2.7 |
| 2 | 2.6 |

*Captured volumes were measured using the EPR technique (Perkins, et al. (1988) Biochim. Biophys. Acta 943, 103) where the samples are examined after formation.

Example 4

Procedure for Formation of IF Liposomes

Liposomes (LUVs, MLVs, SPLVs, etc. as prepared above) comprising a saturated lipid such as dimyristoylphosphatidylcholine, dipalmitoylphosphatidylcholine or distearoyl phosphatidylcholine are prepared and sized to 1 micron or less (preferably, 0.025 microns) by extrusion, sonication or homogenization. A bioactive agent which does not interact with the lipid is then mixed in with the aqueous solvent used to form the Liposomes (final lipid concentration should be about 5 to 100 mM, preferably about 10 to 35 mM). The temperature of the liposomes are below the main phase transition temperature of the lipid. Thereafter, ethanol is added to a final concentration of about 1.75 to about 2.5 M in the aqueous solvent. In the case of bioactive agents which interact with the lipid, the agents are generally added to the solvent after the addition of ethanol and formation of the IF gel. At this stage, the procedure can be stopped and the resulting gel used in topical and oral formulations. Alternatively, the gel may be used to form IF liposomes of the present invention.

To form IF liposomes, the gel is incubated at a temperature below the Tm of the lipid for a period ranging from about 1 minute to about 1 hour followed by an incubation period of about 1 minute to about 1.0 hour at a temperature above the Tm of the lipid. The inducer is then removed by evaporation, positive nitrogen pressure or dilution. In the case of ethanol, the ethanol may be diluted to a concentration below about 0.2 M. As the inducer is removed, liposomes form, generally varying in size from about 0.25 microns to about 20 microns.

Example 5

Scale-up of Diatrizoate-DPPC IF Liposomes 600 mg of DPPC were dried to a film from chloroform by rotary evaporation, then dried further under vacuum for 16 hours. The lipid was resuspended in 6 ml of 0.9% saline by incubation in a 51° C. bath for approximately 15 minutes. The resulting multilamellar liposomes (MLVS) were transferred to a 30 ml Corex tube and bath sonicated for two hours at 51° C. until the solution was translucent At this point only 4.1 ml of liposome suspension could be retrieved. 12 ml of diatrizoate (Renografin-76™, available from Bristol-Myers Squibb), 12 ml of deuterated water ("dH$_2$O"), and 2 ml of ethanol were mixed in a 50-ml centrifuge bottle to which the 4.1 ml lipid (still at 51° C.) was added and then briefly vortexed. Within 10 minutes the mixture became a loose, pourable gel which was allowed to set at room temperature for 2 hours. Next, the suspension was incubated in a 51° C. bath for 1 hour. At this point the sample was split in half to facilitate ethanol evaporation. While still immersed in the bath, N2 was bubbled through each aliquot for a period 12 minutes. The samples were allowed to cool to room temperature followed by dilution with 20 ml of 0.9% saline per aliquot. The preparation was washed by repetitive centrifugation at 10,000×g at 20 C for 10 minutes for 3 cycles. The sample was assayed as described for Example 6 below. The results appear in Table 2, below.

TABLE 2

| Aliquot | I:L | % Entrapped | mg/ml Iodine | Pellet Weight (mg) |
|---|---|---|---|---|
| A | 2.4 | 16%[1] | 48.8 | 7.42 |
| B | 3.8 | 25% | 67.6 | 8.07 |

[1]Based on 12 ml. of diatrizoate initially added.

Example 6

Diatrizoate-HSPC IF Liposomes 400 mg HSPC (Natterman Phospholipids) was hydrated at 70 C in 10 ml dH$_2$O for about 1 hour and probe sonicated until translucent (30 minutes). 14 ml diatrizoate (Squibb) containing approximately 1 μCi/ml 125I-diatrizoate was mixed with 2.1 ml dH$_2$O and 4.9 ml ethanol in a 50 ml screw-top Corex™ tube. 7 ml of the HSPC small unilamellar liposomes (SUV) was added while mixing; this was done while the SUV were still above their Tm. A solid gel formed immediately and was allowed to set at room temperature, covered for approximately 1 hour. The preparation was then incubated for 2 hours in a 70° C. water bath, uncovered after which N$_2$ was bubbled through the now liquid prep for 23 minutes. The N$_2$ flow rate was at 10 on the Manostat™ flowmeter. A 4 ml aliquot was dispensed into a 30 ml Corex™ tube and allowed to cool to room temperature 10 ml of 900 ml meglumine buffer (prepared from meglumine, NaCl, citrate, EDTA) was added and the preparation was vortexed briefly. The unentrapped diatrizoate was removed by repetitive centrifugation at 10000×g at 18° C. for 15 minutes for 3 cycles. The final iodine concentration was determined by extrapolation from a UV spectrophotometric assay of diatrizoate (A256) to be 106.3 mg/ml. The final lipid concentration was 12.1 mg/ml as determined by the standard methodologies described by Chen, et al., Analytical Chem., 28, 11, 1756 (1956). The final I:L ratio was 8.8 (w/w). The resulting liposomal suspension was stored under ambient conditions.

Example 7

Iotrolan-HSPC IF Liposomes 1 g HSPC (Natterman Phospholipids) was hydrated at 70° C. in 25 ml dH$_2$O for about 1 hour and probe sonicated until translucent (about 30 minutes). The SUVs produced were transferred to a 50 ml screw-top tube and spun at 5000×g for about 5 minutes in order to pellet any titanium present The SUVs were decanted from the titanium pellet and incubated in a 70° C. water bath for about 5 minutes before being added to the following solution: 44 ml 125I-labeled Iotrolan was mixed with 15.6 ml ethanol and 6.4 ml dH2O. This solution was then divided into 4×16.5 ml aliquots in 50 ml screw-top tubes. 5.5 ml SUVs were added to each tube while mixing, resulting in the formation of loose gels. The gels sat covered for 1 hour at room temperature, then each was transferred to a 70° C. water bath for 1 hour, uncovered, after which N$_2$ was bubbled through the liquid in each tube for 13 minutes at a flow rate of 40 on the gas flowmeter. Each tube was emptied into a 250 ml Erlenmeyer flask where it cooled to room temperature. About 150 ml sterile PBS (phosphate buffered saline without Ca and Mg, pH 7) was added while swirling the flask. The unentrapped Iotrolan was removed by repetitive centrifugation at 10000×g for 10 minutes at 18° C. for 3 cycles and spun at about 5000×g. The final iodine concentration was based on the initial specific activity of the Iotrolan solution at 300 mg/ml iodine and was found to be 152.7 mg/ml. The final phospholipid concentration was determined to be 32.7 mg/ml by the method of Chen, et al., Analytical Chem., 28, 11, 1756 (1956) and was corrected for the presence of phosphate in the buffer. These values resulted in a final I:L ratio of 4.7 (w/w). The resulting liposome suspension was stored under ambient conditions.

Example 8

Shelf Stability of Radiocontrast Agent IF Liposomes Stored Under Ambient Conditions 50 µl of either diatrizoate or iotrolan HSPC IF liposome preparations (radiolabeled) were diluted with 1 ml of their original suspension buffer and centrifuged at 16,000×g in a microfuge at room temperature for 10 minutes. The supernatants were removed and both the pellets and the supernatants counted for 125I. After 62 days at 25° C., there was 4% of the radiolabel in the supernatant of the diatrizoate liposomes and after 54 days, 3% in the supernatant of the iotrolan liposomes. Based upon these results, the preparations exhibit a shelf life of at least about 1 year when stored under ambient conditions.

Example 9

Effect of Initial Lipid Concentration on Entrapment of Diatrizoate in DPPC IF Liposomes The results which appear in Table 3, below represent IF liposome preparations made as previously described In Example 5 with variation in the initial lipid concentration. Briefly, in 15 ml. tubes, 1 ml diatrizoate was mixed with dH$_2$O and DPPC sized unilamellar Liposomes (SUVs) at 50 mg/ml to achieve the final volumes shown below. Before lipid addition, 87.5 µl ethanol per ml. (final volume 2M) was added to the diatrizoate solution. Preparations sat, capped, for 1 hour at room temperature followed by incubation in a 51° C. bath, uncapped. After 1 hour N2 was bubbled through each sample for 2 minutes. After cooling to room temperature, each sample was diluted with 10 ml of 0.9% saline solution and washed by repetitive centrifugation at 10,000 g for 15 minutes at 20° C. for 3 cycles. The samples were assayed as previously described (Example 3). The results appear in Table 3, below.

TABLE 3

| mg. DPPC/<br>Total ml | I:L | %<br>Entrapped[1] | mg/ml<br>Iodine | pellet<br>Weight |
|---|---|---|---|---|
| 50 mg/<br>2 ml. | 1.7<br>1.8 | 38<br>35 | 57.6<br>58.9 | 2.47<br>2.18 |
| 25 mg/<br>2 ml. | 3.5<br>3.1 | 37<br>28 | 68.7<br>62.1 | 2.01<br>1.66 |
| 25 mg/<br>3 ml. | 5.0<br>5.6 | 49<br>56% | 73.5<br>80.3 | 2.47<br>2.56 |

[1]Based on 1 ml diatrizoate initially added.

Example 10

Entrapment of Gentamicin Via IF Liposomes

A solution of Gentamicin sulfate (Sigma Chemicals, St. Louis, Mo., USA) was prepared in 0.9% saline solution to a final concentration of 500 mg/ml. Separately, 100 mg of DPPC (Avanti Polar Lipids) was evaporated to dryness and hydrated in 2.5 ml saline to a final concentration of 40 mg/ml. The DPPC mixture was sonicated on a bath sonicator to clarity.

The following mixtures were then made. Note that the ethanolic inducer was added before the solutions containing gentamicin sulfate.

A—0.5 ml. DPPC solution, plus ethanol ("EtOH") (to a final concentration of 2M) and 0.5 ml. gentamicin solution;

B—0.25 ml. DPPC solution, plus 0.25 ml 0.9% NaCl saline solution, EtOH (to a final concentration of 2M) and 0.5 ml of gentamicin solution;

C—0.25 ml. DPPC solution, plus 0.75 ml saline, EtOH (to a final concentration of 2M) and 1.0 ml. of gentamicin solution;

Each of the above preparations were then assayed for gentamicin activity by the agar well diffusion bioassay to determine lipid:gentamicin concentration. In brief, the liposomes in each of the above preparations were then disrupted with 0.2% Triton-X 100 (Biorad Laboratories, Richmond Calif.) and assayed for gentamicin activity using an agar well diffusion bioassay with *Bacillus subtilis* (ATCC #6633) as the indicator organism. Lipid concentration was determined by standard methods described by Ames, et al., Journal of Biological Chem. 235, 236, 769 (1960).

The results of the bioassay determinations appear in Table 4, below. The results indicate that very low lipid/gentamicin weight ratios may be obtained.

TABLE 4

Entrapment of Gentamicin in IF Liposomes

| Sample | Gentamicin[1] mg/ml | Lipid mg/ml | Lipid/Gentamicin Weight Ratio |
|---|---|---|---|
| A1 | 6.18 | 19 | 3.07 |
| A2 | 3.13 | 12.5 | 4.0 |
| B1 | 2.16 | 13.2 | 6.11 |
| B2 | 3.15 | 11.0 | 3.49 |
| C1 | 4.25 | 8.6 | 2.02 |
| C2 | 2.46 | 6.05 | 2.46 |

[1]Corrected for Potency (616 µg/mg).

Example 11

Scale up of DSPC—Iotrolan IF Liposomes

Eight (8) grams of DSPC were mixed in 200 ml of Water for Injection ("WFI") at 70° C. for 30 minutes. The resulting suspension was passed through a Microfluidizer homogenizer 25 times at a pressure of 11,000 psi thereby forming SUVs. The resulting SUVs were filtered through a 0.22 µm pore size Millipore tortuous path polymeric filter.

Iotrolan (92 ml, at 300 mg/ml), 13.4 ml WFI, and 32.6 ml ethanol were admixed in a 2,000 ml capacity round bottom flask. The SUVs (44 ml) were admixed in the flask at room temperature (about 25° C.) and mixed using a banana paddle mixer for 10 seconds. The gel which formed thereafter mixing was allowed to sit undisturbed for 1.25 hours.

The round bottom flask was placed in a 70° C. water bath and mixed using the banana paddle at 66 psi for one (1) hour. Ethanol was then removed by nitrogen sparge over the aqueous surface at a rate of 4.7 L $N_2$/minute for one (1) hour, collecting the ethanol in a trap, with the mixing increased to about 135 psi. The final volume was adjusted to about 400 ml with carbonate buffer (0.4 mg/ml $NaHCO_3$, 0.1 mg/ml disodium EDTA, in 0.9% saline). The resulting IF liposomes were washed, thereby separating liposomes from unentrapped Iotrolan by diafiltration through a 0.2 µm Microgon filtration device. Seven washes of 100 ml were employed with removal of 300 ml last, as a concentrating step. This washing step proceeded for 25 minutes.

Analysis of the resulting Iotrolan/DSPC liposomes yielded the following results shown in Table 5, below:

TABLE 5

| | |
|---|---|
| Lipid concentration | 23.0 mM, 18.2 mg/ml |
| Lyso PC content | 0.9% |
| Iotrolan entrapped | 264.8 mg/ml |
| Free Iotrolan | 1.4% |
| Iotrolan/DSPC | 14.5 |
| Captured Volume | 13.7 µl/µmole |
| Size distribution | 90% less than 3.6 µm |
| | 50% less than 2.8 µm |
| | 10% less than 1.2 µm |

Example 12

Encapsulation Efficiency of DPPC—IF Vesicles as a Function of Ethanol Concentration DPPC (powder) was mixed with 10 mM Tris HCl, 150 mM NaCl also containing a trace amount of $^{14}C$ sucrose, at pH 7.4 to a concentration of 20 mg/ml DPPC, for a total of 2.0 ml. The mixing was done at a temperature above the phase transition temperature of DPPC, at 50°–53° C., and resulted in MLVs. The MLVs were sonicated for one hour at 50–53° C. and cooled to room temperature, resulting in SUVs of about 30–50 nm in diameter. To the 2.0 ml of SUVs was added enough ethanol (100%) to result in a 3.0 M ethanol concentration (0.43 ml ethanol; 20% ethanol by weight total); the mixture was vortexed to homogeneity. The suspension was allowed to sit capped and undisturbed for one hour at room temperature, then was incubated one hour at a temperature above the transition temperature of DPPC i.e., at 50°–55° C. with the cap loosened. While still incubating above the lipid $T_m$, a gentle stream of $N_2$ was bubbled through the mixture for 3 minutes. A sample (100 µL) was removed for a $^{14}C$ sucrose encapsulation study, and a 4 µL and 8 µl aliquot also removed for determination of Pi according to the Bartlett phosphorous assay of Chen et al. Ten ml of Tris/NaCl buffer was added to the resulting IF liposomes, and the mixture was centrifuged at 9,000×g for 15 minutes, the supernatant decanted and the pellet resuspended in Tris/NaCl buffer and centrifuged two additional times for a total of 3 washes. The pellet was finally resuspended in 2.0 ml buffer. Another 200 µL sample was removed for the encapsulation study, as well as 4.0 µL and 8.0 µL aliquots for the Pi assay.

The above method was repeated using a total ethanol concentration of 1.0, 2.0, 2.5, 3.5, and 4.0 M in solution.

The internal volume of the IF liposomes is expressed as µL per µM of phosphorous Pi, and was measured by $^{14}C$ sucrose encapsulation and CAT 1 EPR methods.

Figure 4A:
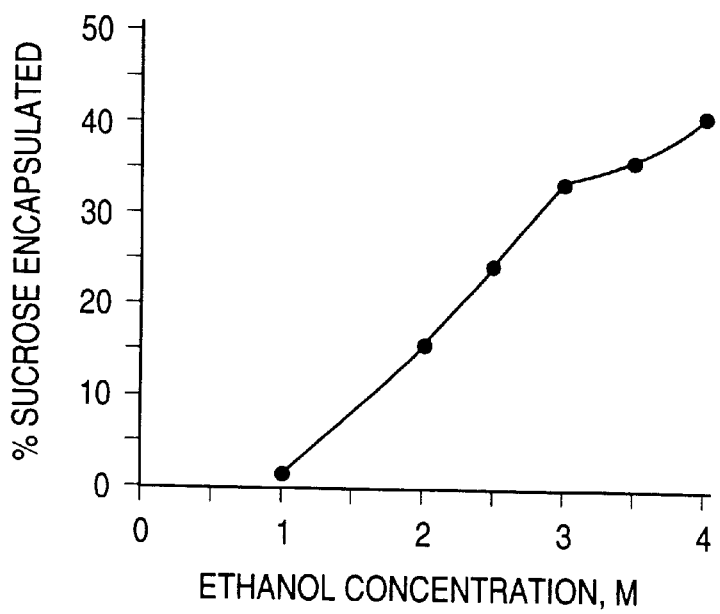
FIG. 4. Graphic representation of the $^{14}C$ sucrose encapsulation percentage as a function of ethanol concentration. The internal volume of DPPC IF liposomes as a function of increased ethanol concentration is shown in FIG. 4B, solid circles representing internal volume determined by $^{14}C$ sucrose encapsulation; open circles refer to the CAT 1 EPR measurement.
FIG. 4C represents the percentage of DPPC recovered as a result of failure of IF liposomes to form at 1.0 M ethanol concentration.

The $^{14}C$ sucrose encapsulation was performed as follows: Following the $N_2$ bubbling step, the 100 µL sample removed for the $^{14}C$ sucrose encapsulation study was counted in a Beckman model Ls 6800 scintillation counter. Similarly, following the centrifugation step, the 200 µL sample removed was centrifuged at 3,000×g using a table top centrifuge, and both the pellet and the supernatant was counted in the scintillation counter. In addition, the Pi was determined as before. The $^{14}C$ sucrose encapsulation was thereby determined and the results are represented graphically in FIG. 4A.

The CAT 1 EPR study was performed as in Example 13 hereinbelow.

Figure 4B:
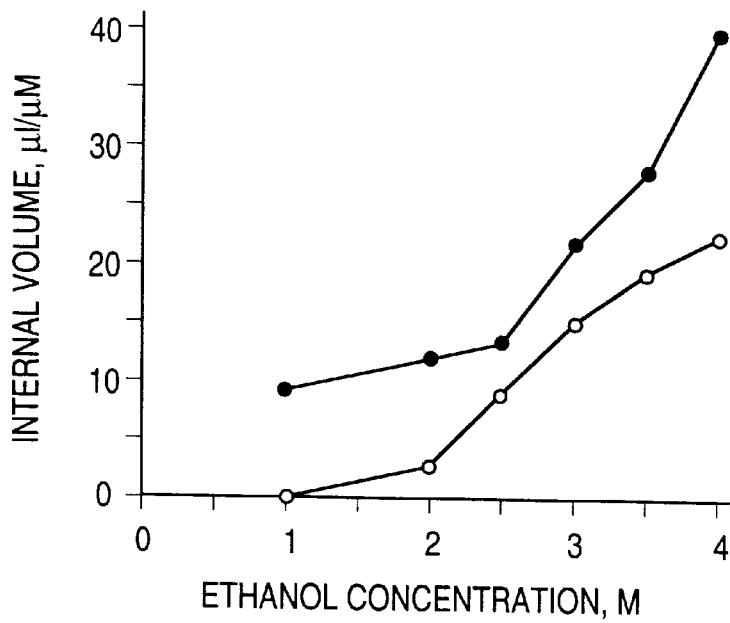
Figure 4C:
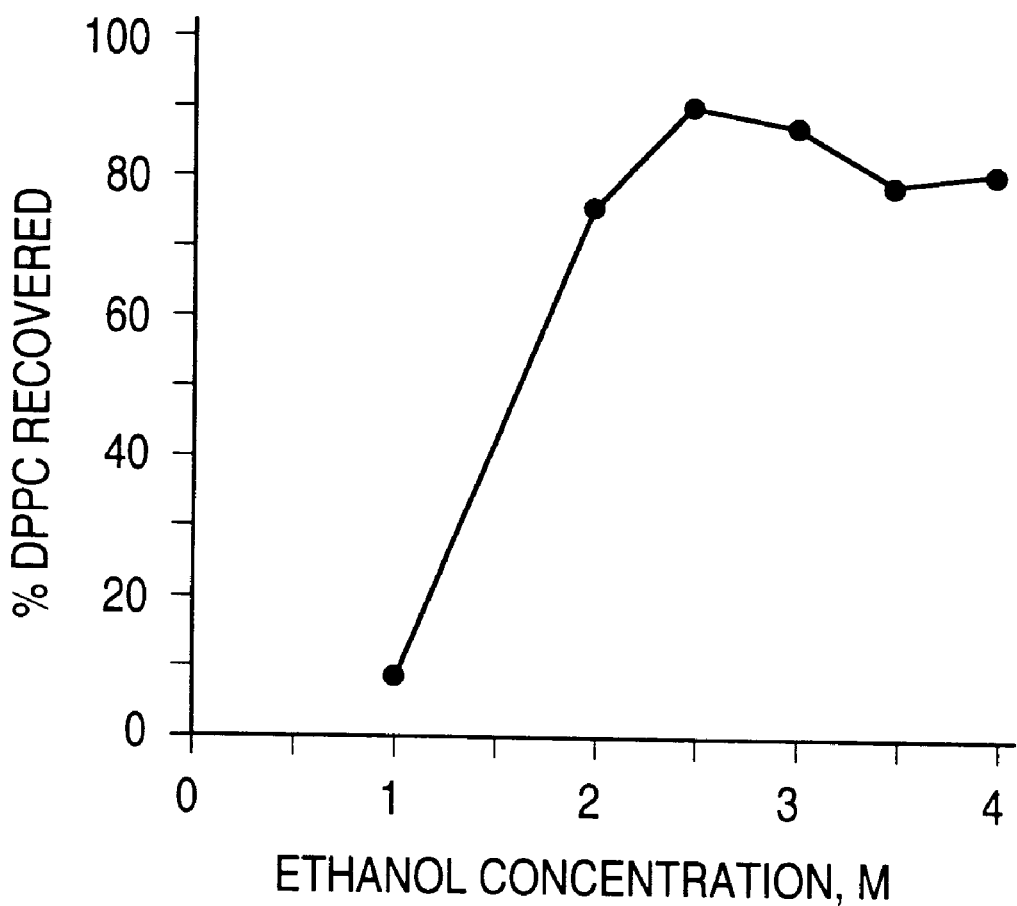

As shown in FIG. 4B, the internal volume of the DPPC IF liposomes increased as a function of increased ethanol concentration, consistent with higher encapsulation efficiency of liposomes at higher ethanol concentrations. The percentage of DPPC recovered following the three centrifugation washes is shown in FIG. 4C.

Example 13

Encapsulation Efficiency of DSPC, DHPC, DOPC and EPC IF Vesicles as Measured by Sucrose and EPR Methods The methods of Example 12 were repeated using the lipids DSPC, DHPC, DOPC and EPC, using a final concentration of 3.0 M ethanol. The low temperature incubations following ethanol addition were done at 50° C. for DOPC and EPC. The high temperature incubation was done at 70° C. for all samples.

Incubation of DSPC took place at 70° C., DHPC at 50° C., and DOPC and EPC at 5° C.

The DOPC and EPC samples were not washed by centrifugation but filtered through Amicon 30K microconcentration device (Grace Co.) filters. 100 µL aliquots were removed from the filtrate and from the sample before and after the filtration for the entrapment efficiency analysis.

Entrapment efficiency was calculated by the sucrose encapsulation, CAT 1 EPR and TEMPONE EPR methods, methods for performing all of which are recited hereinbelow.

Figure 5:
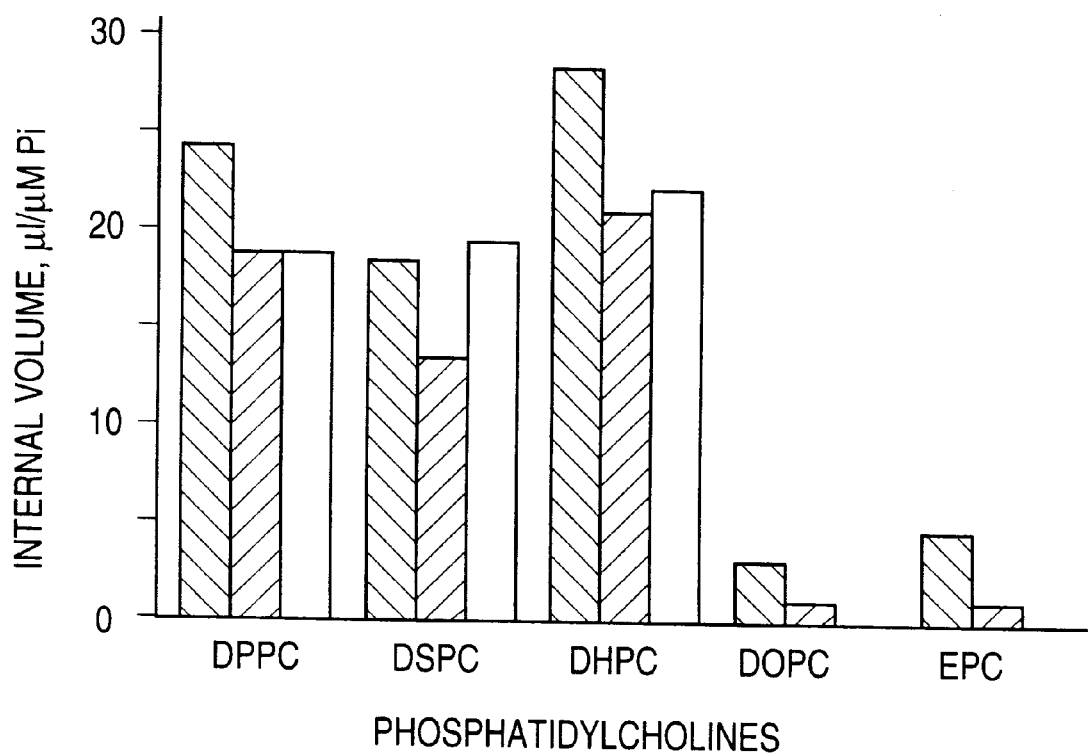
FIG. 5. Internal volumes of IF liposomes formed from various lipids using $^{14}C$ sucrose, TEMPONE EPR and CAT 1 EPR methods (solid, diagonal, and shaded bars, respectively).

As shown in FIG. 5, the three phosphatidylcholines which are known to interdigitate (DPPC, DSPC and DHPC) all produced IF liposomes with high internal volumes. EPC and DOPC had relatively low internal volumes, were relatively small and could not be pelleted using a table top centrifuge (9,000×g). Therefore it was not possible to measure internal volumes of these liposomes using the CAT 1 EPR method.

CAT 1 EPR METHOD FOR DETERMINING ENTRAPMENT

This method is alternatively known as the external solvent volume method, described in Perkins et al., 1988, Biochim. Biophys. Acta, 943:103–107. The internal volume of liposomes was determined by subtracting the external solvent volume, calculated by measuring the concentration of a membrane impermeant spin probe from the total volume of the liposome suspension. The external solvent volume was calculated by adding a known amount of a spin probe 4-trimethylammonium-2,2,6,6-tetramethylpiperidine-1-oxyl iodide ("CAT 1") to a liposome suspension. The liposome suspension was centrifuged to pellet the liposomes. The concentration of CAT 1 in the solvent was determined by comparison of the magnitude of the CAT 1 EPR signal from the supernatant to an EPR signal versus CAT 1 concentration calibration curve. The CAT 1 concentration in the supernatant was higher than what would be expected based on the amount of CAT 1 added because the volume available to the spin probe was reduced as the probe was excluded from the inside volume of the liposomes. Correction was also made for the sample volume due to the lipids themselves.

Procedure: A stock solution containing 10 mM CAT 1, 10 mM Tris HCl (pH 7.4), 150 mM NaCl was used for the calibration buffer solutions containing 100, 200, 300 and 400 μM CAT 1. The EPR spectrum of each stock solution was recorded with a Brucker ER 100D spectrometer. The peak to peak height of the $M_I$=+1 resonance line of each spectrum measured for each concentration and a peak height versus CAT 1 concentration curve was constructed.

CAT 1 stock (0.20 μM) was added to 1.00 ml of the liposome suspension ($V_t$) and vortically mixed. The liposomes were pelleted by centrifugation on a table top centrifuge at 9,000×g and a small portion of the supernatant was drawn into an EPR capillary tube and sealed. The peak to peak height of the $M_I$=1 resonance line was measured. The solvent concentration of CAT 1 was determined from the magnitude of the sample EPR signal and the calibration curve.

The external solvent volume Vo was obtained by the calibration curve. The external solvent volume Vo is equal to M/C where M is the moles of CAT 1 added and C is the CAT 1 concentration in the supernatant. V1 is the volume occupied by the lipid, is expressed as Vi=1.00−Vt−V1, where V1 is the volume of the lipid. The internal volume, Vi, divided by the phosphate content of the sample gives the internal volume per μM Pi which is the standard way of expressing the internal volume of liposomes.

TEMPONE EPR METHOD FOR DETERMINING ENTRAPMENT

This method is alternatively known as the broadening agent method, described in Anzai et al. (1988). The internal volume of liposomes is determined by measuring the amount of membrane permeant EPR spin probe broadening agent. Normally rapidly tumbling aqueous EPR spin probes have relatively narrow spectral line shapes, however, addition of paramagnetic ions decreases the spin-spin relaxation time ($T_2$). If the broadening agent is at high enough concentration it can drastically broaden the spectral line shape and dramatically decrease the peak to peak height of EPR signals. In effect, if the EPR broadening agent has access to the spin probe, the probe signal is eliminated.

The measurements are done by adding the membrane permeant EPR spin probe 4-oxo-2,2,6,6-tetramethylpiperidine-1-oxyl ("TEMPONE") to liposomes suspensions. The two 200 μl aliquots were removed from each liposome suspension. One of the aliquots was diluted with 200 μl buffer while the other was diluted with 200 μl of buffer plus the membrane impermeant broadening agent potassium tris(oxalato)chromate (III). The EPR signal from the aliquot diluted with buffer is proportional to the total sample volume, while the EPR signal from the aliquot diluted with the potassium tris(oxalato)chromate (III) is proportional to the sample volume inside the liposomes.

Procedure: A stock solution of 50 mM TEMPONE, 10 mM Tris-HCl (pH 7.4), 150 mM NaCl stock solution was prepared. TEMPONE stock (10 μl) was added to 0.5 ml suspension of liposomes and vortically mixed. A 200 μl aliquot was taken from each sample and diluted with 200 μl of buffer. Another 200 μl aliquot was taken and diluted with a 100 mM potassium tris(oxalato) chromate (III), 50 mM NaCl solution. The osmotic strength of the buffer and the chromate solutions were previously checked with a vapor pressure osmometer to insure that they were equal to within 1–2%. The samples were vertically mixed.

The EPR spectra were recorded with a Brucker ER 100D spectrometer. Samples were drawn into EPR capillary tubes and sealed. The EPR spectrum of the buffer sample was recorded first, the chromate solution sample was then prepared, and the EPR spectrum of this sample was then immediately recorded. The peak to peak height of the $M_I$=−1 resonance line was used to measure the relative concentrations of the unaffected spin probe in both samples. The total sample volume was proportional to the EPR signal size of buffer diluted aliquot divided by the spectrometer gain setting (ST), while the internal volume of the liposomes was proportional to the EPR signal of the aliquot diluted with chromate solution divided by the gain setting (SI). The internal sample volume (Vi) was given by the SI/ST times the sample volume V. The internal volume, Vi, of the sample was divided by the phosphate content of the sample to give the internal volume per μM Pi which is the standard way of expressing the internal volume of liposomes.

Example 14

Encapsulation Efficiency of DPPC LUVET—IF Vesicles as a Function of Initial Size of Liposomes DPPC (422 mg powder) was hydrated with 21 ml of Tris/NaCl with a trace amount of $^{14}C$ sucrose according to the methods of Example 12, for a total concentration of DPPC of 20 mg/ml. Vortical mixing of the sample at 50–55° C. resulted in DPPC MLVs. FAT MLVs were prepared according to the methods of Cullis et al., U.S. Pat. No. 4,975,282, issued Dec. 4, 1990, for a total of 10 freeze and thaw cycles. The resulting DPPC FATMLVs were extruded ten times using the LUVET apparatus at 60°–65° C. according to the methods of Cullis et al., WO 86/00238, and employing a single 1.0 μm Nucleopore polycarbonate filter. Two ml of the LUVET processed liposomes were set aside.

The above method was repeated employing 0.4, 0.2, and 0.1 μm polycarbonate filters, until 2.0 ml LUVET samples of the following diameters were produced: 0.1, 0.2, 0.4, and 1.0 μm.

When FAT MLVs were employed for the purposes of this Example, they were used as is, without extrusion. SUVs were prepared according to the methods of Example 12 by sonication of the remaining 0.1 μm filtered LUVETs.

Internal volumes of these liposomes were calculated by $^{14}C$ sucrose encapsulation as well as CAT 1 EPR and TEMPONE EPR methods as described hereinabove.

Figure 6:
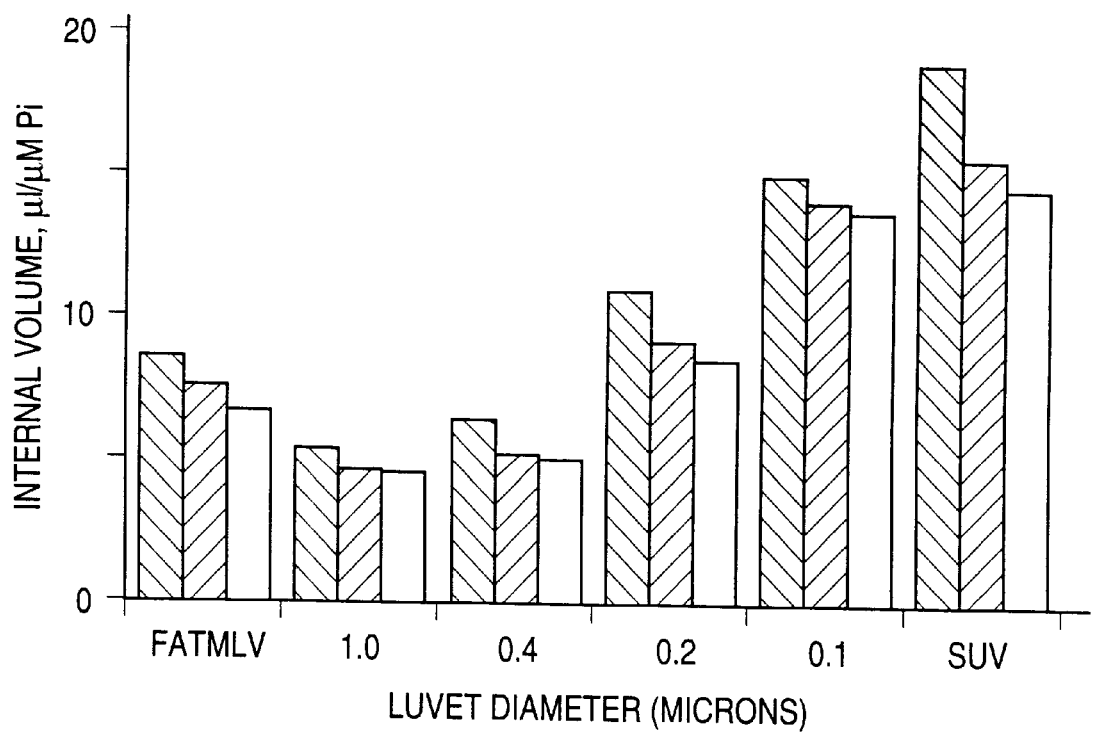
FIG. 6. Internal volume of DPPC IF liposomes as a function of initial size of liposomes prior to the addition of ethanol. Internal volumes of these liposomes were calculated by $^{14}C$ sucrose encapsulation as well as CAT 1 EPR and TEMPONE EPR methods (solid, diagonal and shaded bars, respectively).

As shown in FIG. 6, except for FATMLVs, the internal volume of the IF liposomes increased with decreased size of "starting" liposomes e.g., liposomes prior to the addition of ethanol; these results indicating that the diameter of the starting liposome was an important parameter in determining the final volume of the IF liposome.

Example 15

Incorporation of DPPG into DPPC IF Liposomes

IF liposomes were prepared from DPPC/dipalmitoyl phosphatidylglycerol (DPPG) SUVs according to the methods of Example 12 with the following modifications. A total of 30 mM phospholipid (DPPC and DPPG) was employed, 0.17 mole fraction (17 mole percent) DPPG. DPPC and DPPG each in chloroform were added to a round bottom flask (50 ml capacity) and mixed well. The lipids were dried to a thin film in the flask by negative pressure (rotary evaporation) and the resulting film hydrated with 2.0 ml Tris/NaCl buffer, and heated to a temperature of 50–55° C. A total concentration of 3.0 M ethanol was employed. A trace amount of $^{14}C$ sucrose was added to the sample, and the suspension sonicated to clarity. Upon removal of the ethanol and incubation of the mixture to 50°–55° C., IF liposomes were formed.

The internal volume of the liposomes was calculated by $^{14}C$ sucrose encapsulation and TEMPONE EPR methods according to the methods of Example 13.

The above methods were repeated with 1.0, 0.83, 0.66, 0.50 and 0.00 mole fraction (100, 83, 66, 50, and 0 mole percent) DPPG. The results are graphically tabulated in FIG. 7A and B.

Figure 7A:
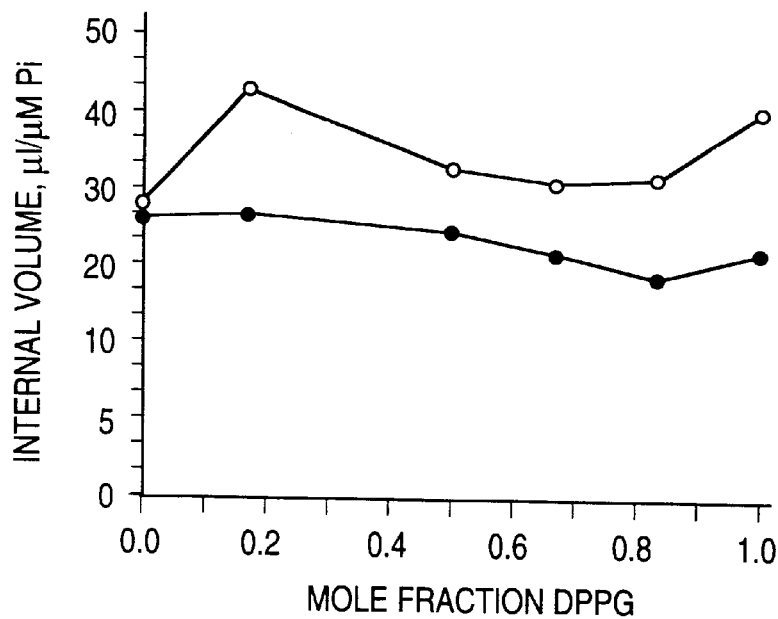
FIG. 7. Graphically representation of the incorporation of DPPG into DPPG-DPPC IF liposomes. The internal volumes of the IF liposomes are shown in FIG. 7A as a function of mole fraction of DPPG (volumes measured by $^{14}C$ encapsulation, open circles; volumes measured by the broadening agent TEMPONE EPR technique, closed circles).
FIG. 7B shows the percent recovery of Pi (closed circles) and $^{14}C$ labeled sucrose (open circles) as a function of DPPG.
Figure 7B:
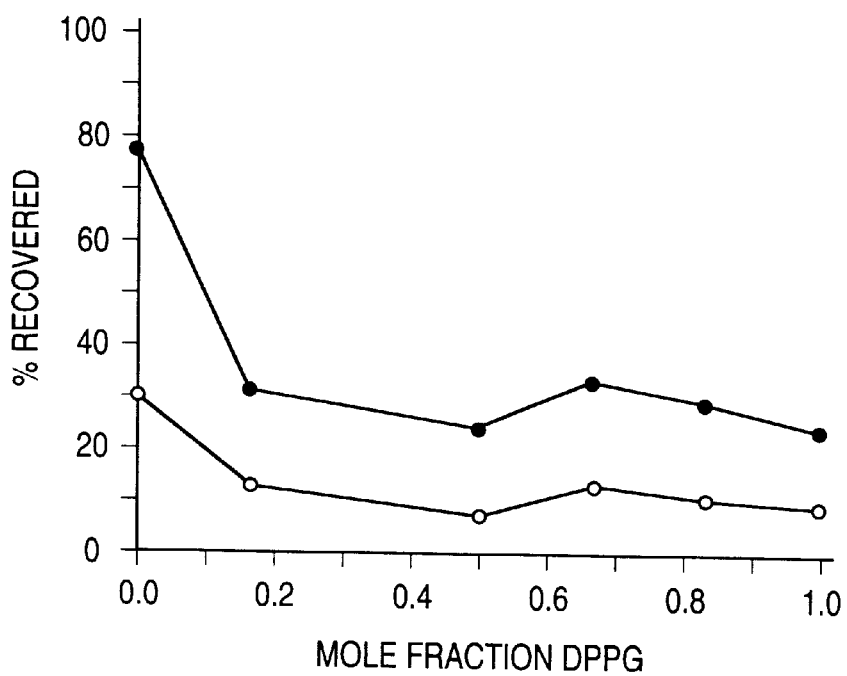

At higher DPPG fractions, IF liposomes were recovered only in low percentages as the liposomes did not pellet well during the wash step, a problem typical of negatively charged liposomes. The internal volumes of the IF liposomes recovered in the pellets are shown in FIG. 7A. The open circles are the volumes measured by $^{14}C$ encapsulation, while the closed circles are the volumes measured by the broadening agent (TEMPONE) EPR technique. FIG. 7B shows the percent recovery of Pi (closed circles) and $^{14}C$ labeled sucrose (open circles) as a function of DPPG.

Example 16

Captured Volume and Encapsulation as a Function of DPPC Initial Concentration

The materials and procedures of Example 12 were followed to form 2.00 ml of DPPC IF liposomes at 20 mg/ml. The above methods were repeated employing 2.0, 10.0, 20.0, 80.0, and 160.0 mg of DPPC resulting in five samples of 2.00 ml of DPPC IF liposomes at the following DPPC concentrations: 2.5, 5.0, 10.0, 40.0, and 80.0 mg/ml DPPC.

The $^{14}C$ sucrose encapsulation percentage and internal volumes of each of, the samples were calculated according to the methods of Example 13.

Figure 8A:
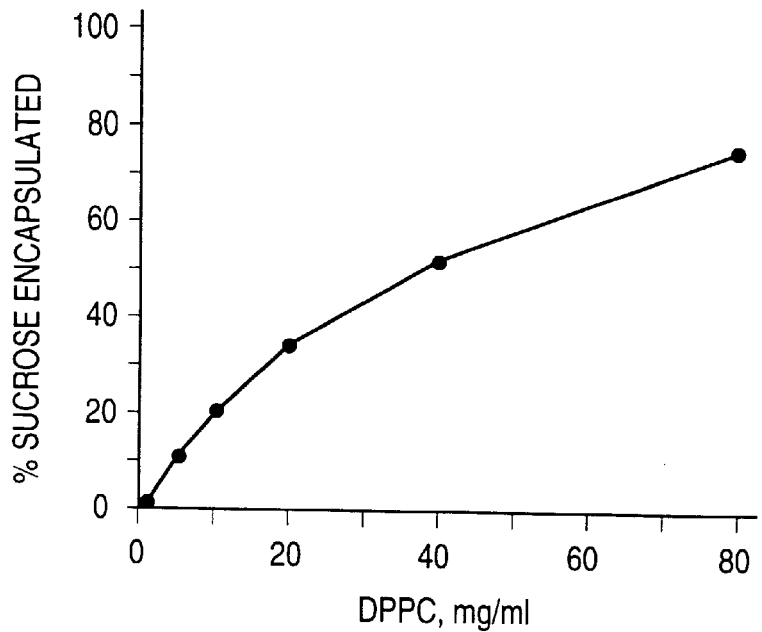
FIG. 8A shows the encapsulation percentage of sucrose in relation to the initial DPPC lipid concentration.
Figure 8B:
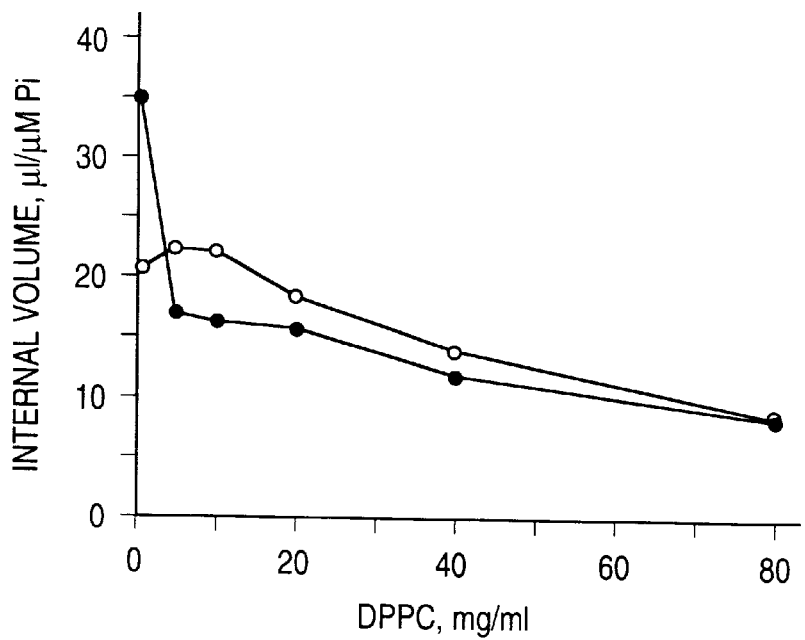
FIG. 8B shows the internal volume of the DPPC IF liposomes measured by both the $^{14}C$ sucrose method (closed circles) and the EPR method (open circles).
Figure 9A:
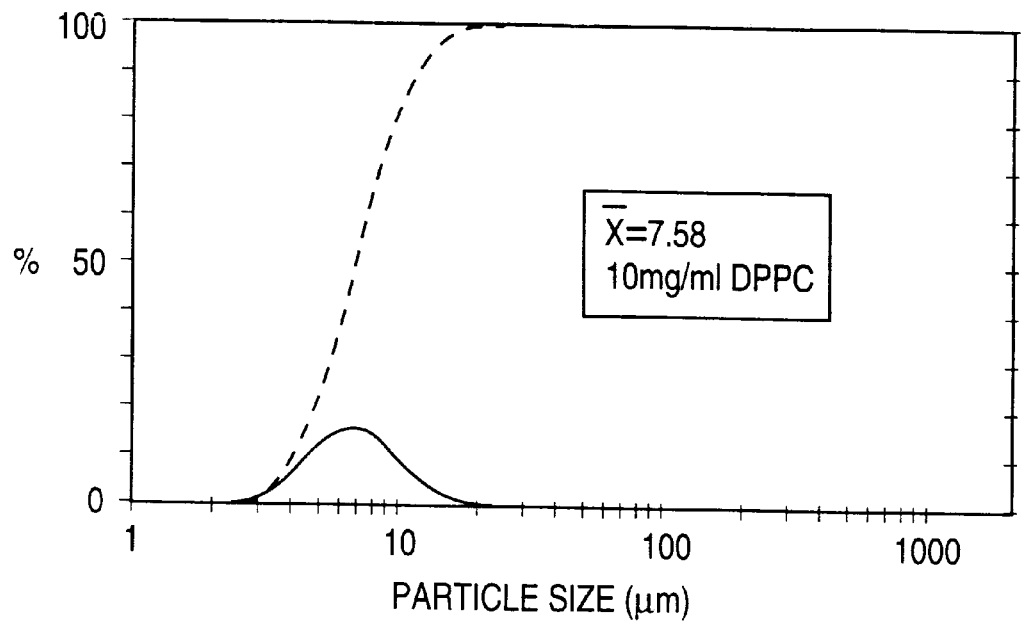
FIG. 9. Malvern particle size distributions of IF liposomes at (A) 10 mg/ml and (B) 20 mg/ml lipid.
Figure 9B:
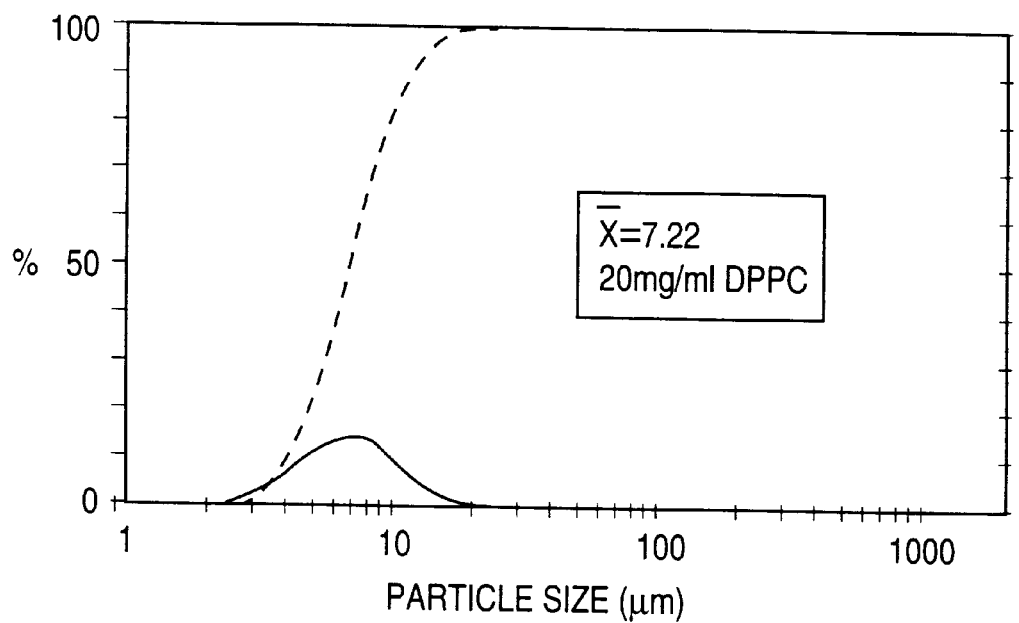

The results are represented graphically in FIG. 8A and B. FIG. 8A demonstrated that the encapsulation of sucrose increases with the initial DPPC lipid concentration. FIG. 8B shows the internal volume of the DPPC IF liposomes measured by both the $^{14}C$ sucrose method (open squares) or the EPR method (closed diamonds). The internal volume of the IF liposomes was about 15 to 20 μl/μM Pi when the initial concentration of DPPC was 1 to 20 mg/ml. Measurement made with the Malvern particle sizer indicated that the average diameter of these liposomes (containing 10 mg/ml and 20 mg/ml lipid) is about 7.0–7.5 μm (see FIG. 9A and B). This demonstrates that the internal volume of DPPC liposomes formed by the IF method was much larger than conventional MLVs.

Example 17

Effect of Cholesterol on Formation of DPPC IF Liposomes

The materials and procedures of Example 12 were followed to make IF liposomes employing DPPC and cholesterol, in a total of 30 mM lipid, using a total concentration of 3.0 M ethanol. The cholesterol and DPPC, provided in stock chloroform solutions at concentrations of 20 mg/ml, were admixed in a 50 ml capacity round bottom flask at 95% DPPC and 5% cholesterol. The lipids were dried to a thin film on the surface of the flask, and hydrated with Tris/NaCl as before. The incubation temperature was 50°–55° C.

Aliquots were removed to assay for cholesterol before and after the IF process, to insure the liposomes contained cholesterol, and to assay for the encapsulation of $^{14}C$ sucrose.

The above methods were repeated employing 0.00, 0.02, 0.10, 0.15 and 30.0 mole fraction (0, 2.0, 10, 15 and 30 mole percent) of cholesterol, The internal volumes of the liposomes were determined by $^{14}C$ sucrose encapsulation and both the CAT 1 EPR and TEMPONE EPR methods. The cholesterol content of the IF liposomes was measured using o-phthalaldehyde according to the methods of Rudel and Morris, 1973, J. Lipid Res., 14:14.

Figure 10A:
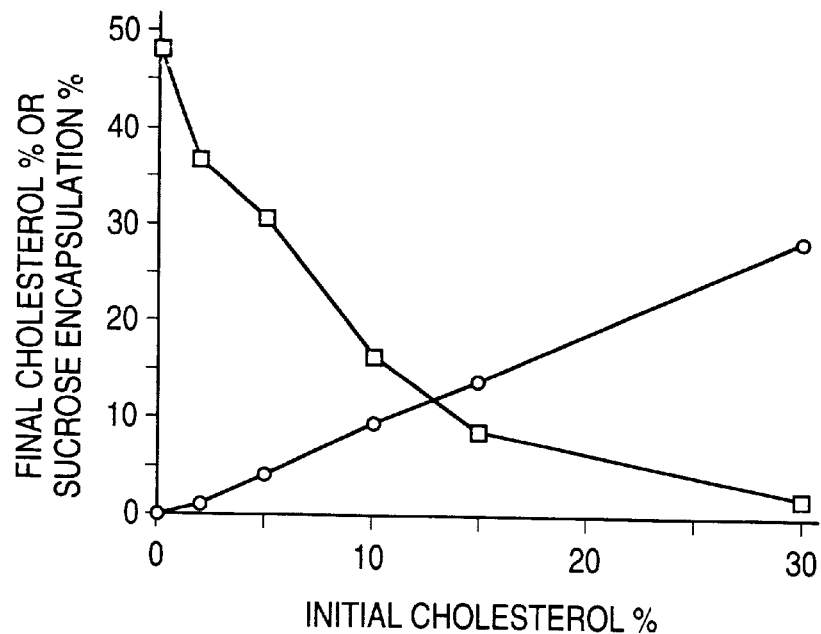
FIG. 10A show the "final" cholesterol concentration of the IF liposomes (open circles) and the final percentage of $^{14}C$ sucrose encapsulated (open squares) as a function of initial cholesterol percent of the liposomes prior to addition of ethanol.

Results are graphically represented in FIG. 10A and B. FIG. 10A show the "final" cholesterol concentration of the IF liposomes (open circles) and the final percentage of $^{14}C$ sucrose entrapped (open squares). As cholesterol content is increased, the amount of encapsulated sucrose decreased.

Figure 10B:
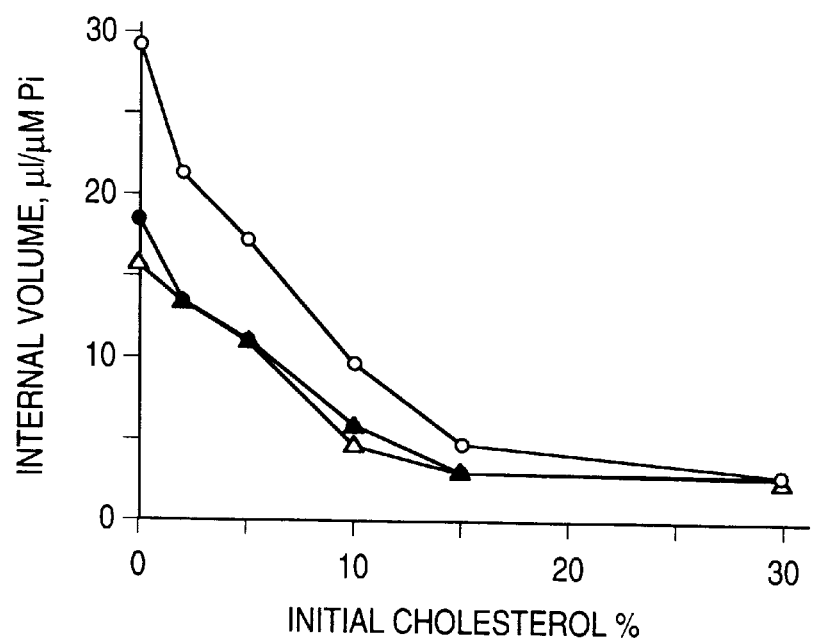
FIG. 10B shows the decrease in internal volume of the DPPC-cholesterol IF liposomes as a function of cholesterol content ($^{14}C$ sucrose encapsulation, CAT 1 EPR and TEMPONE EPR methods; open circles, open triangles and closed circles respectively).

FIG. 10B shows the decrease in internal volume of the DPPC-cholesterol liposomes as a function of cholesterol content. While the data from the Cat 1 EPR and TEMPONE EPR methods (open triangles and closed circles respectively are in close agreement, the data from the $^{14}C$-sucrose assay shows internal volumes significantly nigher. Without being bound to theory, the $^{14}C$-sucrose appears to be "sticking" to the liposomes thus giving readings for higher internal volume.

These studies and FIG. 10 indicate that the size of the IF liposomes decreases sharply with increasing cholesterol content, a conclusion that was supported by results of Malvern particle sizing; IF liposomes containing 0% cholesterol had on average diameter of 7.66 μm while 30% cholesterol IF liposomes were 3.99 μm.

Example 18

Effect of Dioleoylphosphatidylcholine (DOPC) on Formation of DPPC IF Liposomes

The materials and procedures of Example 12 were followed to make IF liposomes employing DPPC and dioleoyl phosphatidylcholine ("DOPC"), an unsaturated lipid, in a total of 30 mM lipid, using a total concentration of 3.0 M ethanol. The initial liposomes were formed of DPPC and DOPC, provided in stock chloroform solutions at concentrations of 20 mg/ml, which were admixed in a round bottom flask, with 0.20 mole fraction (20 mole percent) DOPC. The lipids were dried to a thin film on the surface of the flask via rotary evaporation, and hydrated with Tris/NaCl as before. The incubation temperature was 50°–55° C.

The above methods were repeated employing 0.00, 0.11, 0.55, 0.72 and 1.00 mole fraction (0, 11, 55, 72, and 100 mole percent) of DOPC.

Figure 11A:
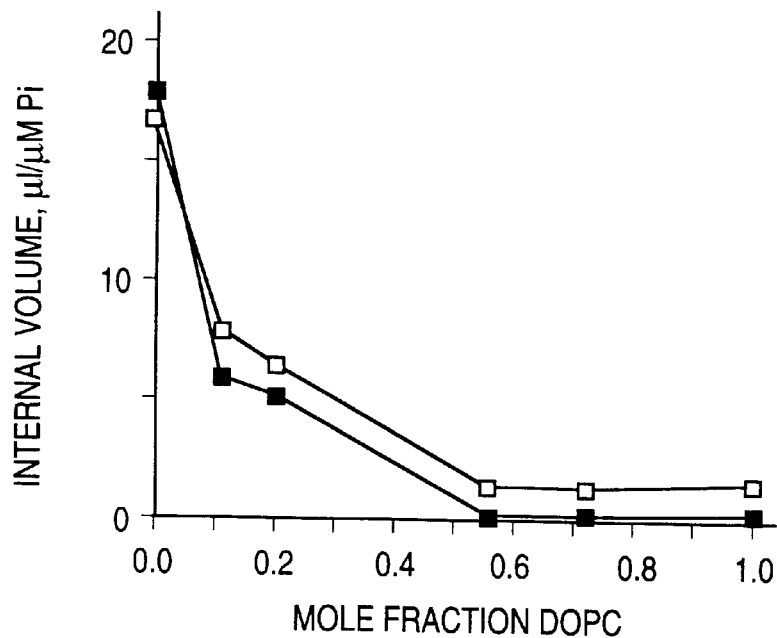
FIG. 11A shows the internal volume of IF liposomes containing varying amounts of DOPC by $^{14}C$ sucrose encapsulation and TEMPONE EPR methods (open squares and closed squares, respectively).

The internal volume of the IF liposomes was measured by the $^{14}$C sucrose encapsulation method and the TEMPONE EPR method, and the results are demonstrated graphically in FIG. 11A.

Figure 11B:
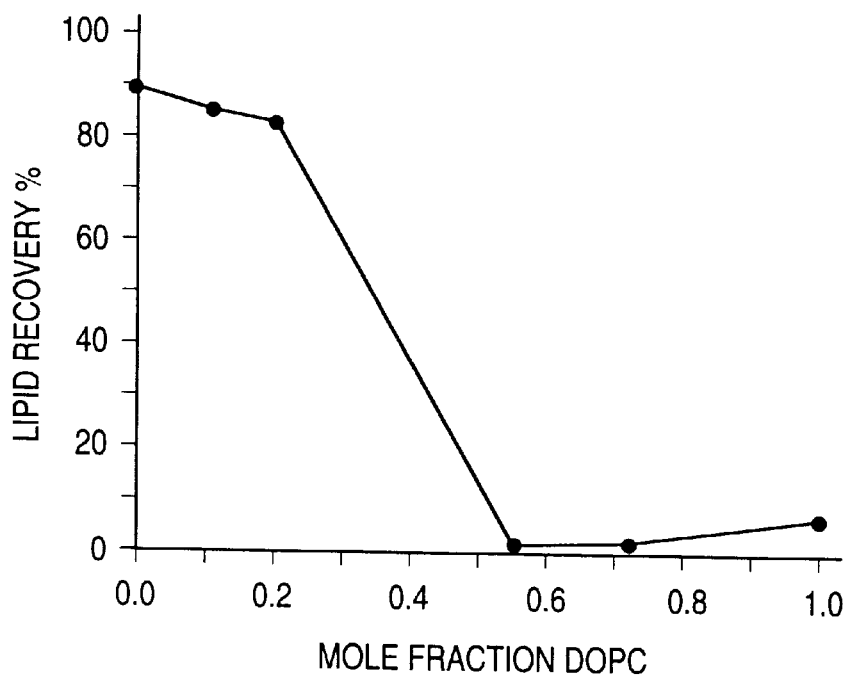
FIG. 11B shows the lipid recovery following the formation of IF liposomes containing varying amounts of DOPC.

As can be seen from the graph, increasing the amount of DOPC decreased the size of the IF liposomes. Even as little as 10% DOPC appeared to reduce the liposome volume by over 50%. Above 0.4 mole fraction (40 mole percent) DOPC the ethanol-lipid gel did not form and the SUVs did not appear to fuse. The internal volumes of the liposomes at 0.6 and 0.8 mole fraction DOPC were 0.2 and 0.24 μl/μM Pi respectively which is in the SUV range. In addition, the percent of lipids recoverable by centrifugation decreased above 0.4 mole fraction DOPC (see FIG. 11B).

Example 19

Entrapment of Radiocontrast Agent Ioversol in DSPC IF Liposomes

DSPC (200 mg, lyophilized powder) was suspended in 5.0 ml distilled water and sonicated to a translucent SUV suspension (time of sonication was about 20 minutes). The SUV suspension was centrifuged for 10 minutes at 10,000×g to pellet the titanium residue: SUVs were decanted from the titanium pellet. Ioversol (Optiray 320®, Mallinckrodt) (11.5 mg), 4.1 ml ethanol, and 1.7 ml distilled water were admixed and 3.3 ml aliquots of this mixture were pipetted into three 15 ml capacity tubes. Aliquots (1.1 ml) of the SUV suspension were added to each tube. The tubes were capped and vortexed vigorously, resulting in a translucent gel.

The tubes were allowed to set at room temperature for one hour, then uncapped and incubated at 70° C. in an immersion bath for one hour with intermittent vortical mixing. Following the incubation, the tubes were $N_2$ sparged by bubbling a gentle stream of $N_2$ through the mixture for about 8 minutes. After cooling the contents to room temperature, buffer (30 mM Tris, 150 mM NaCl, 0.6 mM $Na_2$EDTA, pH 6.7) was added to each tube and mixed by inversion. The unentrapped ioversol was removed by centrifugation washes (3 minutes at 5,000×g) which were repeated 3 times.

The resulting ioversol entrapped in the IF liposomes was assayed spectrophotometrically by absorption at 245 nm and regression against a standard curve of ioversol in ethanol. Lipid concentration was determined by the method of Chen et al. The entrapment results are shown below in Table 6.

TABLE 6

| Sample | mg/ml iodine | mg/ml DSPC | Final Iodine:Lipid |
|--------|--------------|------------|--------------------|
| 1 | 92.1 +/− 7.1 | 14.3 +/− 0.2 | 6.4 (range 5.9–7.0) |
| 2 | 93.2 +/− 8.1 | 13.7 +/− 0.7 | 6.8 (range 5.9–7.8) |
| 3 | 93.2 +/− 9.2 | 13.7 +/− 0.1 | 6.8 (range 6.1–7.5) |

The IF liposomes had a mean diameter of 4.0–5.0 μm determined by Malvern particle size analysis.

Example 20

Entrapment of Radiocontrast Agent Ioxoglate in DSPC IF Liposomes

The materials and procedures of Example 19 were followed thereby entrapping the radiocontrast agent ioxoglate (Hexabrix®, Mallinckrodt) in IF liposomes. Entrapment was assayed according to the methods of Example 19 and the results tabulated in Table 7 below.

TABLE 7

| Contrast Agent | mg/ml Iodine | mg/ml Lipid | Iodine:Lipid |
|----------------|--------------|-------------|--------------|
| Ioxoglate | 6.43 +/− 2.7 | 11.5 +/− 0.3 | 5.2–6.0 |

Example 21

Entrapment of Radiocontrast Agent Iopamidol in DSPC IF Liposomes

The materials and procedures of Example 19 were followed thereby entrapping the radiocontrast agent iopamidol (Isovue®, Bristol-Myers Squibb) in IF liposomes. Entrapment was assayed according to the methods of Example 19 and the results tabulated in Table 8 below.

TABLE 8

| Contrast Agent | mg/ml Iodine | mg/ml Lipid | Iodine:Lipid |
|----------------|--------------|-------------|--------------|
| Iopamidol | 52.3 +/− 5.2 | 12.0 +/− 0.6 | 3.7–5.0 |

Example 22

Effect of Incubation Time on Internal Volume of IF Liposomes

The materials and procedures of Example 12 were followed, using 20 mg/ml DPPC and wherein the ethanol concentration was 3.0 M, wherein the incubation period of the gel at a temperature above and below the Tm was varied. The incubation period was set at 5 minutes, and the internal volume of the resulting IF liposomes was measured by the $^{14}$C sucrose encapsulation method (solid bar), and both the CAT 1 EPR (shaded bar), and TEMPONE EPR method (diagonal bar). The results of the measurements are demonstrated on the histogram of FIG. 12.

The above methods were repeated wherein the incubation periods were 30 minutes, one hour, and two hours. Similarly, internal volume measurements were made and compared.

Figure 12:
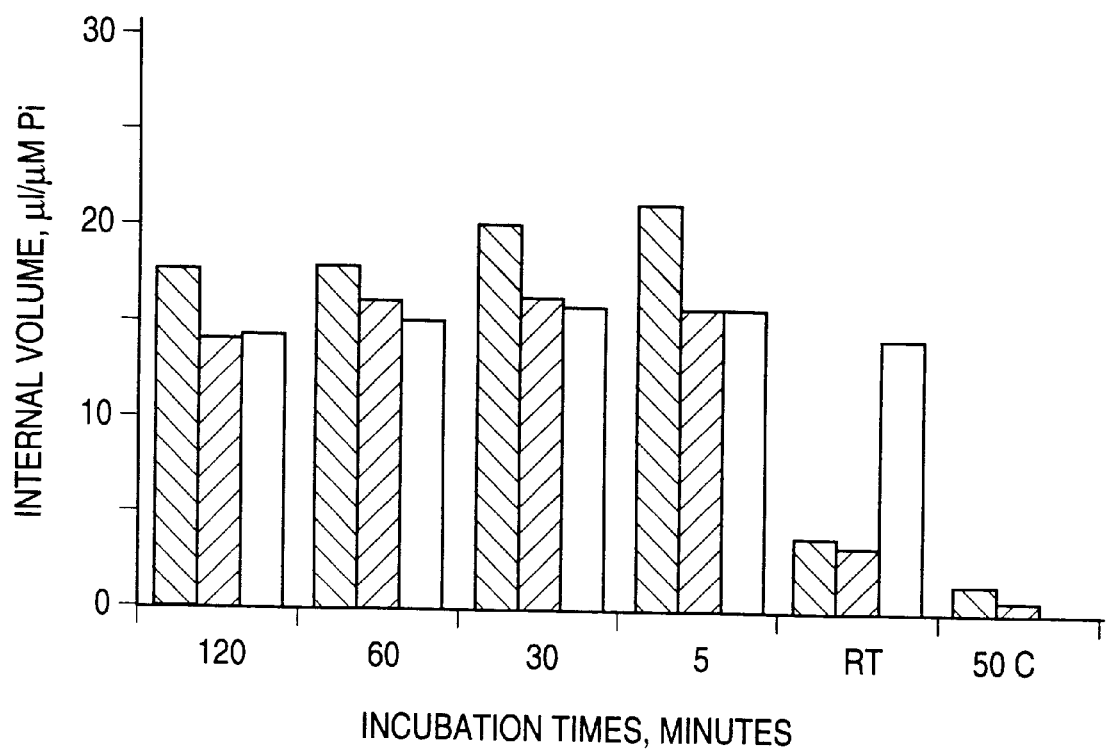
FIG. 12. Histogram demonstrating the effect of lipid incubation time above and below the DPPC Tm (5 minutes, 30 minutes, 60 minutes and 120 minutes), and incubation procedure ("RT", which means room temperature, or 50° C.), on the resulting internal volume of the IF liposomes. Throughout this specification, RT, also designated "RM temp," means 25° C., unless otherwise specified.

As shown by FIG. 12, there appears to be no significant difference in the IF liposome internal volume as a function of incubation time between 5 minutes and 2 hours.

Example 23

Effect of Changing Incubation Procedure on the Internal Volume of IF Liposomes

The materials and procedures of Example 12 were repeated wherein the incubation conditions were varied, e.g., wherein the DPPC SUVs were incubated at room temperature only, without incubation above the DPPC Tm (e.g., at 50–55° C.). The internal volume of the resulting IF liposomes was determined by the $^{14}$C sucrose encapsulation method (solid bars) as well as both the CAT 1 EPR (shaded bars), and TEMPONE EPR methods (diagonal bars), and the results are shown on the histogram as "RT" of FIG. 12.

The above procedure was repeated without room temperature incubation, wherein the ethanol was added and the incubation was conducted at a temperature above the DPPC Tm (50–55° C.). Since the liposomes resulting from this method of incubation did not pellet, rather than centrifugation washes, the liposomes were washed by diluting the DPPC sample 6 fold with 10 ml of Tris/NaCl buffer, removing a 4.0 ml sample, and concentrating this sample with an Amicon 30K microconcentrator (Grace Co.) which was spun for 1 hour at 30,000×g in a Beckman J-2 centrifuge. The sample volume which was retained was concentrated again using the same procedure. The results of this sample are labeled "50° C.".

By reference to FIG. 12, it is apparent that both incubation periods are required for the formation of large IF liposomes.

Example 24

Comparison of Internal Volume of IF Liposomes to MLVs

DPPC (80 mg, powdered form) (Avanti Polar Lipids) was added to 2.00 ml of Tris/NaCl buffer according to the methods of Example 12. The DPPC suspension was sonicated to clarity as described in Example 12. A final concentration of 3.0 M ethanol (addition of 0.43 ml ethanol) was employed thereby forming IF liposomes. The sample was incubated and washed by centrifugation as in Example 12, and the internal volume was determined twice by the CAT 1 EPR methods described in Example 13, the results tabulated in Table 9 hereinbelow.

The above methods of section I were repeated employing 80 mg DPPC in 2.00 ml Tris/NaCl buffer, vortexing at 50–55° C. thereby producing MLVs. However, these MLVs were not sonicated and no ethanol was added.

The identical methods were repeated wherein 40 mg of DPPC was employed. The sample was incubated and washed by centrifugation as in Example 12, and the internal volume was determined twice by the CAT 1 EPR methods described in Example 13, the results tabulated in Table 9 hereinbelow.

The methods of section 11 were repeated wherein 0.43 ml of ethanol for a final concentration of 3.0 M ethanol in the final solution was added. The sample was incubated and washed by centrifugation as in Example 12, and the internal volume was determined twice by the CAT 1 EPR methods described in Example 13, the results tabulated in Table 9 hereinbelow.

Table 9 below illustrates the relatively large internal volume of IF liposomes compared with conventional MLVs or MLVs exposed to relatively high ethanol concentrations.

TABLE 9

| Sample | Lipid Concentration (mg/ml) | 3.0 M EtOH | Internal Volume ($\mu$L/$\mu$M Pi) |
|---|---|---|---|
| DPPC SUVs | 20 | yes | 15.78 |
| DPPC SUVs | 40 | yes | 13.38 |
| DPPC MLVs | 20 | yes | 2.02 |
| DPPC MLVs | 40 | yes | 1.70 |
| DPPC MLVs | 20 | no | 1.37 |
| DPPC MLVs | 40 | no | 0.92 |

Example 25

Iotrolan-DSPC IF Liposomes

The materials and procedures of Example 7 were followed, thus producing an IF liposome population containing iotrolan.

Example 26

Entrapment of Radiocontrast Agent Iopromide in DSPC IF Liposomes

The materials and procedures of Example 21 are followed thus producing IF liposomes containing iopromide.

Example 27

Pressure Induced Interdigitation Fusion Liposomes

Interdigitation fusion liposomes were made using hydrostatic pressure to induce the fusion. These are referred to herein as pressure induced fusion liposomes or "PIFs". Srmall liposomes were made by probe sonicating either 20 mg/ml DPPC MLVs or DSPC MLVs until clear. The resulting small unilamellar vesicles (SUVs) were centrifuged at 3000 g for 5 minutes to remove titanium dust introduced from the probe sonicator. Two to three ml of the SUVs was placed in a Teflon sample holder which was then submerged in the hydraulic fluid inside the high pressure reaction chamber. The temperature of the reaction chamber was brought to the desired value before the sample was placed in it. To vary temperature the reaction chamber was jacketed with flexible tubing through which water circulated from a water bath. Once the sample was loaded the chamber was then closed and hydraulic fluid pumped in to pressurize the sample. Samples were held at pressure for 15 minutes after which pressure was reduced and the sample removed. Sample was then transferred from the Teflon holder to a glass vial and heated to 50° C. (for DPPC) or 70° C. (for DSPC) to ensure reformation of vesicle structure. Liposomes (now PIFs) were allowed to cool and captured volumes measured using a technique described in detail in Perkins, et al. (1988) *Biochim. Biophys. Acta* 943: 103–107, incorporated herein by reference.

Figure 13:
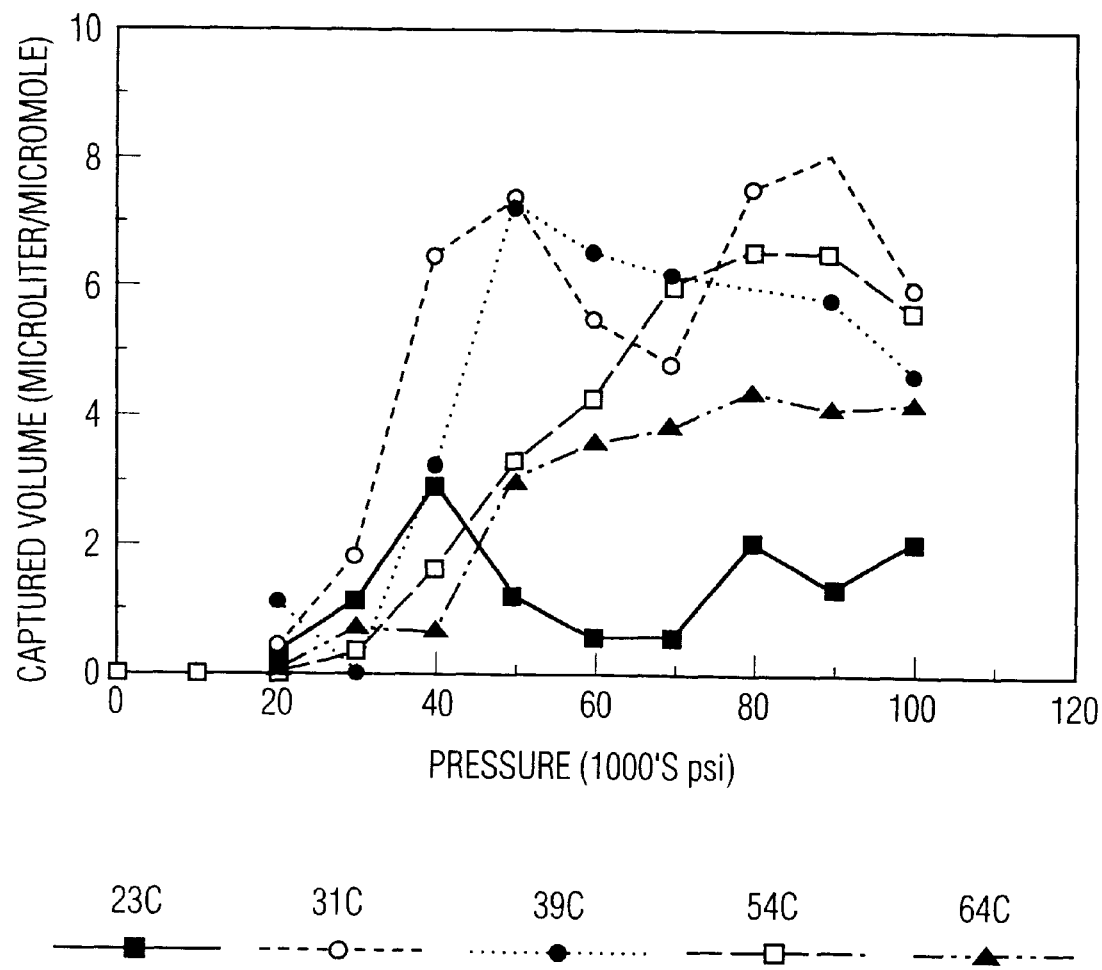
FIG. 13. Graph showing the effect of pressure and temperature on formation of PIF vesicles composed of DPPC. Small DPPC liposomes were placed in Teflon sample holders and the indicated pressures were applied for 15 minutes at the indicated temperatures.
Figure 14:
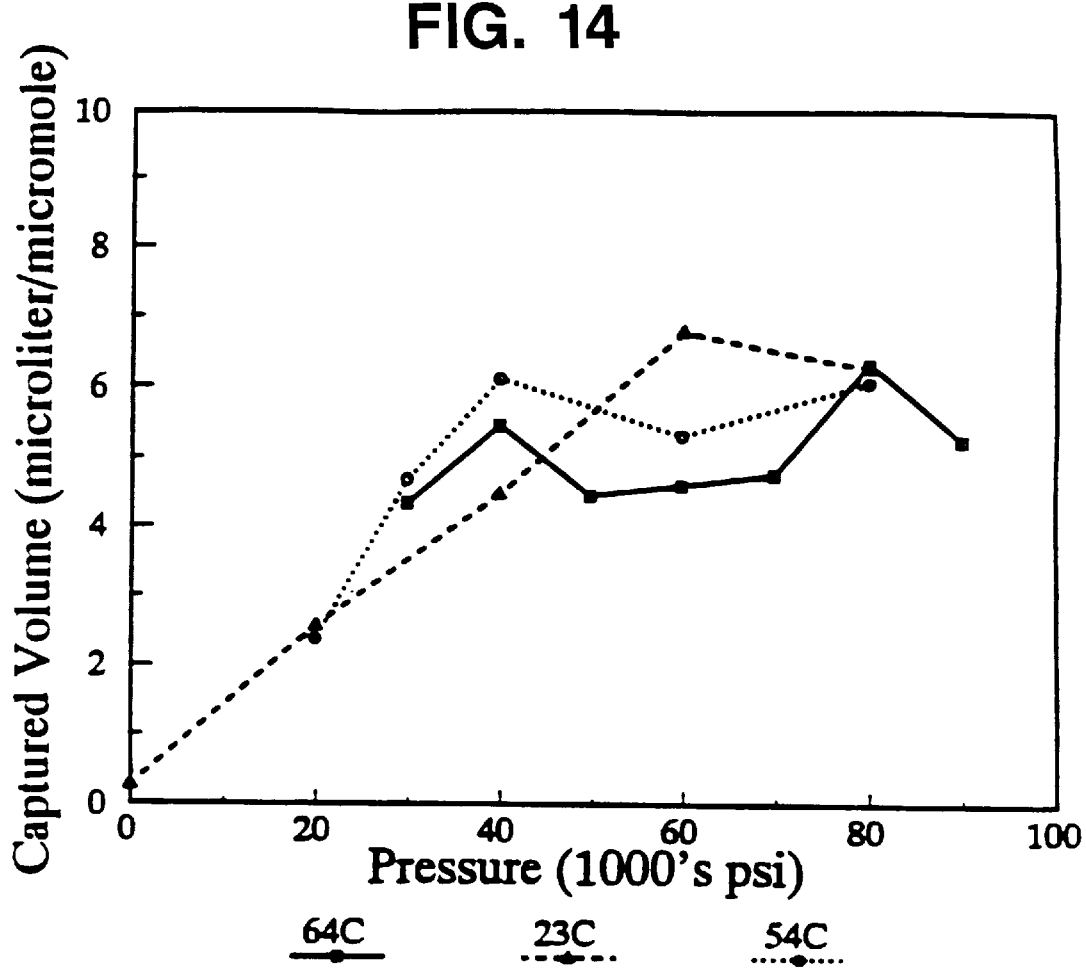
FIG. 14. Graph showing the effect of pressure and temperature on formation of PIF vesicles composed of DSPC. Small DSPC liposomes were placed in Teflon sample holders and the indicated pressures were applied for 15 minutes at the indicated temperatures.

The results are presented graphically in FIG. 13 for the DPPC tests, and in FIG. 14 for the DSPC tests. For DPPC, as shown in FIG. 13, samples pressurized below the phase transition temperature of the lipid (41° C. for DPPC) were gel like in appearance—just like the gels resulting from ethanol addition below the phase transition temperature. The viscous nature of these samples disappeared after they were heated above 41° C. For DSPC, as shown in FIG. 14, samples pressurized below the phase transition temperature of the lipid (54° C. for DSPC) were gel like in appearance. The viscous nature of these samples disappeared after they were heated to 70° C. In both cases, heating resulted in transformation from interdigitated sheets to liposomes.

Example 28

Post Gel Incorporation of Lipid-Soluble Molecules into Interdigitation-Fusion Liposomes The interdigitation-fusion (IF) technique can also be applied to SUVs composed of two or more lipid components, rather than the single lipid component systems. The IF technique is very effective at producing large liposomes if both lipids in the SUVs can undergo ethanol-induced interdigitation. For example, large interdigitation-fusion vesicles (IFVs) were produced from either DPPC/DMPC SUVs or DPPC/DPPG SUVs, if the temperature was such that both lipid components undergo ethanol-induced interdigitation.

The internal volume results from the DPPC/DPPG SUV mixture are shown in FIG. 15. As shown in the figure the internal volume of IFVs formed from DPPC/DPPG SUVs did not change significantly as the mole fraction DPPG was increased. The IF technique as described in Example 1 was used to form these IFVs, and the total lipid concentration for each experiment was 30 mM, The ethanol-induced DPPC/DPPG gel state was formed at room temperature. The internal volume of the product IFVs were measured with both $^{14}$C-sucrose encapsulation and the EPR probe TEMPONE, as previously described.

In contrast to the DPPC/DPPG SUV experiment, the addition of a non-interdigitating lipid such as DOPC or cholesterol to DPPC SUVs significantly inhibited the formation of large IFVs. The internal volume of IFVs formed from DPPC/DOPC and DPPC/cholesterol SUVs are shown as a function or mole fraction DOPC or cholesterol in FIG. 16. The internal volumes of the product liposomes were measured using the EPR probe TEMPONE. The internal volume of the product liposomes were reduced by 50% when the DOPC content in the DPPC/DOPC SUVs reached 10 mole percent. SUVs that were over 50 mole percent DOPC did not fuse to form the interdigitated membrane sheets required for IFV formation. Cholesterol was particularly effective at disrupting the IF technique. The IFV internal volume was significantly reduced even for DPPC/cholesterol SUVs which contained as little as 2 to 5 mole percent cholesterol.

Therefore, the effectiveness of the IF technique for producing high internal volume liposomes was significantly reduced when non-interdigitating lipids were included in the SUVs prior to interdigitation fusion. Non-interdigitating lipids, such as DOPC and cholesterol, inhibited the ethanol-induced bilayer interdigitation which is required to induce SUV fusion and formation of the interdigitated membrane sheets. This effect presents a problem for preparing large IFVs which have lipids which do not interdigitate.

However, in accordance with the present invention, a modification of the basic IF technique was developed to more efficiently introduce non-interdigitating lipids into IFVs. This IF technique modification comprises adding the non-interdigitating lipid after the ethanol-induced interdigitated membrane sheets or "gel" state is formed. Typically, SUVs containing the non-interdigitating lipids are mixed into the ethanol/phospholipid gel prior to raising the temperature above Tm. The SUVs which contain the non-interdigitating lipids fuse with the phospholipid sheets when the temperature is raised above the Tm of the phospholipid membrane sheets. This IF technique modification will be referred to herein as "post-gel" incorporation, because the extra lipids were added after the ethanol/phospholipid "gel" state was formed.

In addition, this post-gel incorporation technique can be used to incorporate into IF vesicles any material which would normally interfere with the IF process. That is, certain materials which it may be desirable to incorporate into IF vesicles, such as bioactive materials, may interfere with the IF process, and therefore not be otherwise usable. The present post-gel incorporation process allows the incorporation of these interdigitation-fusion interfering materials into IF vesicles. This process is particularly suited for hydrophobic or amphipathic materials which are lipid soluble. Bioactive materials which may desirably incorporated into IF vesicles are described elsewhere in this specification.

Even though DMPC is a saturated phospholipid. incorporation of DMPC SUVs into an DPPC IFVs at room temperature is a good example of the post-gel lipid incorporation. Since the Tm for DMPC is 23° C., ethanol will not induce interdigitation in DMPC bilayers at room temperature. DMPC prevented the formation of large IFVs when the ethanol was added to DPPC/DMPC SUVs at room temperature. However, large IFVs were formed when ethanol was added to DPPC/DMPC SUVs at 5° C. Thus mixing in DMPC to DPPC SUVs inhibited the IF technique at room temperature, but not at 5° C. However, relatively large DPPC/DMPC IFVs were formed at room temperature even at 1:1 DPPC/DMPC mole ratio if the DMPC was added to the sample after the formation of the ethanol/DPPC gel state.

Evidence for post-gel state mixing of DMPC SUVs into DPPC IFVs is shown in FIG. 2. FIG. 2B shows the average internal volume for pure DPPC IFVs which were formed according the procedures described in the earlier examples. In addition, DPPC/DMPC 1:1 mole ratio IFVs which were formed following the three different modified versions of the standard IF technique. The bar labeled "5° C." and "RT" indicate the internal volume of IFVs which formed from DPPC/DMPC 1:1 mole ratio SUVs in which the ethanol/lipid gel state was formed at 5° C. and room temperature respectively. The bar labeled "post" indicates the internal volume of DPPC/DMPC 1:1 mole ratio IFVs which were formed at room temperature using the post-gel incorporation modification.

Figure 18:
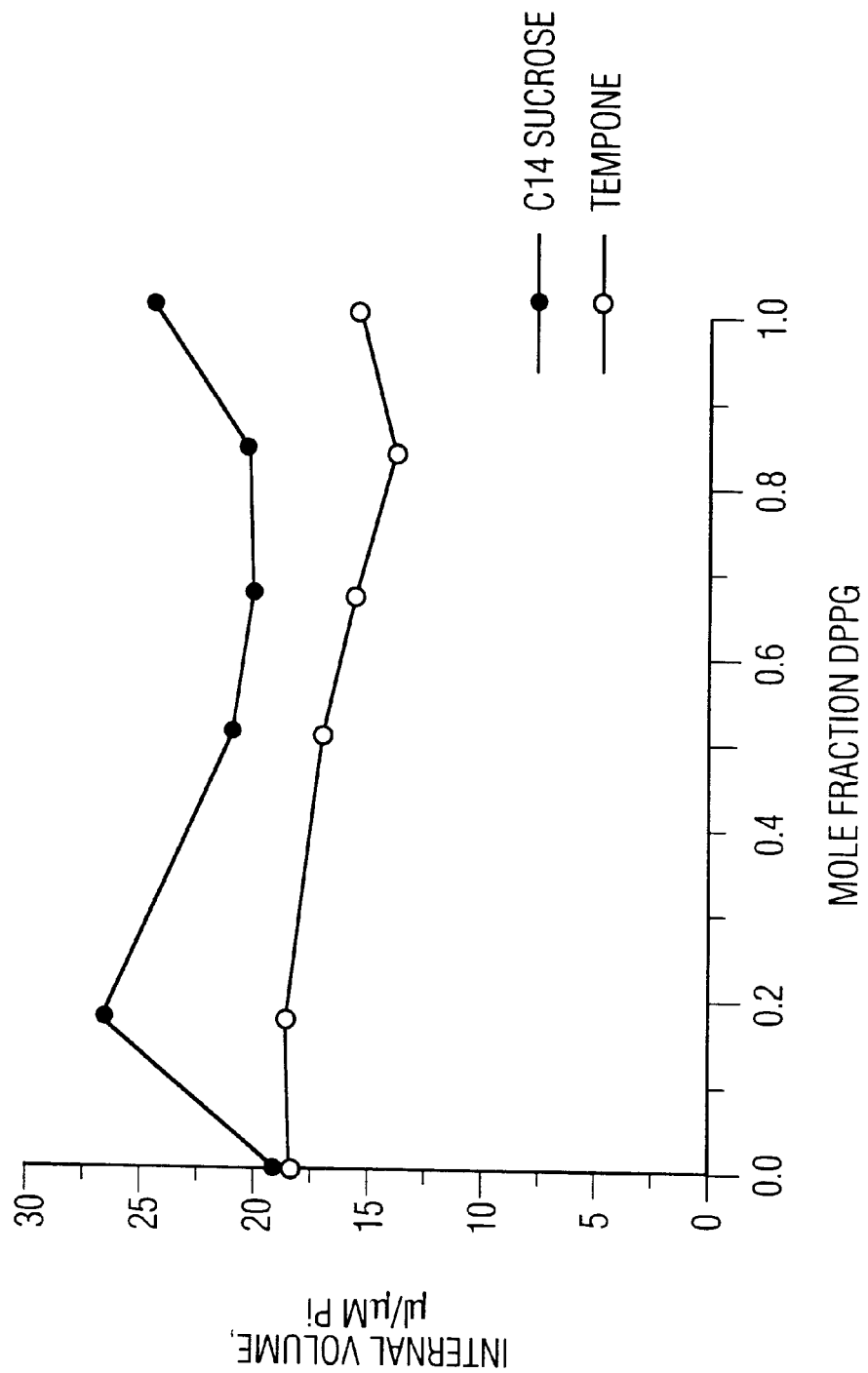
FIG. 18. Graph showing the effect of the mole fraction of DPPG on the internal volume of large DPPC/DPPG interdigitation-fusion vesicles (IFVs).

As shown by the results presented in FIGS. 17, the addition of DMPC SUVs to the ethanol-induced DPPC gel state did not inhibit the formation of large IFVs. In order to demonstrate that the DMPC was incorporated into the IFVs, the phase transition behavior of the DPPC/DMPC IFVs was examined. FIG. 18 shows the membrane fluidity of DPPC, DMPC, and DPPC/DMPC IFVs as a function of temperature. The membrane fluidity was measured with the EPR probe TEMPO according to the method of Wu and McConnell. The gel state formation temperatures for the DPPC and DMPC IFVs were at room temperature and 5° C. respectively. The DPPC/DMPC curve labeled "5° C." was formed from DPPC/DMPC at 1:1 mole ratio SUVs at 5° C. The DMPC for the DPPC/DMPC curve labeled "post" was added at room temperature as DMPC SUVs after the ethanol-induced DPPC gel state was formed. The main phase transition temperatures for the DMPC and DPPC IFVs were at 23 and 39° C. respectively. The Tm for DPPC IFVs was 39° C. which is slightly below the established Tm for DPPC. DPPC and DMPC are completely miscible in both the gel and liquid-crystalline phases, forming an ideal mixture. The phase transition temperature for DPPC/DMPC 1:1 mole ratio IFVs for which the gel was formed from 1:1 mole ratio DPPC/DMPC SUVs at 5° C. was at 30° C. which is consistent with established values for 1:1 mole ratio DPPC/DMPC MLVs. The Tm for the DPPC/DMPC IFVs that were formed by the post-gel IF modification was also at 30° C. which indicates that the mole ratio of these DPPC/DMPC IFVs was also 1:1. This demonstrates that most of the DMPC SUVs were incorporated into the DPPC IFVs during the 50–55° C. incubation.

Figure 19:
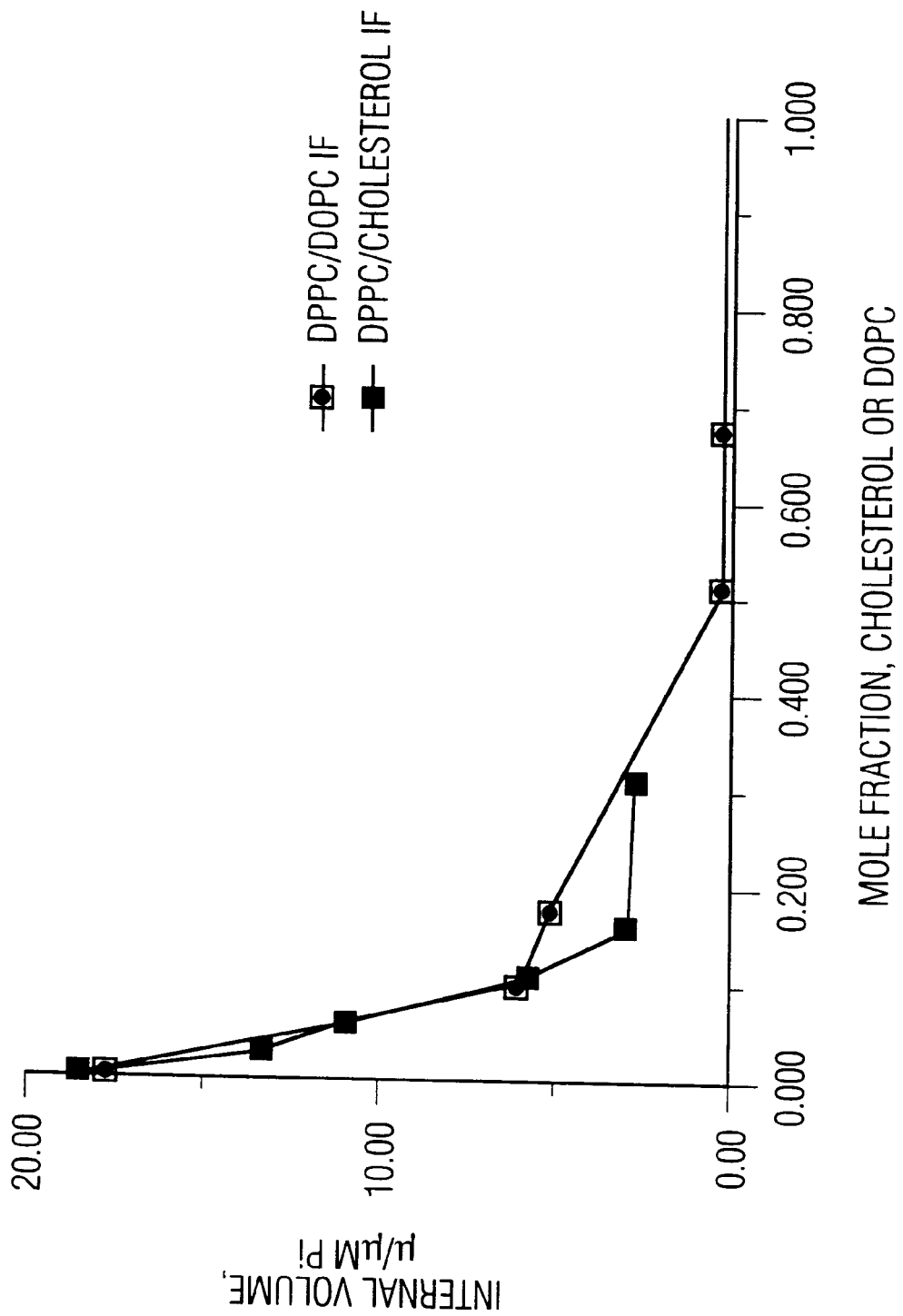
FIG. 19. Graph showing the effect of the addition of DOPC or cholesterol on the internal volume of large DPPC interdigitation-fusion vesicles (IFVs).
Figure 20:
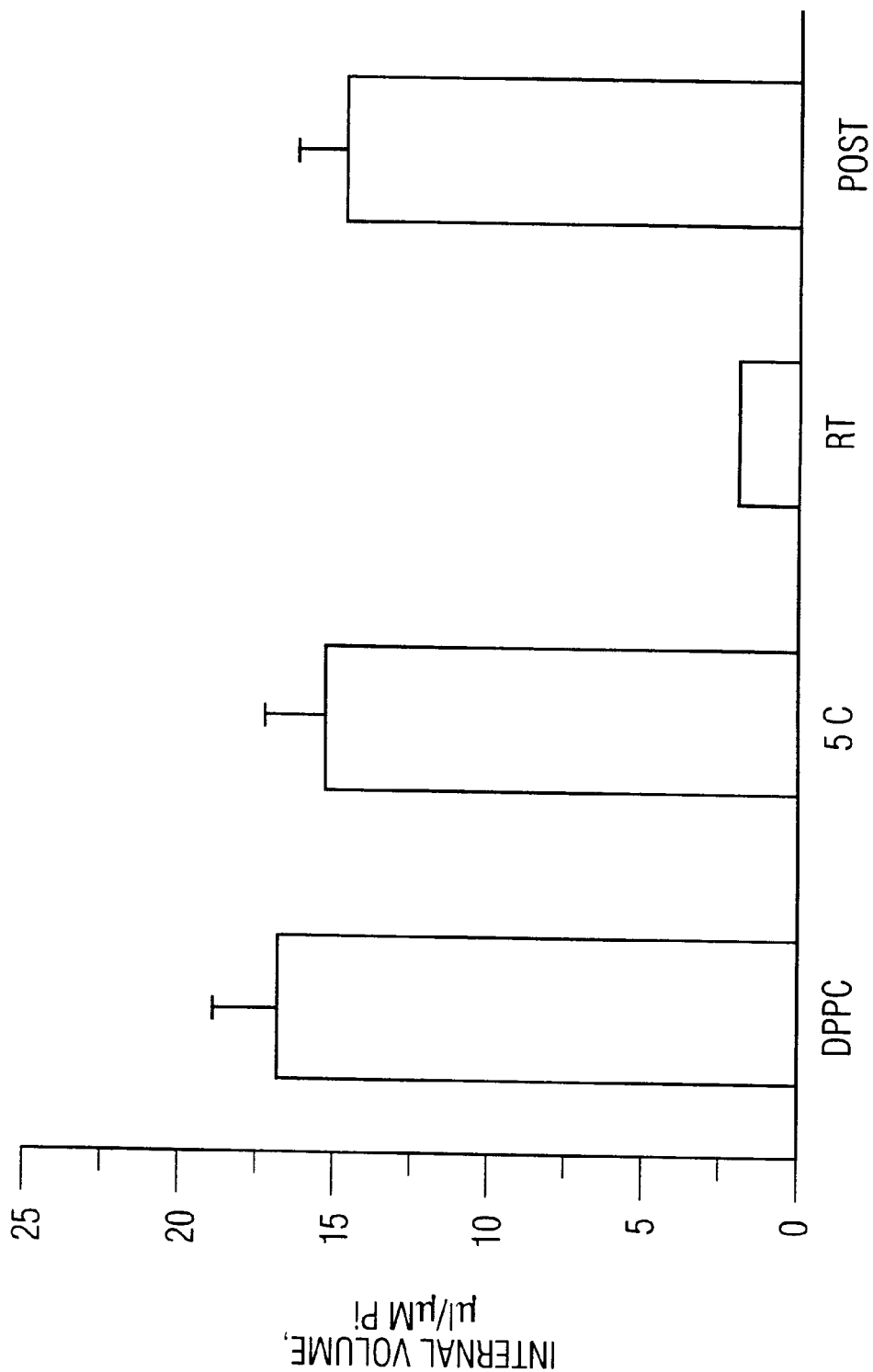
FIG. 20. Graph showing the effect of post-gel incorporation of DMPC SUVs on the internal volume of large DPPC IFVs.
Figure 21:
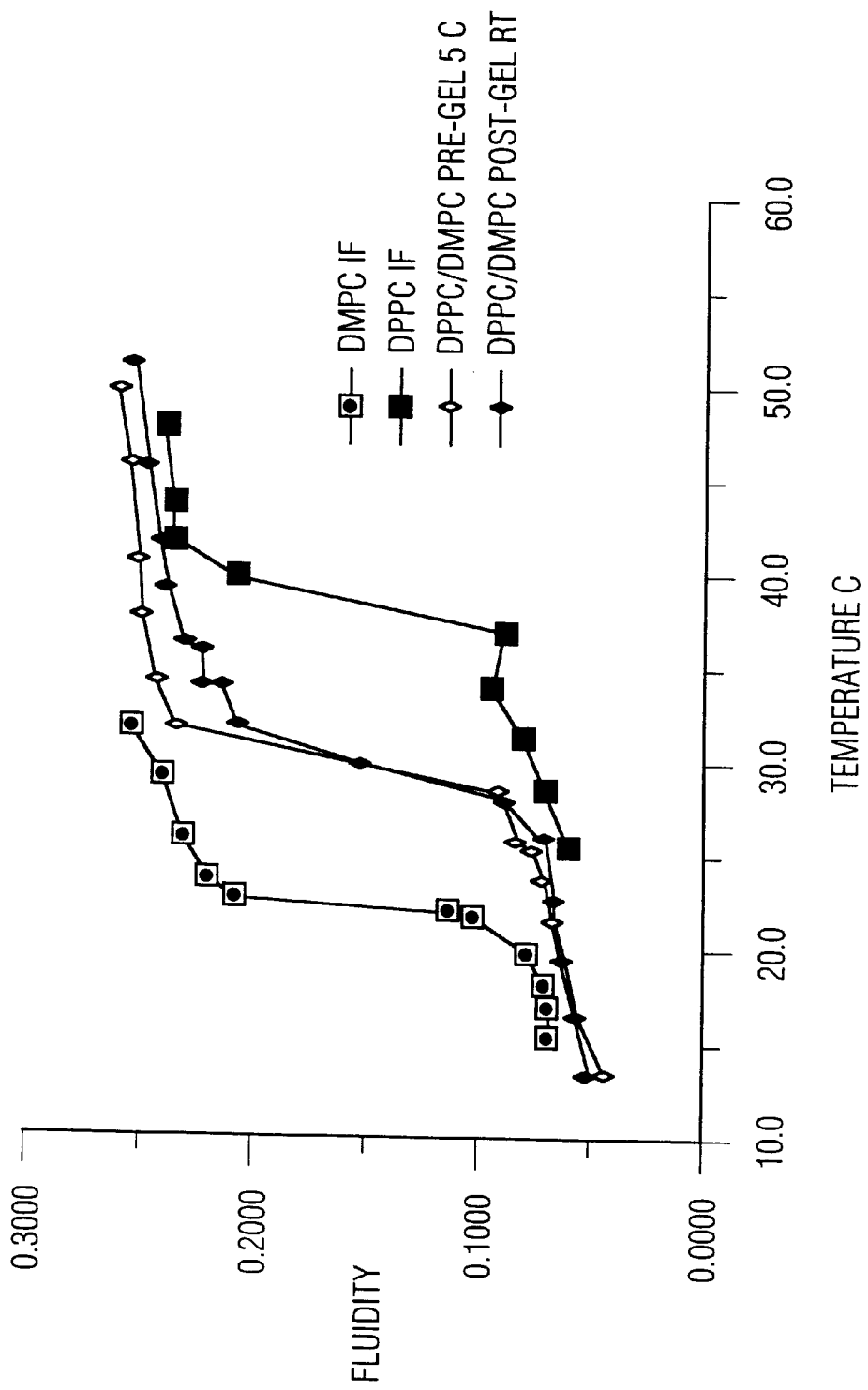
FIG. 21. Graph showing the effect of temperature on the membrane fluidity of various DMPC, DPPC, and DPPC/DMPC IFVs.
Figure 22:
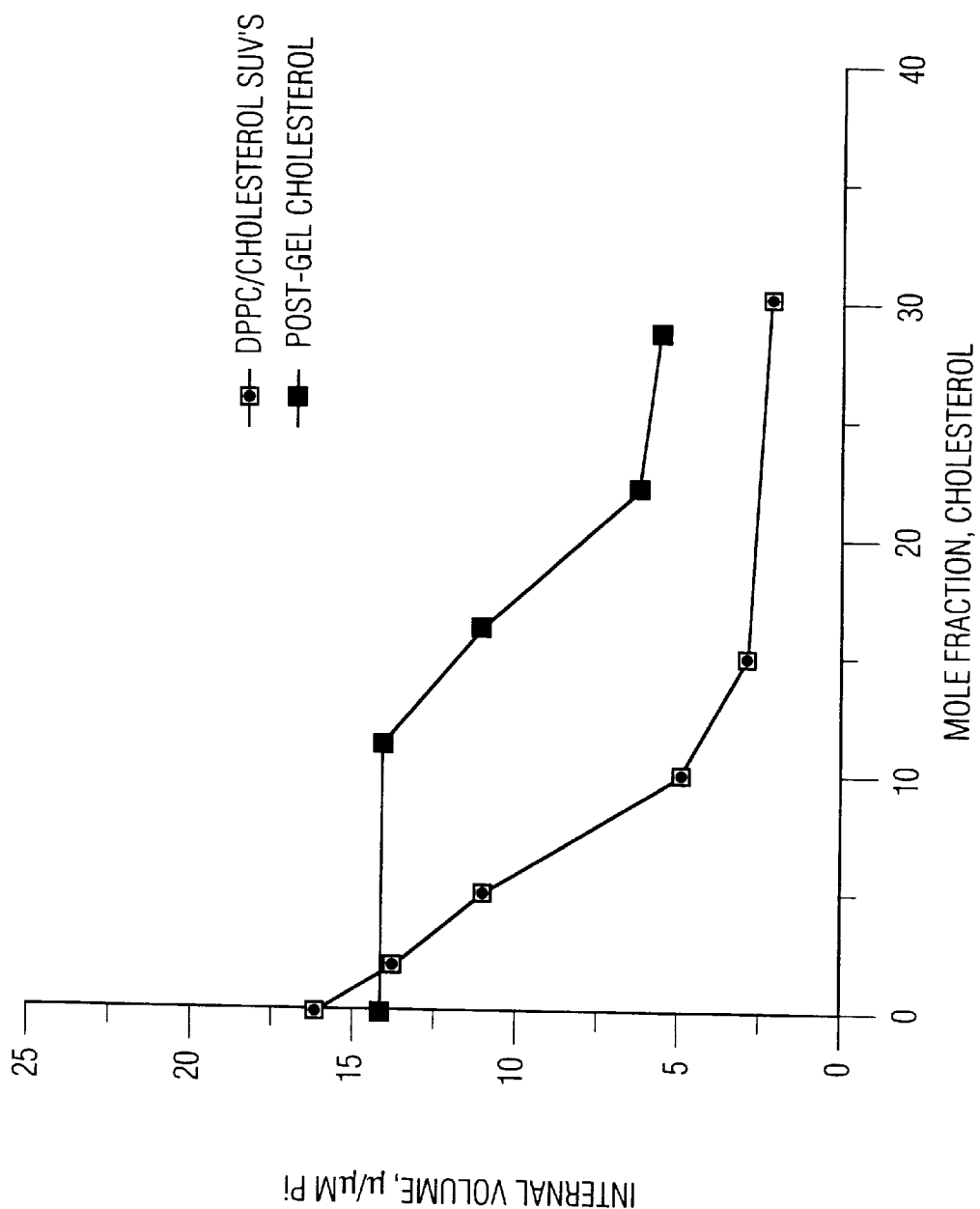
FIG. 22. Graph showing the effect of post-gel incorporation of cholesterol on the internal volume of large DPPC IFVs.
Figure 23:
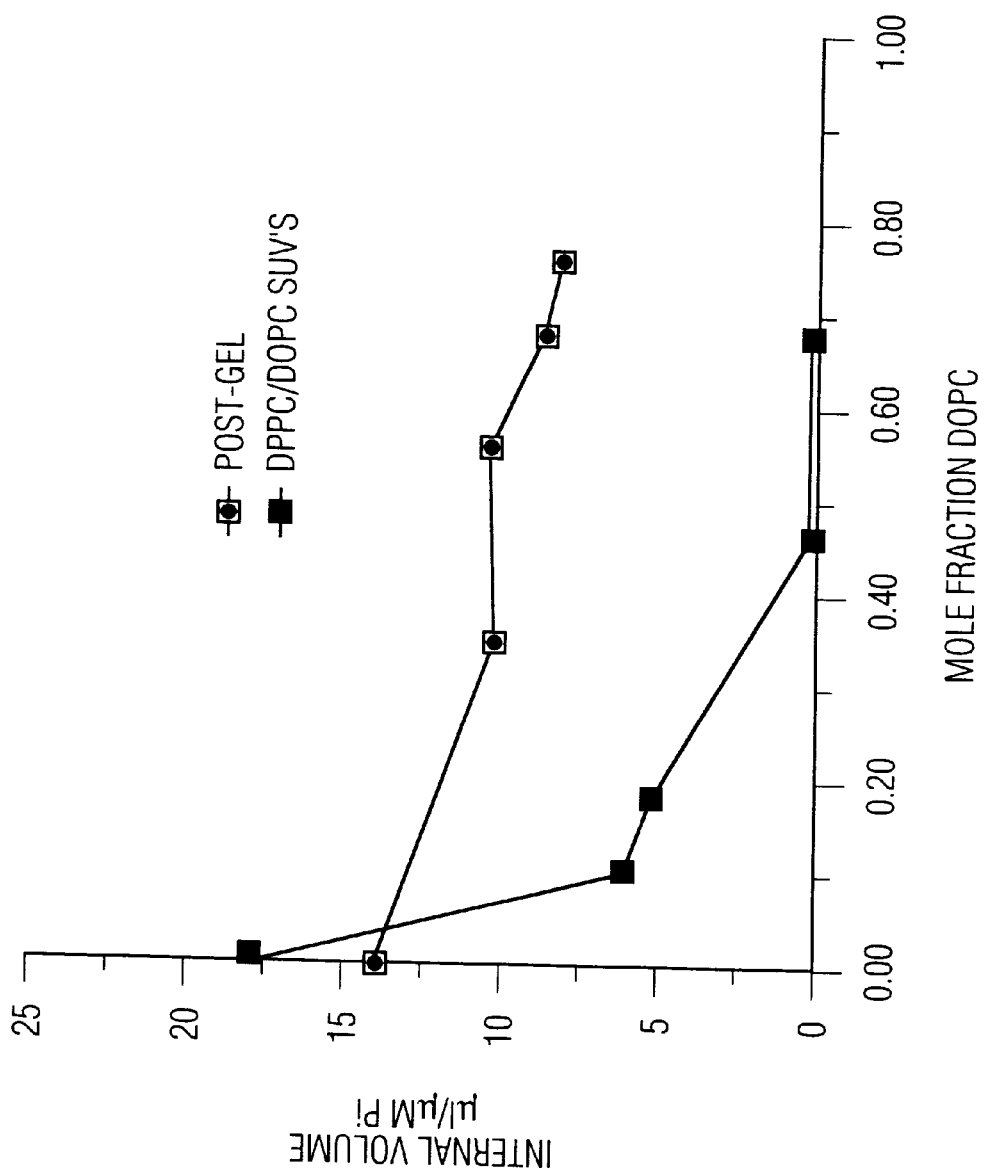
FIG. 23. Graph showing the effect of post-gel incorporation of DOPC SUVs on the internal volume of large DPPC IFVS.

Non-interdigitating lipids that do not mix in an ideal manner can also be mixed into DPPC IFVs. FIG. 19 shows the internal volume of DPPC cholesterol IFVs that were formed by mixing the cholesterol into the sample after the ethanol-induced DPPC gel state was formed. The internal volume as a function of mole fraction cholesterol recovered in the product DPPC/cholesterol IFVs is shown in this figure. The cholesterol content in the IFVs was determined using radiolabeled cholesterol. For comparison the internal volumes of DPPC/cholesterol IFVs formed form DPPC/cholesterol SUVs are also shown in FIG. 19. FIG. 20 shows results for a similar experiment where the non-interdigitating lipid DOPC was mixed into DPPC IFVs using either the post-gel IF modification or the standard IF technique using DPPC/DOPC SUVs. The DOPC content was determined using radiolabeled DOPC. This figure illustrates that incorporating non-interdigitating lipids into the sample after the interdigitated membrane sheet were formed significantly increased the internal volume of mixed lipid IFVs.

Typical second lipids which may be able to be incorporated into interdigitation-fusion liposomes formed of a first lipid by this post-gel incorporation method include, but are not limited to, cholesterols, tocopherols, egg PC, POPC, DOPC, DMPC, DPPE, egg PE and fatty acids. These are all lipids which are either non-interdigitating or which have a transition temperature (Tm) below room temperature. By this method, as much as 90% of these lipids may be incorporated into IFVs formed of an interdigitating lipid. Therefore the weight ratio of the first lipid to the second lipid may be as low as 10:90. On the other hand, the amount of the second lipid which may interfere with the interdigitation-fusion process may be as low as 0.1% of the first lipid. Therefore the ratio of the first lipid to the second lipid may be as high as 99.9:0.1.

Example 29

High Pressure Sterilization

Vegetative bacteria, specifically those of the genus Bocillus are known to be extremely resistant to a variety of environmental stresses including high temperatures and pressures. Indeed it has long been known that pressures higher than 1000 MPa are needed to inactivate bacterial spores (Larson et al. (1918)). Therefore, spore suspensions of *Bacillus subtilis* ATCC strain 6633 were plated on blood agar (Remel) and used as the seed culture for all of the sterilization studies. Colonies from the agar were grown in trypticase soy broth (Remel) to the early stationary phase. These cultures contained $7.7 \times 10^7$ viable bacteria per milliliter, as measured by growth on blood agar.

Cultures that were subjected to high pressures were placed in Teflon® polytetrafluoroethylene tubes with screw caps (Swage Lok) and placed in the high pressure reactor chamber. The pressure on the reactor was then increased to the desired point (High Pressure Equip. Co., PS 150 pumping system) and time at that pressure was then monitored. At the completion of the incubation, the sample was plated on blood agar, and viable colonies were counted after 15 hours of growth.

FIGS. 15, 16 and 17 show the effects of high pressures on *B. subtilis* at 40, 50 and 60° C. respectively. Each data point is the average of at least 3 to 9 separate determinations. Error bars are not shown because they are usually smaller than the symbol used to denote the point, Sterility is determined by the lack of growth on blood agar. On the graphs, two consecutive points with a value of 0 show the time required to confidently reach sterility. At 40° C. sterility could be achieved only after 90 minutes at 80,000 psi. This time is reduced to 30 minutes at 50° C. Although strictly speaking the log of 0 is undefined, for the purposes of presenting the present data, the log of 0 has been graphed as 0.

In order to ascertain that the presence of lipid has no protective effect on the bacteria, and that the presence of bacteria do not affect the formation of the interdigitated phase, samples of DPPC SUVs were mixed with 100,000 viable bacteria. The mixture was then subjected to sterilizing pressures. Sterilization was found to be effective, and the captured volume of the resultant PIF liposomes was not affected by the presence of bacteria. Therefore, these results indicate that high hydrostatic pressures may be of use in sterilizing liposomal preparations.

Further tests were conducted to demonstrate that high pressure may be used to sterilize liposomal products other than those involving pressure induced fusion vesicles. Multilamellar egg phosphatidylcholine (EPC) liposomes containing gentamicin were formed in accordance with the methods set forth in Lenk et al., U.S Pat. No. 4,522,803, incorporated herein by reference. A sample of this material was subjected to 90,000 psi pressure for 60 minutes at a temperature of 50° C. This sample, as well as an untreated control sample were then centrifuged to separate free from bound gentamicin. The supernatants were assayed to determine free gentamicin, ant the liposomes were resuspended and assayed for liposomal associated gentamicin. The unpressurized control sample was found to have 0.723 mg/ml of non-liposomally associated gentamicin, and 6.687 mg/ml of liposomally associated gentamicin. The pressurized test sample had corresponding values of 0.744 mg/ml of non-liposomally associated gentamicin, and 7.234 mg/ml of liposomally associated gentamicin. The data indicate that these pressure and temperature conditions do not adversely effect the association of gentamicin with EPC liposomes.

Example 30

Formation of Interdigitation-Fusion Vesicles

Figure 24A:
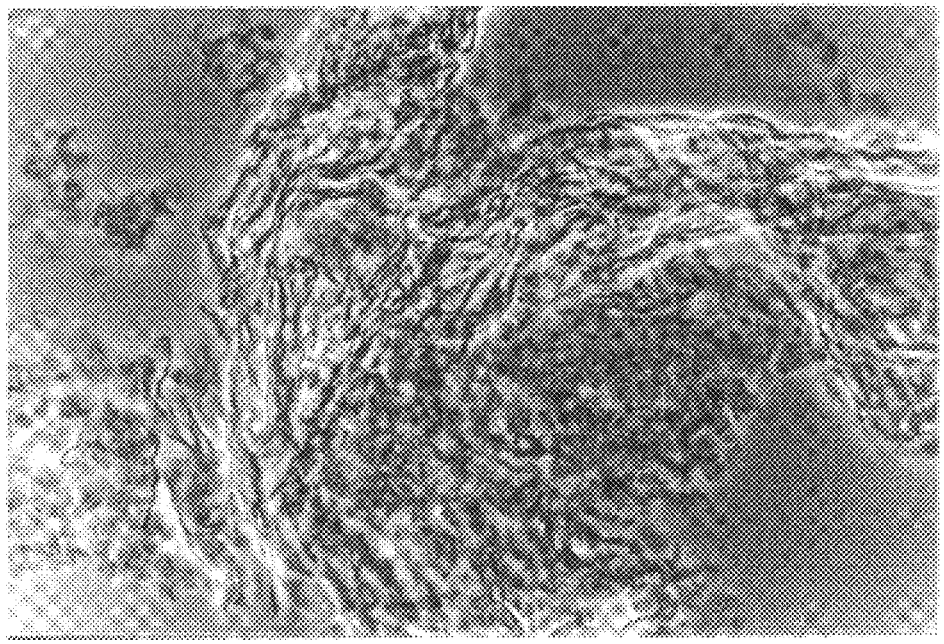
FIG. 24. Phase contrast photomicrographs of the ethanol-induced DPPC interdigitated sheets and DPPC IFVs. A. Photomicrographs (400×) of ethanol-induced DPPC interdigitated sheets formed at 20 mg/ml (3.0M ethanol, 150 mM NaCl, 10 mM Tris-HCl, pH 7.2, room temperature). The sheet suspension was then disrupted by a five-fold dilution with 3.0M ethanol NaCl/Tris buffer. B. Photomicrograph (400×) of 20 mg/ml DPPC IFVs in 3.0M ethanol NaCl/Tris buffer at room temperature. The IFVs were formed from ethanol/DPPC interdigitated sheets by raising the sample temperature above the Tm of the DPPC. The scale bars in both micrographs indicate 10 microns.
Figure 24B:
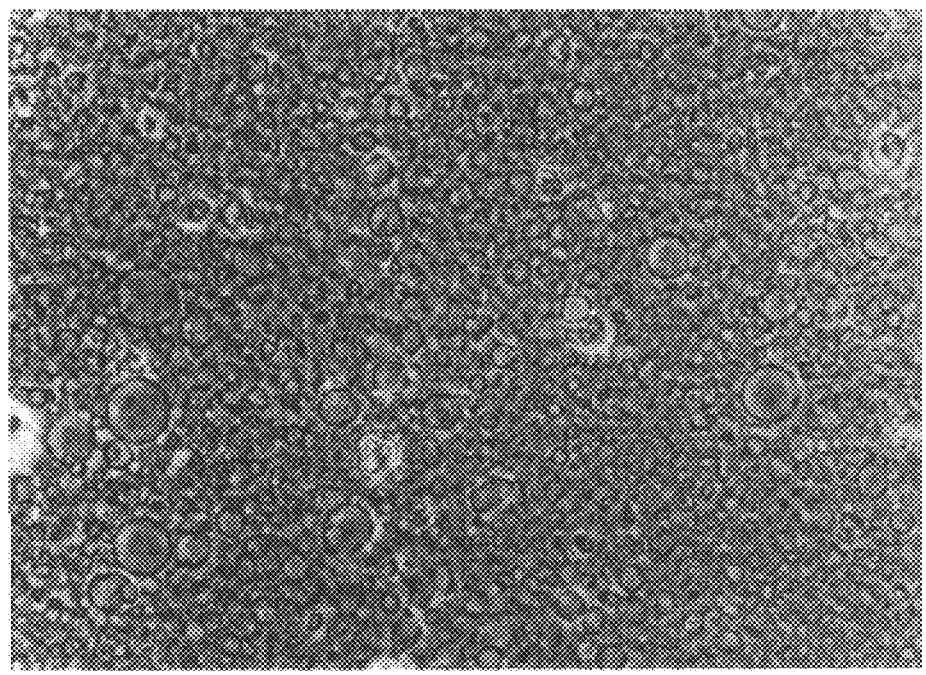
Figure 25A:
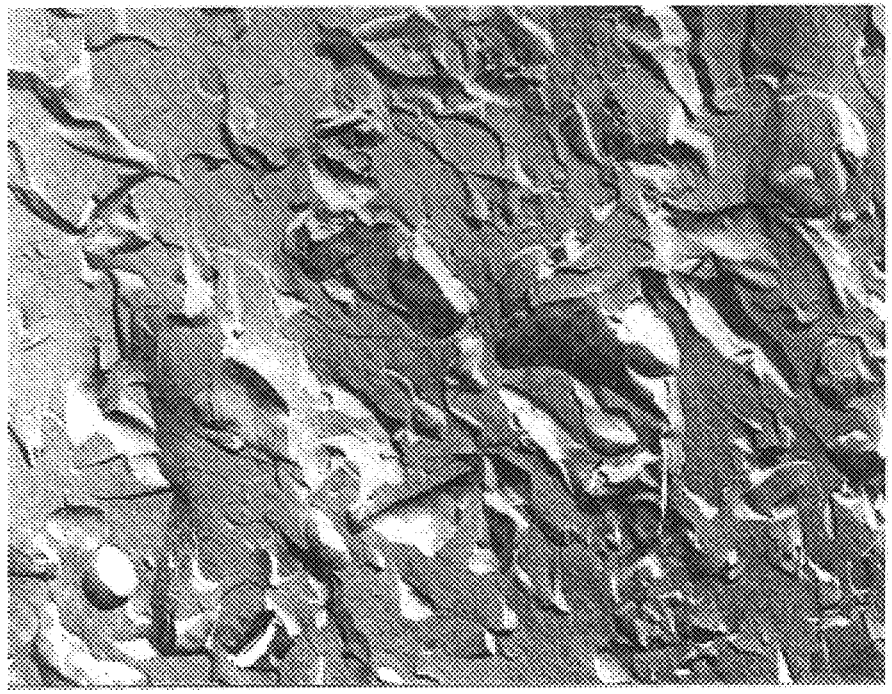
FIG. 25. Freeze-fracture electron micrographs of ethanol-induced DPPC interdigitated sheets and DPPC IFVs. A. Ethanol-induced DPPC interdigitated sheets (2.5M ethanol, 150 mM NaCl, 10 mM Tris/HCl, pH 7.2, room temperature). B. DPPC IFVs formed by incubation of the interdigitated sheets above the Tm of DPPC. The scale bars indicate 1 micron.
Figure 25B:
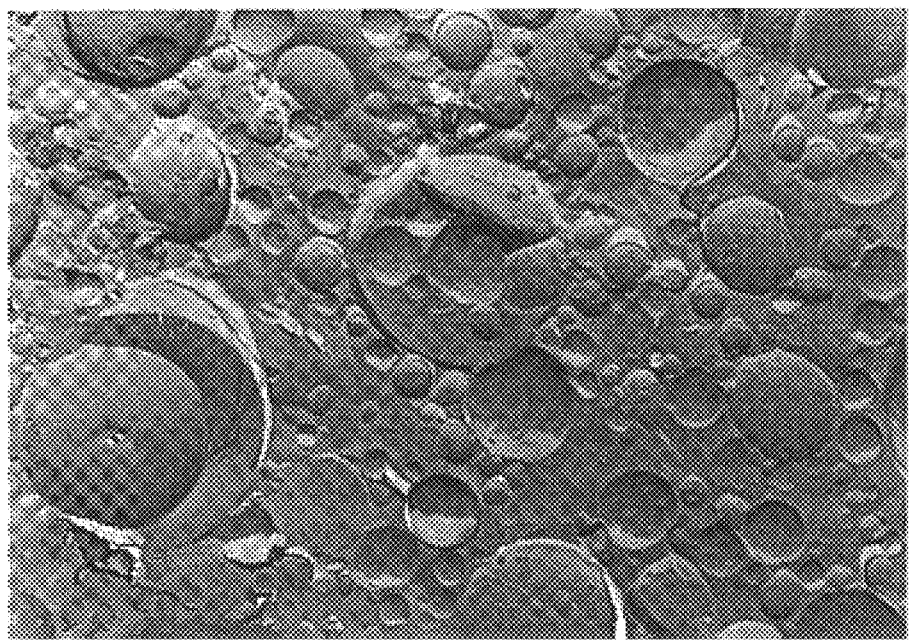

Interdigitation-fusion vesicles (IFVs) can be formed from phospholipids or combinations of phospholipids which undergo interdigitation, such as DPPC or DSPC, e.g., by inducing interdigitation-fusion of small unilamellar vesicles (SUVs) comprising such phospholipids. The coalescence of DPPC SUVs into interdigitated sheets, and the transformation of these sheets into IFVs, is shown in FIGS. 24 and 25 by optical phase contrast microscopy and freeze-fracture electron microscopy, respectively. Optical phase contrast microscopy was carried out using a Leitz Laborlux D microscope in combination with a Wild MPS45 exposure meter. Kodak GC 135-24 color print film was used to record the images. The samples were observed at room temperature. Freeze-fracture electron microscopy was carried out by sandwiching a 0.1 to 0.3 microliter aliquot of sample between a pair of Balzer copper support plates (Nashua, N.H.) and then rapidly plunging the sample from room temperature into liquid propane. Samples were fractured and replicated on a Balzers BAF 400 freeze-fracture unit at minus 115 degrees Celsius with a vacuum of $4 \times 10^{-7}$ mbar. Replicas were floated off in 3N nitric acid and washed in a series of Clorox solutions. The replicas were viewed and photographed in a Philips 300 electron microscope at magnifications of between 6,000× and 27,000×.

Figure 26:
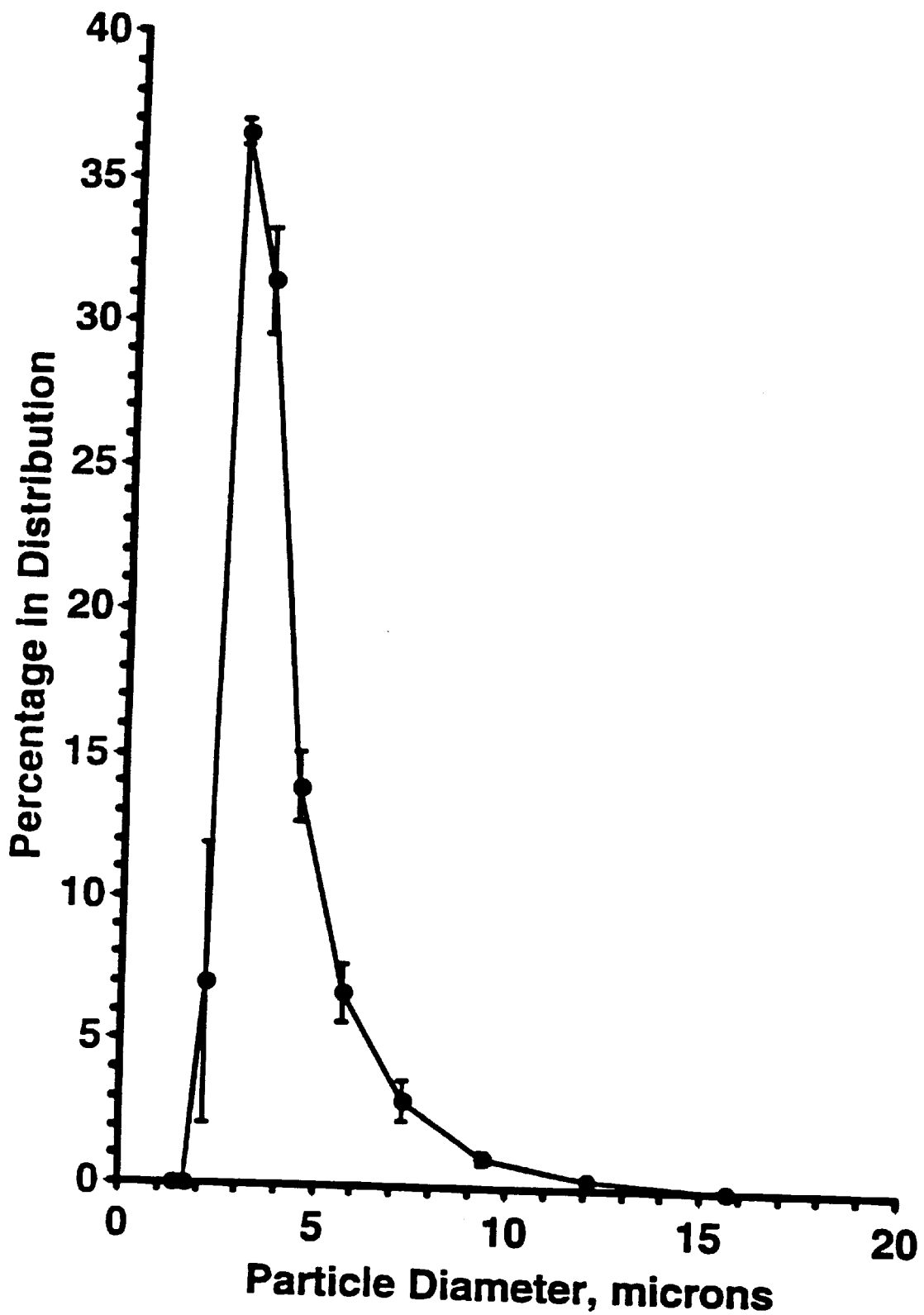
FIG. 26. Size distribution of DPPC IFVs. The normalized diameter distributions for three DPPC IFV samples were measured at room temperature using a Malvern 3600ER laser diffraction particle sizer. The distributions are based upon particle number and were calculated by that instrument. Average values and standard deviations for the Three samples are shown. The number averaged diameter for the samples was 3.54+/−0.12 microns. The IFVs were formed from DPPC SUVs at 20 mg/ml using 4.0M ethanol.

Formation of interdigitated sheets from the DPPC SUVs occurred immediately upon the addition of ethanol. The optically clear SUV suspension was quickly transformed into an opaque, highly viscous fluid. The interdigitated sheets that comprised this opaque suspension had dimensions on the order of hundreds of microns as indicated in FIG. 24a. Raising the temperature above the Tm of DPPC quickly transformed the interdigitated sheets into relatively large unilamellar vesicles. The number averaged size distribution of DPPC IFVs formed at 20 mg/ml with 4.0M ethanol is shown in FIG. 26. The distribution was relatively homogeneous, with most of the liposomes being in the 2 to 6 micron range. The internal volume of the DPPC IFV preparations, averaged to obtain the data shown in FIG. 26, was 20.2+/−0.2 $\mu l/\mu M$ while the NMR lamellarity measurements indicated 44.3+/−12.5 of the DPPC was in the outer monolayer of the liposomes. This corresponds to a statistical lamellarity of 1.13+/−0.32. Thus, the DPPC IFVs were predominantly unilamellar.

The effects of varying ethanol concentration, precursor vesicle diameter, and lipid concentration upon the internal volume of DPPC IFVs are shown in FIG. 27. FIG. 27a shows the effect of varying the concentration of ethanol used to produce the interdigitated sheets from the DPPC SUVs. The internal volume was measured using the ESR spin probe CAT-1 as previously described. For ethanol concentrations of 3.0M and above, the DPPC IFVs were separated from the solvent by centrifugation. At ethanol concentrations of 2.0M and below, the liposomes were separated from the solvent by filtration through a Whatman 0.02 micron Anotop 25 filter (Whatman, Inc., Clifton, N.J.). This filter was chosen because the cationic spin probe CAT-1 does not bind to it.

The internal volume of DPPC IFVs increased linearly from ethanol concentrations of 2.0M to 4.0M. There was no significant difference in either average particle diameter or the lamellarity of DPPC IFVs formed at 2.0M ethanol compared with those formed at 4.0M. This suggests that the observed internal volume increase was due to differences in the shapes of the liposomes. IFVs were not formed efficiently at ethanol concentrations greater than 5.0M.

Figure 27B:
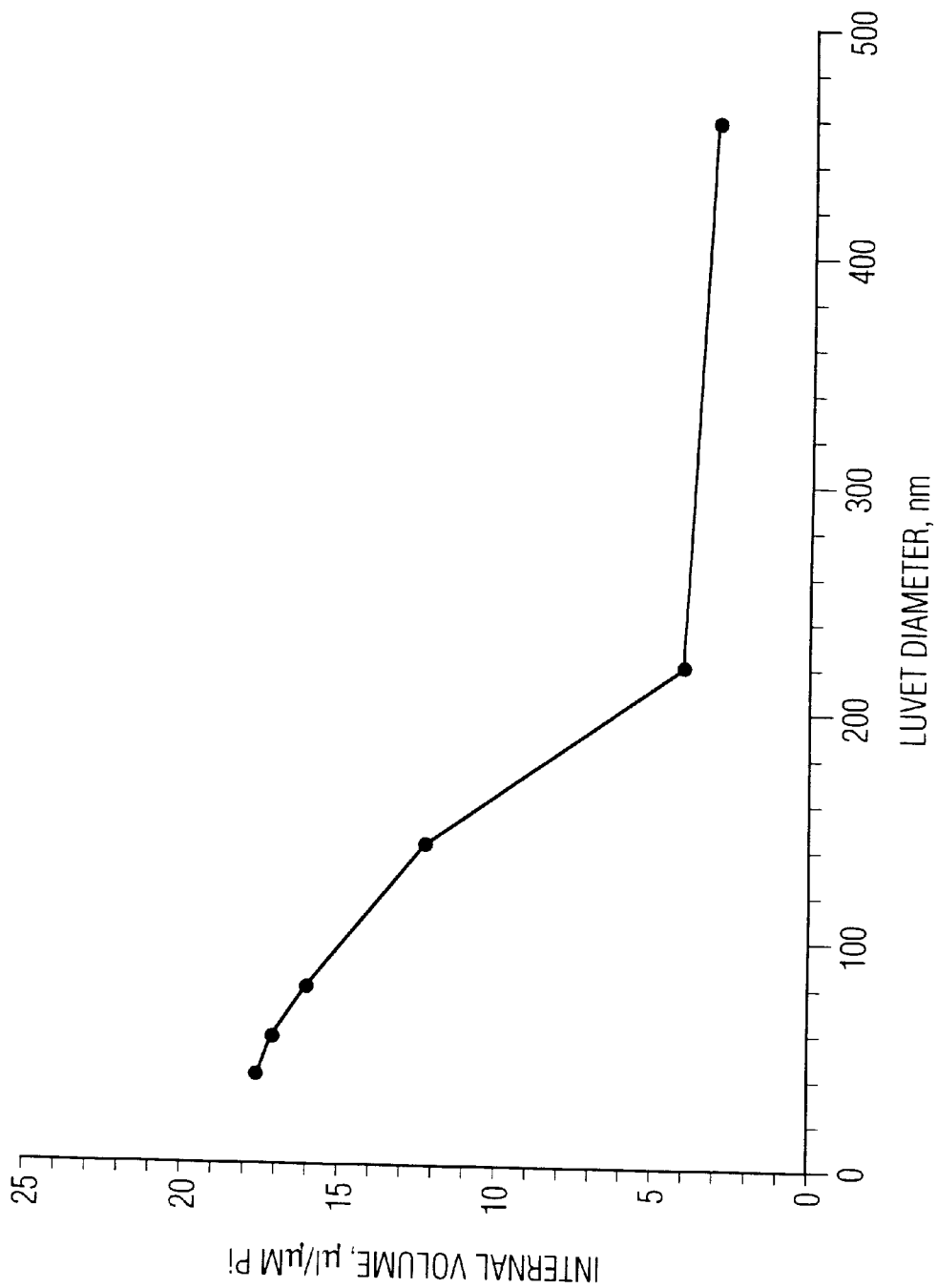
FIG. 27. Effect of interdigitation-fusion parameters on the internal volume of DPPC IFVs. A. Internal volume as a function of ethanol concentration. For ethanol concentrations greater than or equal to 2.0M, the DPPC IFVs were formed by direct addition of ethanol to DPPC SUVs at 20 mg/ml. At 1.5M or less, ethanol was prediluted before addition to avoid mixing artifacts. Error bars indicate standard deviations. B. Internal volumes of DPPC IFVs formed from DPPC LUVETS of various diameters are shown. The LUVETS were prepared by extruding previously formed MLVs through two polycarbonate filters. Diameters were determined by quasi-electric light scattering. C. Internal volumes of DPPC IFVs formed at different DPPC SUV concentrations. Interdigitation-fusion was induced with 4.0M ethanol.

FIG. 27b shows how the interdigitation-fusion process depends upon the diameters of the precursor DPPC liposomes. The ethanol concentrations in the experiments whose results are summarized in the Figure was held at 4.0M, which appeared to be near the optimum concentration for obtaining high internal volumes with DPPC SUVs. The diameter of precursor DPPC LUVETs was determined by quasi-electric light scattering using a Malvern 3600 E laser diffraction particle sizer (Malvern Instruments, Malvern, England). The measurements were made at room temperature with highly diluted samples. The number weighted particle diameter distribution was calculated by the instrument rom the laser diffraction pattern. Precursor vesicles below 100 nm yielded DPPC IFVs of having the largest internal volumes. Large IFVs were not observed unless the diameter of the precursor vesicles was 150 nm or less. Vesicles 200 nm or more in size were relatively ineffective as precursor liposomes.

Figure 27C:
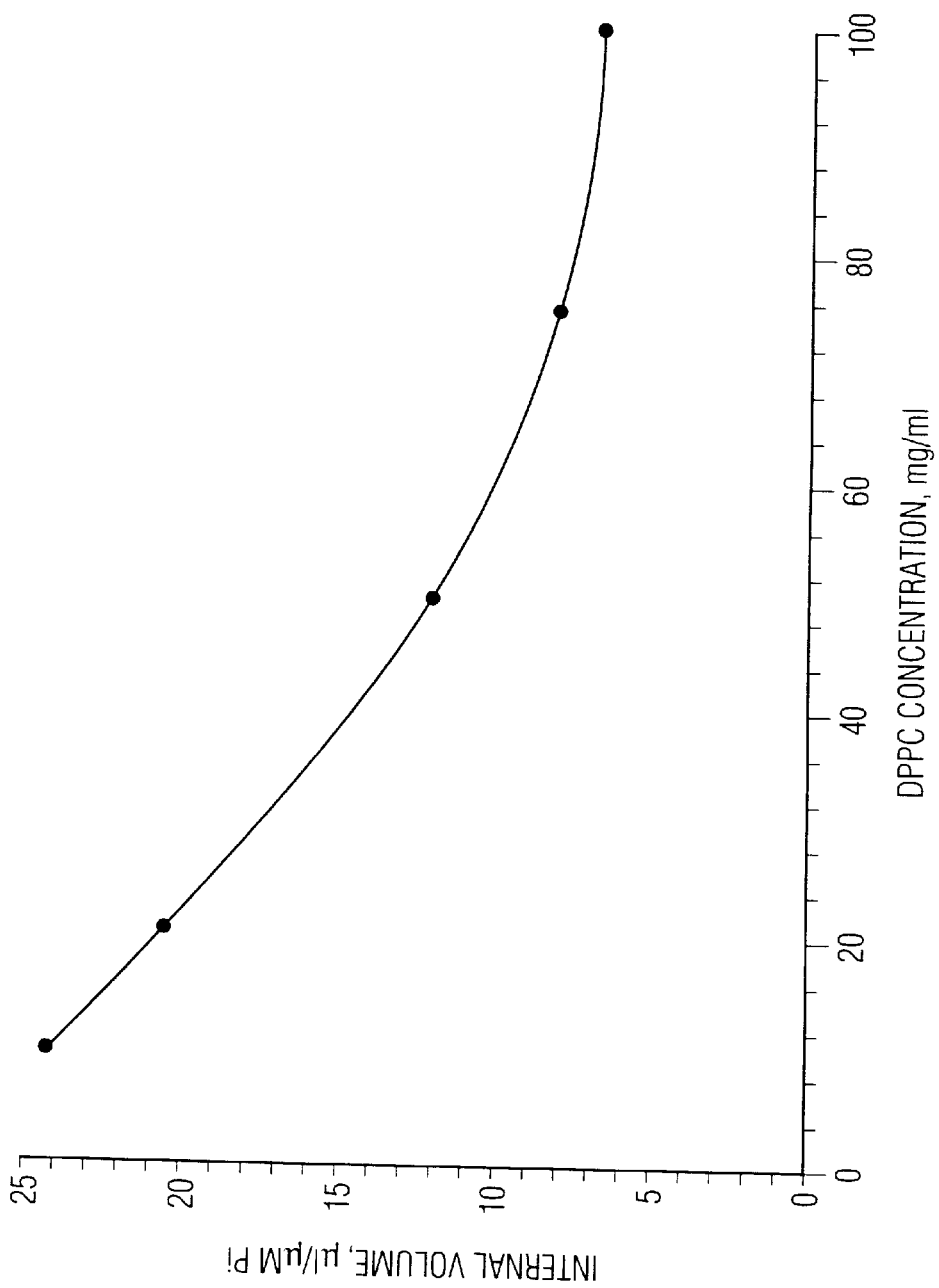

The effect of initial DPPC SUV concentrations on the internal volumes of the IFVs formed at 4.0M ethanol is shown in FIG. 27c. As indicated, the internal volume decreased as the lipid concentration in the interdigitated sheet suspension was raised above 10 mg/ml. At higher lipid concentrations, the vesicles can be expected to be tightly packed as the ratio between internal and external aqueous volumes becomes limiting. The packing problem resulted in a significant lamellarity increase for the DPPC IFVs formed at high lipid concentrations. The statistical lamellarity for DPPC IFVs formed at 100 mg/ml was 2.9, in comparison to a value of 1.1 for DPPC IFVs formed at 20 mg/ml.

Using parameters optimized for DPPC, IFVs were produced using a variety of saturated phospholipids (DMPC, DHPC, DSPC and DAPC (Avanti Polar Lipids, Alabaster, Ala.)), IFVs were typically prepared in 4 ml batches using a lipid concentration of 20 mg/ml. Samples containing two lipids were prepared at 30 mM total lipid. The vesicles were prepared in containers such as scintillation vials or tubes with caps. An SUV suspension of the desired phospholipid was transferred into the container. DPPC, DSPC, DHPC and DAPC samples were equilibrated at room temperature, while DMPC, DOPC, and EPC samples were cooled to between 4 and 6 degrees Celsius. An isothermal volume of absolute ethanol was added to bring the final ethanol concentration in the sample up to 4.0M. The samples were then immediately vortexed. This procedure quickly transformed the transparent SUV suspension into an extremely viscous opaque white suspension of phospholipid sheets. The ethanol addition step was modified when the final ethanol concentration used to induce interdigitation was 1.5M or less. For such samples, equal volumes of the SUV samples at 40 mg/ml and a buffer/ethanol solution at twice the desired final ethanol concentration were mixed. This procedure was required to avoid having locally high ethanol concentrations in the SUV sample before it could be completely mixed. This effect produced a high internal volume mixing artifact at the low ethanol concentrations. No difference in the internal volume of the DPPC IFVs formed at the 2.0M ethanol concentrations was observed between the direct addition of the ethanol versus the addition of prediluted ethanol.

After ethanol addition, the samples were sealed and incubated at room temperature for 15 minutes, except for the DMPC, DOPC and EPC samples, which were incubated at 4–6 deg. C. The caps on the samples were loosened and the samples were then incubated for another 30 mn . at the same temperature above the Tm. DMPC, DOPC and EPC samples were incubated at 40–45 degrees C. DPPC and DHPC samples were incubated at 50–55 deg. C, while DSPC and DAPc samples were incubated at 70–75 deg. C. The ethanol was typically removed by a two-step procedure involving first sparging the samples by bubbling a gentle nitrogen stream through the sample above the lipids Tm. The samples were then washed three times at room temperature by 15 min. centrifugation at 12,000 g using a Sorvall RE5B centrifuge (DuPont Instruments, Wilmington, Del.) using a Sorvall SA-600 rotor. This was sufficient to rapidly pellet the IFVs. Typically, 90–100% of the initial phospholipid was recovered in the IFV pellet when 3.0–4.0M ethanol was used to prepare the interdigitation-fusion sheets. The IFV pellet was subsequently resuspended in NaCl/Tris buffer at a concentration near 20 mg/ml and stored at room temperature. IFV phospholipid concentrations were determined by a modified Bartlett assay ((Bartlett, J. Biol. Chem. 234:466 (1959)).

The same general procedures were used to prepare IFVs from two phospholipids. Ethanol was added below the Tm of the mixture; the high temperature incubation was also performed above the Tm of the mixture.

Incorporation of cholesterol into DPPC IFVs was done by adding 1:1 molar ratio DPPC/Chol SUVs in 4.0M ethanol to DPPC interdigitated sheets also at 4.0M ethanol. The interdigitated DPPC sheets were prepared from DPPC SUVs at a concentration of 30 mM using 4.0M ethanol, according to previously described procedures. DPPC/Chol SUVs in 4.0M ethanol were mixed into the interdigitated sheets at room temperature in such a manner as to give the desired Chol:DPPC mole ratio with a final lipid concentration of 30 mM. The mixtures were then incubated for 45 min. at 50–55 deg. C and sparged with nitrogen above the lipid Tm for 5 minutes to remove the ethanol. Since the size of the product DPPC/Chol IFVs decreased with increasing cholesterol concentration, the centrifugation/wash step was omitted. Control experiments showed that omitting this step did not affect the final internal vesicle volume.

Figure 28:
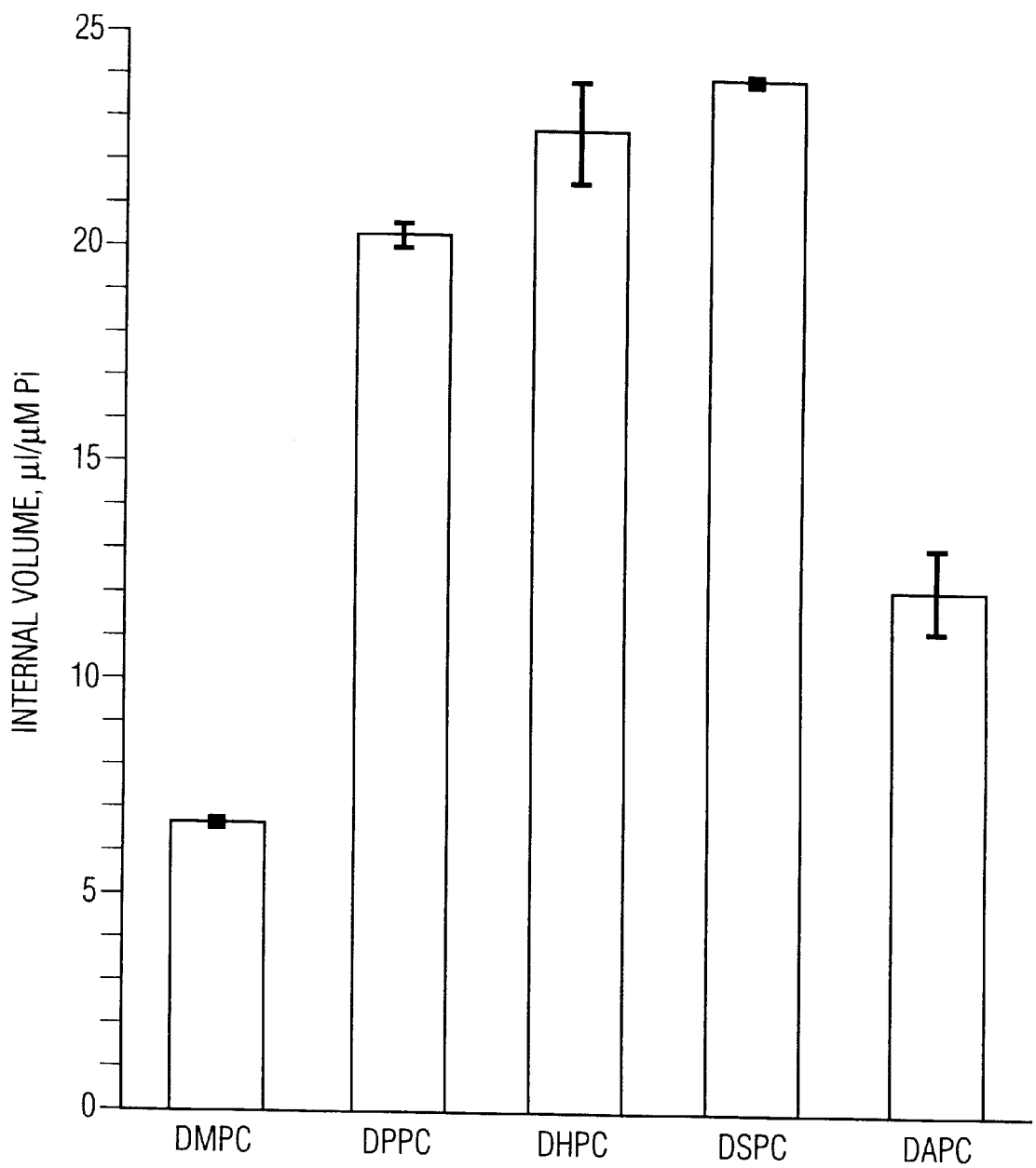
FIG. 28. Internal volumes of IFVs made from various saturated acyl chain phosphatidylcholines. Average internal volumes are shown for DMPC, DPPC, DHPC, DSPC and DAPC IFVs which were prepared from SUVs at 20 mg/ml using 4.0M ethanol to induce interdigitation-fusion. Error bars indicate the standard deviations.

FIG. 28 shows the internal volumes of IFVs produced from DMPC, DPPC, DHPC, DSPC and DAPC SUVs. The internal volumes of vesicles formed from phospholipids which do not undergo ethanol-induced interdigitation-fusion, e.g., EPC and DOPC, were less than 1 microliter/$\mu$M Pi.

Figure 29:
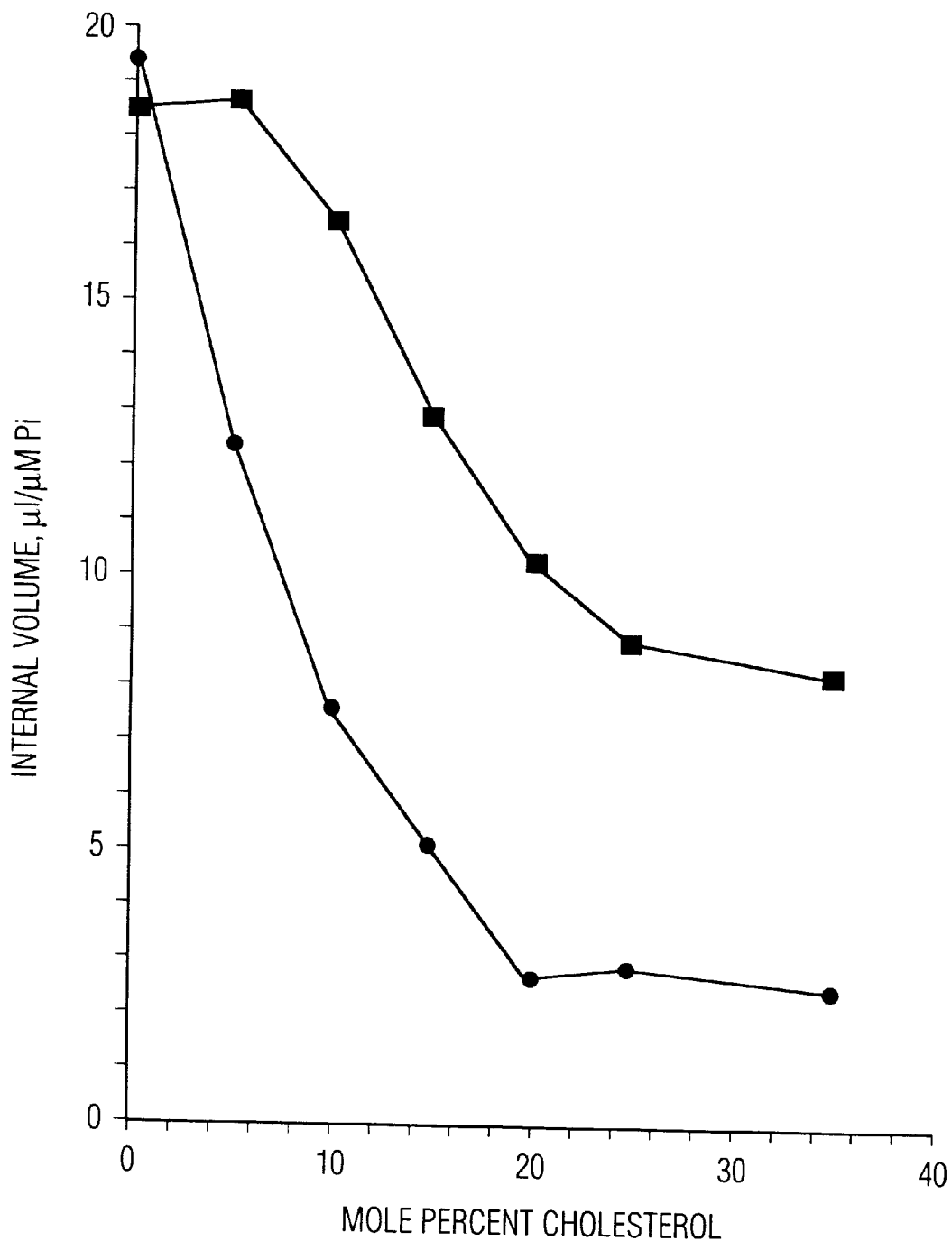
FIG. 29. Incorporation of cholesterol into DPPC IFVS. Final internal volumes of DPPC/Cholesterol IFVs are compared for two methods of cholesterol incorporation into IFVs. DPPC. Filled circles indicate DPPC/Chol IFVs formed directly from DPPC/Chol SUVs of varying mole percent cholesterol Filled squares indicate internal volumes of DPPC/Chol IFVs formed when cholesterol was added in the form of 1:1 DPPC/Chol SUVs in 4.0M ethanol after ethanol-induced DPPC interdigitated sheets were formed.

The interdigitation-fusion technique was very effective as applied to SUVs comprising two or more phospholipids which can undergo ethanol-induced interdigitation-fusion. For example, the internal volume of IFVs formed from DSPC/DPPC or DPPC/DPPG SUVs using 3.0M ethanol were 13.7+/−0.7 and 16.7+/−1.7, respectively. The DSPC mole fractions for the DSPC/DPPC SUVs were 0, 0.20, 0.50, 0.67, 0.80 and 1.00, while the DPPG mole fractions were 0, 0.17, 0.50, 0.67, 0.83 and 1.00. Addition of non-interdigitating lipids to the precursor SUVs (e.g., cholesterol or DOPC) inhibited formation of interdigitated sheets. This is consistent with Komatsu and Rowe (1991), who found that cholesterol inhibited bilayer interdigitation. However, if SUVs containing non-interdigitating lipids were added after the ethanol had been allowed to introduce interdigitation, both components fused in a mixed lipid IFV when the temperature was raised above the Tm (see FIG. 29).

The internal volume of the IFVs formed from DPPC/Chol SUVs rapidly decreased as the cholesterol content was increased. The internal volume of the product IFVs was less than 4 $\mu$l/$\mu$M Pi at 20 mole percent cholesterol. In contrast, adding the cholesterol after the formation of DPPC interdigitated sheets significantly increased the internal volume of the IFVs for a given mole percent of cholesterol. The cholesterol was added in the form of 1:1 mole ratio DPPC/Chol SUVs in 4.0M ethanol. Differential scanning calorimetry of 35 mole percent DPPC/Chol IFVs prepared by either method showed that the DPPC gel-to-liquid crystalline phase transition at 41 deg. C was eliminated in both samples. This demonstrated that cholesterol, which was added after the formation of the DPPC interdigitated sheets, was incorporated into the product DPPC/Chol IFVs.

This invention has been described in terms of specific embodiments set forth in detail herein, but it should be understood that these are by way of illustration and the invention is not necessarily limited thereto. Modifications and variations will be apparent from the disclosure and may be resorted to without departing from the spirit of the inventions those of skill in the art will readily understand. Accordingly, such variations and modifications are considered to be within the purview and scope of the invention and the following claims.

What is claimed is:

1. An interdigitation-fusion liposome prepared by a method which comprises the steps of:
    (a) preparing sized liposomes having an average diameter of less than about 0.40 microns and comprising a symmetrical saturated phospholipid;
    (b) combining the sized liposomes with an amount of an inducer effective to induce fusion of the sized liposomes and interdigitation of the saturated phospholipid at a temperature and for a period of time effective to induce fusion of the sized liposomes and interdigitation of the saturated phospholipid, so as to form an interdigitation-fusion gel from the sized liposomes; and,
    (c) incubating the interdigitation-fusion gel at a temperature above the transition temperature of the saturated phospholipid in the gel for a period of time effective to form an interdigitation-fusion liposome from the gel.

2. The interdigitation-fusion liposome of claim 1, wherein the sized liposomes have an average diameter of no greater than about 0.05 microns.

3. The interdigitation-fusion liposome of claim 2, wherein the sized liposomes have an average diameter of about 0.025 microns.

4. The interdigitation-fusion liposome of claim 1, wherein the symmetrical saturated phospholipid is selected from the group consisting of dimyristoyl phosphatidylcholine, distearoyl phosphatidylcholine, dipalmitoyl phosphatidylcholine, dimyristoyl phosphatidylserine, dipalmitoyl phosphatidylserine, distearoyl phosphatidylserine, dimyristoyl phosphatidylethanolamine, dipalmitoyl phosphatidylethanolamine, distearoyl phosphatidylethanolamine, dimyristoyl phosphatidic acid, distearoyl phosphatidic acid, dipalmitoyl phosphatidic acid, dimyristoyl phosphatidylinositol, distearoyl phosphatidylinositol, dipalmitoyl phosphatidylinositol, hydrogenated soy phosphatidylcholine, dipalmitoyl phosphatidylglycerol, distearoyl phosphatidylglycerol and dimyristoyl phosphatidylglycerol.

5. The interdigitation-fusion liposome of claim 1, further comprising a bioactive agent.

6. The interdigitation-fusion liposome of claim 5, wherein the bioactive agent is an iodinated radiocontrast agent.

7. The interdigitation-fusion liposome of claim 6, wherein the weight ratio of iodine in the iodinated radiocontrast agent to the saturated phospholipid in the interdigitation-fusion liposome is at least about 4:1 (g/g).

8. The interdigitation-fusion liposome of claim 7, wherein the weight ratio of iodine in the iodinated radiocontrast agent to the saturated phospholipid in the interdigitation-fusion liposome is at least about 8:1 (g/g).

9. The interdigitation-fusion liposome of claim 1, wherein the incubation is for a period of time of from about 1 minute to about 1 hour.

10. The interdigitation-fusion liposome of claim 1, wherein the inducer is selected from the group consisting of short-chain alcohols, polyols, chaotropic salts and aqueous buffers.

11. The interdigitation-fusion liposome of claim 10, wherein the inducer is the short-chain alcohol ethanol.

12. The interdigitation-fusion liposome of claim 11, wherein the amount of ethanol is an amount equal to about 5% of the weight of the saturated phospholipid in the sized liposomes to about 20% of the weight of the saturated phospholipid.

13. The interdigitation-fusion liposome of claim 12, wherein the amount of ethanol is equal to about 14% of the weight of the saturated phospholipid in the sized liposomes.

14. A pharmaceutical composition comprising the interdigitation-fusion liposome of claim 1, and a pharmaceutically acceptable carrier.

* * * * *